US011938074B2

(12) United States Patent
Van Engelhoven et al.

(10) Patent No.: US 11,938,074 B2
(45) Date of Patent: Mar. 26, 2024

(54) NECK SUPPORTING EXOSKELETON

(71) Applicants: suitX, Inc., Emeryville, CA (US); The Regents of the University of California, Oakland, CA (US)

(72) Inventors: Logan Van Engelhoven, Berkeley, CA (US); Homayoon Kazerooni, Berkeley, CA (US); James Ren, Mountain View, CA (US); Wayne Yi-Wei Tung, Berkeley, CA (US); Valantyn Koziak, Oakland, CA (US)

(73) Assignees: The Regents of the University of California, Oakland, CA (US); suitX, Inc., Emeryville, CA (US)

( * ) Notice: Subject to any disclaimer, the term of this patent is extended or adjusted under 35 U.S.C. 154(b) by 970 days.

(21) Appl. No.: 16/656,941

(22) Filed: Oct. 18, 2019

(65) Prior Publication Data

US 2020/0121543 A1    Apr. 23, 2020

Related U.S. Application Data

(60) Provisional application No. 62/747,240, filed on Oct. 18, 2018.

(51) Int. Cl.
*A61H 1/02* (2006.01)
*A61F 5/042* (2006.01)
(Continued)

(52) U.S. Cl.
CPC ....... *A61H 1/0296* (2013.01); *A61F 5/05883* (2013.01); *A61F 2005/0197* (2013.01);
(Continued)

(58) Field of Classification Search
CPC .......... A61H 1/0296; A61H 2201/1607; A61H 2201/1621; A61H 2201/1652; A61H 1/02;
(Continued)

(56) References Cited

U.S. PATENT DOCUMENTS 2,904,040 A * 9/1959 Hale ................... A61F 5/055
602/18
3,153,792 A * 10/1964 Marietta ............... A42B 3/127
2/414

(Continued)

FOREIGN PATENT DOCUMENTS

EP         3189945 B1    9/2018
WO      2017117299 A1    7/2017

*Primary Examiner* — Camtu T Nguyen
(74) *Attorney, Agent, or Firm* — Sterne, Kessler, Goldstein & Fox P.L.L.C.

(57) ABSTRACT

A neck supporting exoskeleton is configured to be worn by a person to support the person's head during backward extension motions of the person's neck. The neck supporting exoskeleton may comprise a torso frame configured to be coupled to the person's torso, a head pillow configured to contact the rear portion of the person's head during backward extension motions of the person's neck, a linkage allowing for relative motion between the head pillow and the torso frame in the sagittal plane of the person, and an actuator configured to impose a supporting force onto the head pillow. When the person's neck extension angle increases beyond an engagement angle, the actuator causes the linkage to impose a supporting force onto the head pillow resisting the backward extension motion of the head pillow and the person's head relative to the torso frame thereby providing a support for the person's head.

18 Claims, 41 Drawing Sheets

(51) Int. Cl.
*A61F 5/058* (2006.01)
*A61F 5/01* (2006.01)

(52) U.S. Cl.
CPC .............. *A61H 2201/1607* (2013.01); *A61H 2201/1621* (2013.01); *A61H 2201/1652* (2013.01)

(58) Field of Classification Search
CPC .......... A61H 1/0292; A61H 2201/0157; A61H 2201/1253; A61H 2201/1261; A61H 2201/1609; A61H 2201/1611; A61H 2201/1676; A61H 2203/0406; A61H 2205/04; A61F 5/05883; A61F 5/0197; A61F 2005/0197; A61F 5/042; A61F 5/04
See application file for complete search history.

(56) References Cited

U.S. PATENT DOCUMENTS

| | | | | |
|---|---|---|---|---|
| 3,724,452 | A * | 4/1973 | Nitschke | A61F 5/055 602/18 |
| 4,782,824 | A * | 11/1988 | Davies | A61F 5/055 602/18 |
| 5,141,489 | A | 8/1992 | Sereboff | |
| 5,320,596 | A * | 6/1994 | Catipovic | A61F 5/055 602/18 |
| 5,713,082 | A * | 2/1998 | Bassette | A42B 3/061 2/412 |
| 6,971,123 | B2 * | 12/2005 | Weaver | A63B 71/1291 2/468 |
| 7,306,573 | B2 | 12/2007 | Bonutti | |
| 7,901,327 | B2 * | 3/2011 | Hargis | A61H 1/0296 601/39 |
| 8,715,212 | B1 * | 5/2014 | Ely | A61F 5/02 602/18 |
| 2018/0303650 | A1 | 10/2018 | Doyle | |
| 2019/0290468 | A1 * | 9/2019 | Briant | A61F 5/05883 |
| 2021/0186737 | A1 * | 6/2021 | Smith | A61F 5/05883 |

* cited by examiner

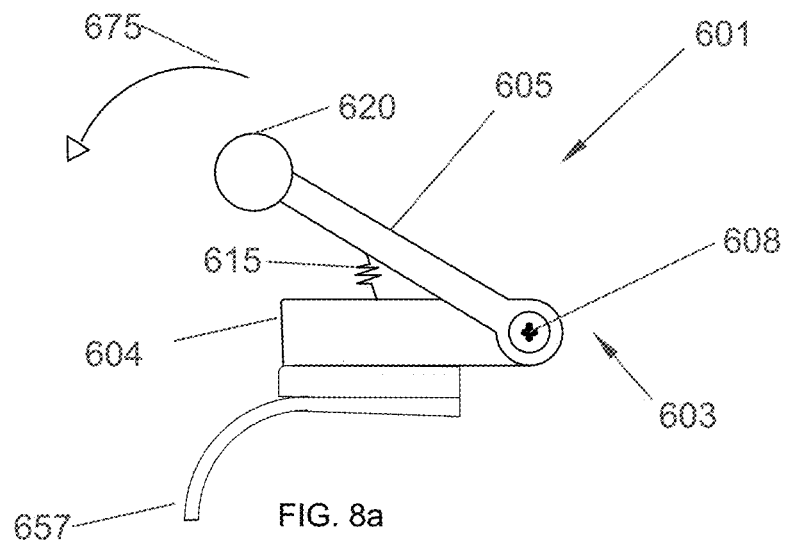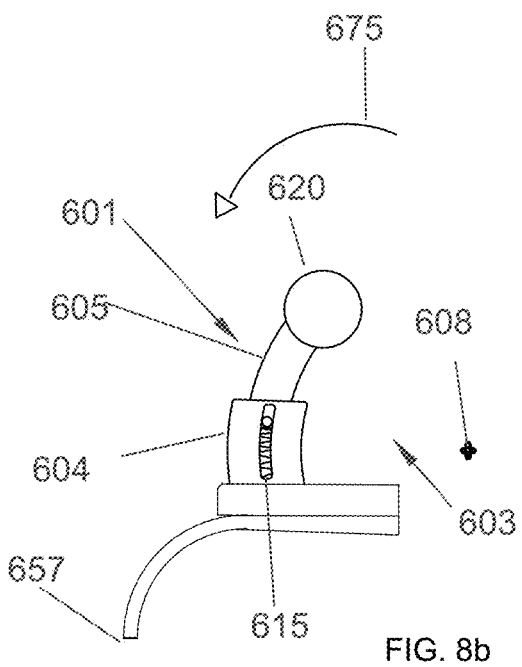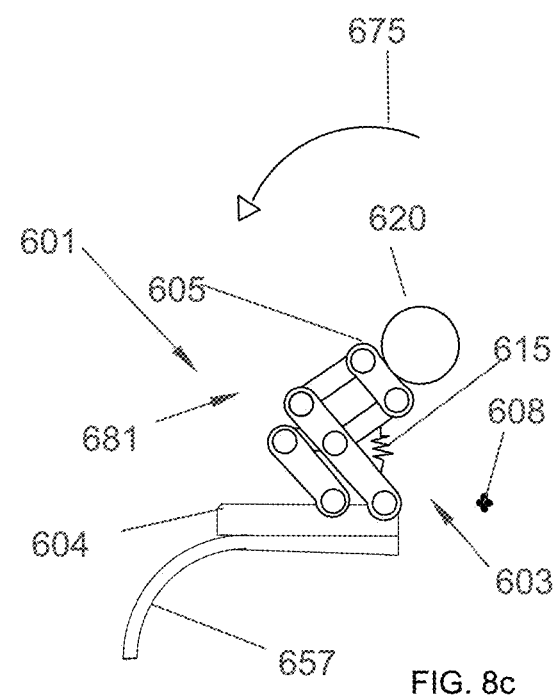

NECK SUPPORTING EXOSKELETON

CROSS-REFERENCE TO RELATED APPLICATIONS

This application claims the benefit under 35 U.S.C. § 119(e) of U.S. Provisional Patent Application 62/747,240, entitled: "DESIGN AND EVALUATION OF A SHOULDER SUPPORTING EXOSKELETON FOR OCCUPATIONAL USE", filed on 18 Oct. 2018, which is incorporated herein by reference in its entirety for all purposes.

TECHNICAL FIELD

The present disclosure pertains to the art of supporting devices for the human head or neck, and more particularly, to a neck supporting exoskeleton configured to at least partially support the weight of the person's head during extension motions of the person's neck.

BACKGROUND

In many industrial settings a worker is required to perform tasks in a position that places strain on the person's neck, commonly during extension motions when the worker is looking upwards. Neck extension is associated in an increase in upper trapezius and sternocleidomastoid activation, especially when both arms are elevated, and may result in overexertion injury if a motion is sustained for long periods or repeated frequently. Examples in industry include but are not limited to welding, grinding, painting, maintenance, electrical work, surgery, assembly, and many others. These tasks often involve many degrees of extension a device should accommodate as well as other contradictory motions the device should not inhibit. For these tasks it would be beneficial to have a device that provides support to compensate for the forces and torques imposed on the head and neck due to gravity at multiple positions of the head. Additionally, the device should impose minimal restriction of movement in other postures where the neck is not extended and not cause excessive contact or friction with the head as movement occurs. Furthermore, the neck supporting exoskeleton should be configured to fit a range of human dimensions and be compatible with various other types of PPE such as hard hats, hearing protection, and safety glasses.

While the focus is on occupational or industrial applications, one of skill in the art may appreciate that many other uses of the invention may exist in other areas of life. A neck supporting exoskeleton as described may find utility in recreation activities when one is viewing something above the head such as belaying a rock climber or for general head support when one is seated or reclined in a home or office setting.

SUMMARY

The present disclosure is directed to systems, devices, and methods for supporting a person's head against gravity, for example, to a neck supporting exoskeleton that supports the users head during extension motions of the person's neck while allowing for substantially uninhibited motion of other postures.

In some examples, a neck supporting exoskeleton is configured to be worn by a person to support the person's head during extension motions of the person's neck. The neck supporting exoskeleton may comprise a torso frame configured to be coupled to the person's torso, a head pillow configured to contact the rear portion of the person's head during extension motions of the person's neck, a linkage coupled been the torso frame and the head pillow allowing for relative motion between the head pillow and the torso frame in the sagittal plane of the person, and an actuator configured to cause the linkage to impose a supporting force onto the head pillow in response to the relative motion of the head pillow relative to the torso frame. When the person's neck extension angle increases beyond an engagement angle, the actuator causes the linkage to impose a supporting force onto the head pillow resisting the extension motion of the head pillow and the person's head relative to the torso frame thereby providing a support for the person's head.

In some examples, a neck supporting exoskeleton is configured to be worn by a person to support the person's head during extension motions of the person's neck. The neck supporting exoskeleton may comprise a torso frame configured to be coupled to the person's torso, a head pillow configured to contact the rear portion of the person's head during extension motions of the person's neck, and a resilient structure coupled to the torso frame from its first end and to the head pillow from its second end, the resilient structure configured to generate a force onto the head pillow in response to extension motion of the head pillow relative to the torso frame. In use when the person's neck extension angle increases beyond an engagement angle, the resilient structure generates a supporting force onto the head pillow resisting the extension motion of the head pillow and the person's head relative to the torso frame thereby providing a support for the person's head.

In some examples, a neck supporting module is configured to attach to a wearable exoskeleton to support the person's head during extension motions of the person's neck. The neck supporting module may comprise an exoskeleton coupler configured to be coupled to the wearable exoskeleton, a head pillow configured to contact the rear portion of the person's head during extension motions of the person's neck, and a resilient structure coupled to the exoskeleton coupler from its first end and coupled to the head pillow from its second end, the resilient structure configured to generate a force onto the head pillow in response to extension motion of the head pillow relative to the exoskeleton coupler. In use when the person's neck extends beyond an engagement angle, the resilient structure generates a forces onto the head pillow resisting the extension motion of the head pillow and the person's head relative to the exoskeleton coupler thereby providing a support for the person's head. The wearable exoskeleton may be an arm supporting exoskeleton, trunk supporting exoskeleton, leg supporting exoskeleton or other human interface device such as a safety harness, tool belt, padding, or protective armor.

In some examples, the neck supporting exoskeleton may be configured so that while the person is standing the neck supporting exoskeleton does not support the weight of the person's head during a neutral posture when the head is straight relative to the torso, but when the person's head begins to extend past an engagement angle the neck supporting exoskeleton begins to apply a supporting force to the back of the person's. In some or all embodiments the neck supporting exoskeleton may also be configured so that while a person is reclined the neck supporting exoskeleton supports the weight of the head in a neutral posture when the head is straight relative to the torso, but when the person's head flexes past an engagement angle the neck supporting exoskeleton ceases to apply a supporting force to the person's head. Some or all of the embodiments may further comprise a resting angle where the neck supporting exoskeleton or module prevents further extension motion of the person's head to support the full weight of the person's head. The neck supporting exoskeleton or module may be configured to adjust the extension angle or the resting angle, and may comprise means to create multiple engagement angles or multiple resting angles.

The devices, systems, or methods herein may counterbalance all or part of the weight of the person's head as the person performs one or more tasks, which may reduce fatigue of the muscles, tendons, or joints in the neck or back. In addition, the neck supporting exoskeleton or module described may separate from the users head during non-supported motions to allow for more uninhibited motion of the person's head. When the neck supporting exoskeleton applies a supporting force to the person's head, the reaction forces and torques may be transmitted to the person's torso by a system of resilient structures, linkages, actuators, and couplers. Thus when the neck supporting exoskeleton or module is worn by a user at least a portion of the weight of the person's head may be transmitted to the shoulders, hips, sides or other regions of the torso which may be more capable of receiving or supporting the forces.

Other aspects and features of the present disclosure will become apparent from consideration of the following description taken in conjunction with the accompanying drawings.

BRIEF DESCRIPTION OF THE DRAWINGS

It may be appreciated that the illustrative apparatus shown in the drawings are not necessarily drawn to scale, with emphasis instead being placed on illustrating the various aspects and features of the illustrated embodiments.

FIG. 8a shows an embodiment of a linkage with a first segment configured to rotate relative to a second segment.

FIG. 8b shows an alternate embodiment of a linkage with a first segment configured to translate relative to a second segment.

FIG. 8c shows an alternate embodiment of a linkage with a plurality of rotating linkages.

DETAILED DESCRIPTION

In the following description, numerous specific details are set forth in order to provide a thorough understanding of the present invention. The present invention may be practiced without some or all of these specific details. In other instances, well known process operations have not been described in details to avoid obscuring the present invention. While the invention will be described in conjunction with the specific examples, it will be understood that it is not intended to limit the invention to the examples.

Figure 1:
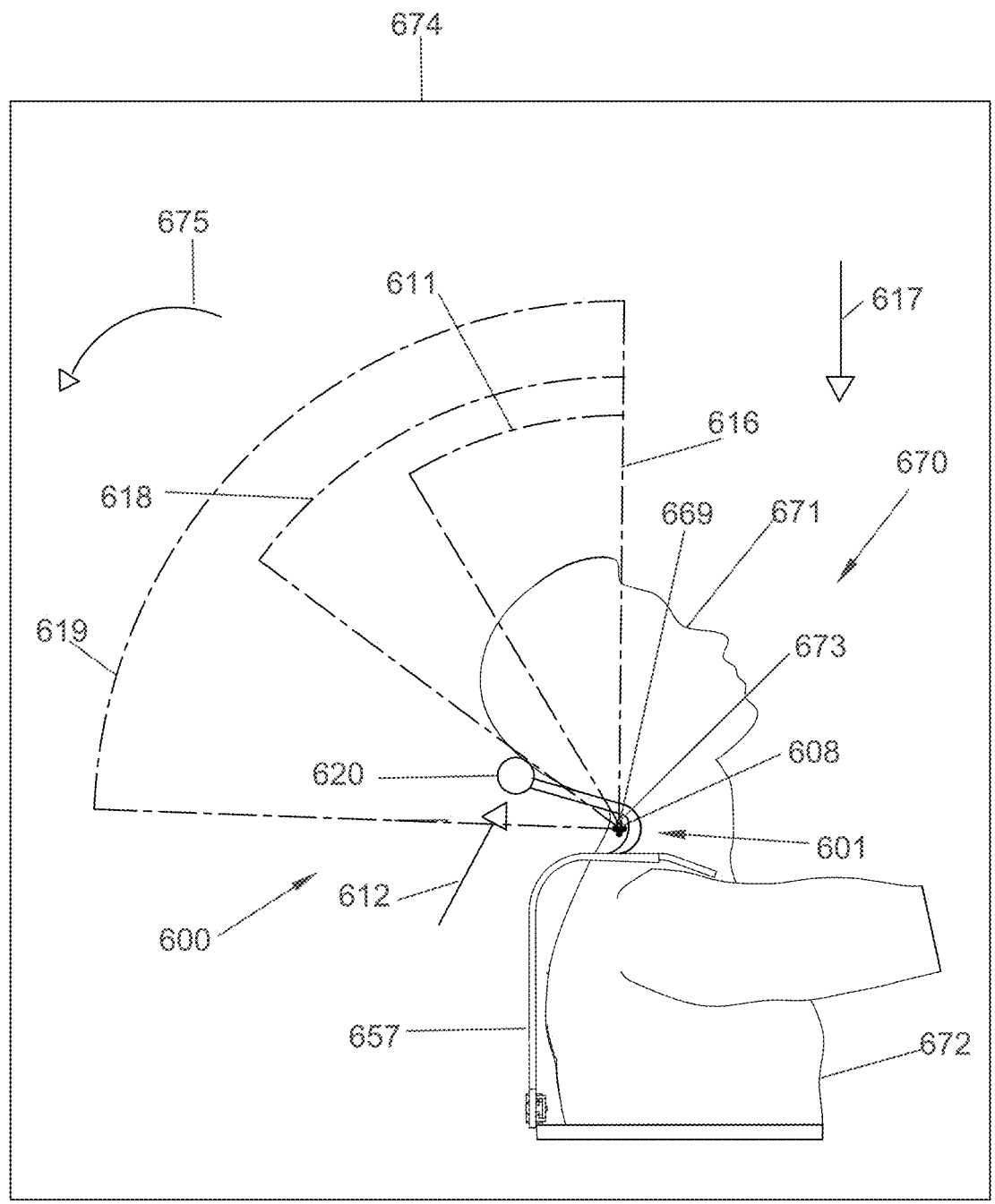
FIG. 1 shows a side view of a neck supporting exoskeleton applying a supporting force when a person's neck extension angle is greater than an engagement angle.

FIG. 1 shows an embodiment of a neck supporting exoskeleton 600 configured to be worn by a person 670. Neck supporting exoskeleton 600 supports the extension motion 675 of person's head 671. Neck supporting exoskeleton 600 comprises torso frame 657 configured to be coupled to person's torso 672 and head pillow 620 configured to contact the rear portion of person's head 671 during extension motions 675 of person's neck 673. Neck supporting exoskeleton also comprises resilient structure 601 coupled to torso frame 657 from its first end and to head pillow 620 from its second end, resilient structure 601 may be configured to generate supporting force 612 onto head pillow 620 in response to extension motion 675 of head pillow 620 relative to torso frame 657. When neck extension angle 618 increases beyond engagement angle 611, resilient structure 601 generates supporting force 612 onto head pillow 620 resisting extension motion 675 of head pillow 620 and person's head 671 relative to torso frame 657 thereby providing support for person's head 671, In some embodiments, resilient structure 601 is configured to generate a torque between head pillow 620 and torso frame 657 in a direction opposing extension motion 675 of person's neck 673. When person's neck 673 extends beyond engagement angle 611, resilient structure 601 provides a torque opposite extension motion 675 of head pillow 620 relative to torso frame 657, causing head pillow 620 to apply supporting force 612 to person's head 671, thereby providing support for person's head 671. In some embodiments, resilient structure 601 comprises a leaf spring that both controls the motion of head pillow 620 relative to torso frame 657 and generates supporting force 612 on to head pillow 620 in response to extension motion 675 of head pillow 620 relative to torso frame 657.

Extension motion 675 may refer to motion of the person's head 671 relative to person's torso 672, or more simply the motion of person's neck 673, which connects person's head 671 and person's torso 672, In general, extension motion 675 occurs when person 670 looks upwards. The axis of extension motion 675 occurs approximately about person's neck 673, but may be shifted outside of person's neck 673 in some cases due to the complexities of the spine. In some embodiments, extension motion 675 occurs in sagittal plane 674 of person 670. Extension motion 675 may also refer to motion of head pillow 620 relative to torso frame 657, which corresponds to motion of person's head 671 relative to person's torso 672 when neck supporting exoskeleton 600 is worn by the person 670. In some embodiments, extension motion 675 between head pillow 620 and torso frame 657 is defined about first rotational axis 608. Flexion motion is defined as a motion opposite to extension motion 675.

Supporting force 612 generated onto head pillow 620 by resilient structure 601 is in turn applied onto person's head 671 by head pillow 620. Supporting force 612 opposes extension motion 675 of person's head 671 to support gravitational forces on person's head 671. In the preferred embodiment the amount of force between head pillow 620 and resilient structure 601 is the same as the force between head pillow 620 and person's head 671 and the term "supporting force" may be used to refer to the forces between head pillow 620 and resilient structure 601 or between head pillow 620 and person's head 671. The configuration of head pillow 620 may after the angle or surface area of supporting force 612 when applied to person's head, compared to supporting force 612 applied between resilient structure 601 and head pillow 620. The supporting torque is represented as a torque between person's torso 672 and person's head 671, or between head pillow 620 and torso frame 657, that is applied as supporting force 612 against the back of person's head 671 by head pillow 620. The supporting torque or supporting force 612 may be used to support person's head 671 when person's head 671 is held statically in place relative to person's torso 672. The supporting torque or supporting force 612 may also be used to support person's head 671 when moving in extension motion 675 relative to person's torso 672. Similarly, supporting torque or supporting force 612 may also be used to support person's head 671 when moving in flexion motion relative to person's torso 672, as long as neck extension angle 618 remains greater than engagement angle 611. The reaction forces and torques from supporting force 612 or the supporting torque may be distributed to person's torso 672 by torso frame 657. Supporting force 612 may be created by a number of different forces and torques within resilient structure 601 as described later.

As shown in FIG. 1, neck extension angle 618 is defined as the angle of person's head 671 relative to person's torso 672. Neck extension angle 618 is defined about an approximate neck rotational axis 669 centered about the person's spine either to the center of mass of person's head 671 or to the rear portion of person's head 671. Neck extension angle 618 may be determined relative to neutral angle 616 of the person's neck. Neutral angle 616 of the person's neck, may similarly be described as neutral angle 616 of person's head 671 relative to person's torso 672. Neutral angle 616 occurs when person 670 is in a resting position with a natural un-loaded curvature of the spine. Neutral angle 616 commonly occurs when person 670 is standing straight with person's head 671 balanced about person's neck 673 above person's torso 672, so that minimal muscle forces are needed. At neutral angle 616 the persons spine is in a natural curvature. Neutral angle 616 may similarly occur when person 670 is in a reclined or supine position when person's head 671 is in same position relative to person's torso 672 as described when person 670 is standing upright. When person's head 671 is at neutral angle 616 relative to person's torso 672, neck extension angle 618 is zero. As person's head 671 moves in extension motion 675, neck extension angle 618 increases. As person's head 671 moves in flexion motion, neck extension angle 618 decreases. Neck extension angle 618 may also be defined as the angle of head pillow 620 relative to torso frame 657 when neck supporting exoskeleton 600 is worn by person 670.

When person's neck 673 is substantially strait, the moment about person's neck 673 due to the weight of person's head 671 is minimal. Here no support is needed. When person's neck 673 undergoes extension motions 675 and person's head 671 extends by neck extension angle 618 away from gravity line 617, a torque is created about person's neck 673 due to the mass of person's head 671 and the distance between the center of gravity of person's head 671 and neck rotational axis 669. During this extension motion 675, a neck supporting torque, applied to the back of person's head 671 as supporting force 612 counters the torque due gravity. While the primary embodiments supports extension motions 675 one of skill in the art may appreciate that similar forces can be applied for motions of flexion or lateral flexion through a simple rearrangement of the described configuration of neck supporting exoskeleton 600. As neck extension angle 618 of person's head 671 increases, so does the gravitational torque about person's neck 673. In some embodiments, the torque created by neck supporting exoskeleton 600 actuator 615 or resilient structure 601 increases as neck extension angle 618 of person's head 671 increases.

In some embodiments, supporting force 612 generated by resilient structure 601 increases as neck extension angle 618 of person's head 671 increases. The increase in supporting force 612 may be linear or sinusoidal depending on the configuration of resilient structure 601 or actuator 615 with respect to linkage 603. An increasing supporting force 612 may be useful to more accurately counter the force of gravity on person's head 671, which increases in a sinusoidal manner as person's neck extension angle 618 increases. In some embodiments, supporting force 612 is configured to increase at the same rate relative to neck extension angle 618 as the gravity forces in order to create a weightless effect of person's head 671 throughout the person's extension range of motion for values of neck extension angle 618 greater than engagement angle 611. In other embodiments, supporting force 612 may be configured to increase more rapidly than the increase in gravitational forces as neck extension angle 618 increases in order to discourage high angles of neck extension. Still in other embodiments, neck supporting exoskeleton 600 may be configured to deliver a constant value of supporting force 612 as neck extension angle 618 of person's head 671 increases.

Figure 2:
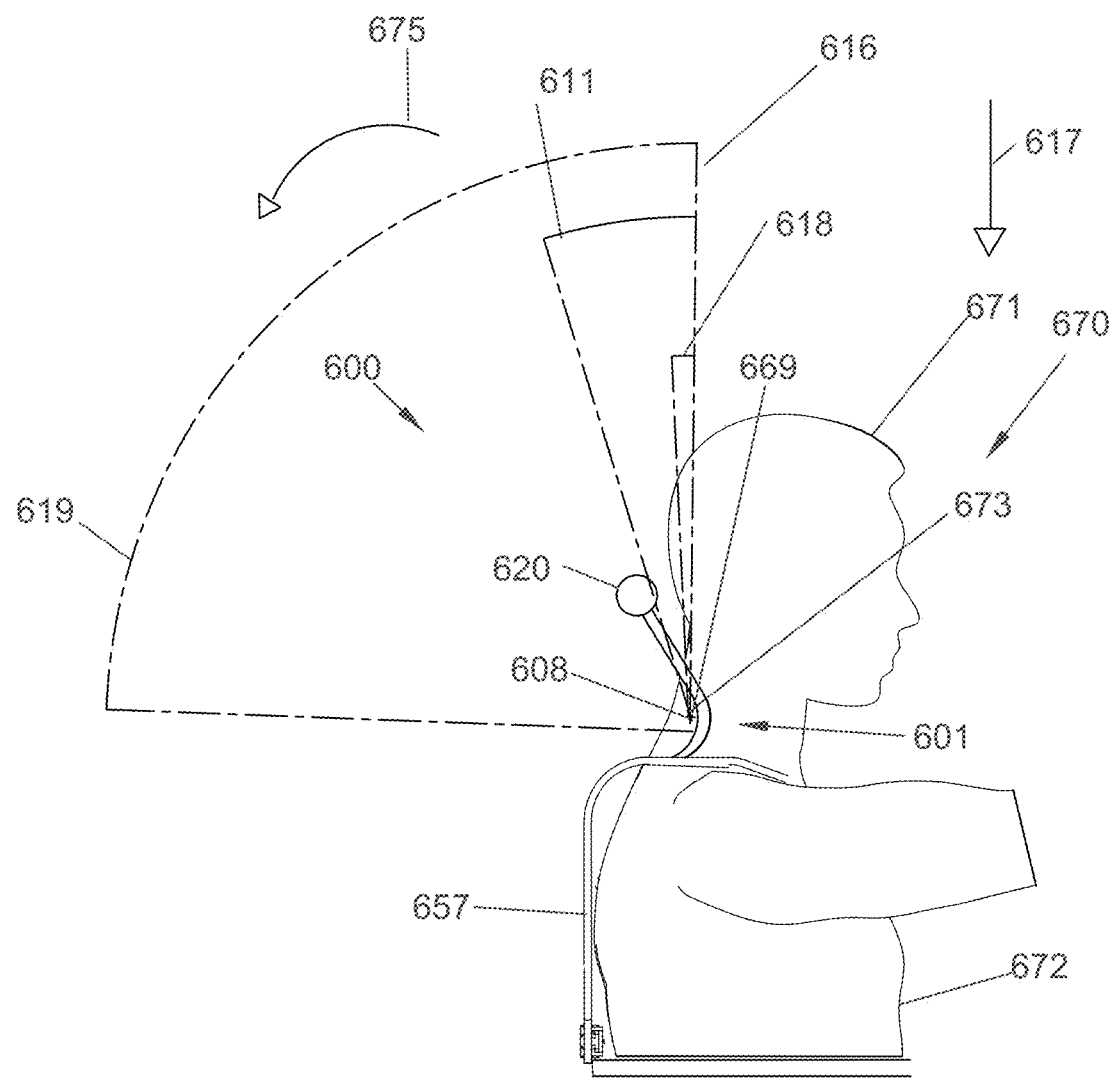
FIG. 2 shows a side view of a neck supporting exoskeleton not applying a supporting force when a person's neck extension angle is less than an engagement angle.

In some embodiments, as shown in FIG. 2, when neck extension angle 618 is less than engagement angle 611 neck supporting exoskeleton 600 does not apply supporting force 612. Engagement angle 611 is neck extension angle 618 where neck supporting exoskeleton 600 begins to apply supporting torque or supporting force 612 to support the weight of person's head 671 against gravity. When person's neck extension angle 618 becomes equal to engagement angle 611 neck supporting exoskeleton 600 begins to apply supporting force 612 to person's head 671. As neck extension angle 618 becomes greater than engagement angle 611 neck supporting exoskeleton 600 continues to apply a supportive torque to person's head 671. In some embodiments, as shown in FIG. 2, when neck extension angle 618 is less than engagement angle 611 person's head 671 does not contact head pillow 620. This allows person's head 671 to twist, flex forward, or flex laterally freely without contact with neck supporting exoskeleton 600. Neck supporting exoskeleton 600 may be designed so that the value of engagement angle 611 is such that the person receives the maximum range of supported motion during at risk postures with minimal inhibition of secondary postures when support is not desired. In some embodiments, engagement angle 611 corresponds to the position of head pillow 620 relative to torso frame 657 when resilient structure 601 is un-stretched or in its un-loaded neutral shape.

As shown in FIG. 1 and FIG. 2, neck supporting exoskeleton 600 may be configured to be used when neutral angle 616 of person's neck 673 is parallel to gravity line 617 in which the force of gravity acts. In this embodiment, neck extension angle 618 must increase in extension motion 675 from neutral angle 616 until engagement angle 611 is reached. This corresponds to when person 670 is standing upright and neck supporting exoskeleton 600 is configured to apply supporting force 612 to person's head 671 when person 670 looks upward.

Figure 3:
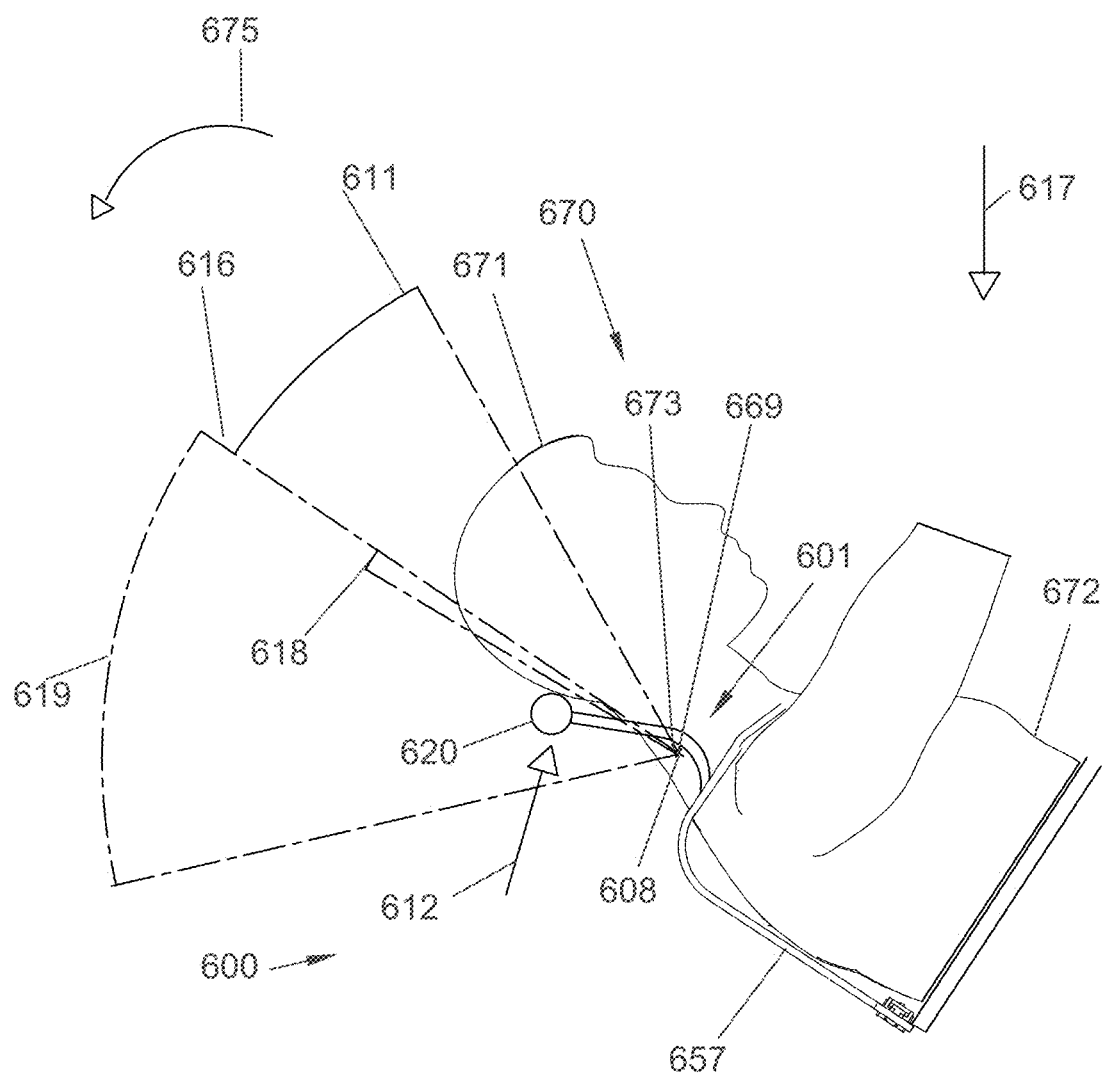
FIG. 3 shows a side view of a neck supporting exoskeleton applying a supporting force to a person in a reclined position.

In another embodiment, shown in FIG. 3, neck supporting exoskeleton 600 is configured to be used when neutral angle 616 of person's neck 673 is rotated in extension motion 675 relative to gravity line 617. In this embodiment, neck extension angle 618 must decrease from neutral angle 616, corresponding to flexion motion opposite extension motion 675, until engagement angle 611 is reached. This corresponds to when person 670 is in a reclined or supine position and neck supporting exoskeleton 600 is configured to apply supporting force 612 to person's head 671 to help person 670 maintain neutral angle 616 of person's head 671 with reduced muscle forces. In this configuration person 670 is able to move person's head 671 in both flexion motion and extension motion 675 from neutral angle 616 while receiving supporting force 612 from neck supporting exoskeleton 600.

In some embodiments, as shown in FIG. 1, resilient structure 601 is configured to move head pillow 620 relative to torso frame 657 in sagittal plane 674 of person 670. Resilient structure 601 may also be configured to rotate head pillow 620 relative to torso frame 657 in sagittal plane 674 of person 670 about first rotational axis 608 which passes approximately through person's neck 673. In some embodiments, first rotational axis 608 is aligned with person's neck rotational axis 669. When first rotational axis 608 is aligned with person's neck 673 or neck rotational axis 669, the angle of person's head 671 relative to person's torso 672 is substantially the same as the angle of head pillow 620 relative to torso frame 657. This alignment reduces relative motion between head pillow 620 and person's head 671 or torso frame 657 and person's torso 672 during extension motions 675 of persons neck 673 when neck supporting exoskeleton 600 is worn by person 670, which could lead to discomfort of person 670. In some embodiments, first rotational axis 608 may drift as head pillow 620 moves relative to torso frame 657. In some embodiments, first rotational axis 608 is substantially orthogonal to gravity line 617.

Figure 4A:
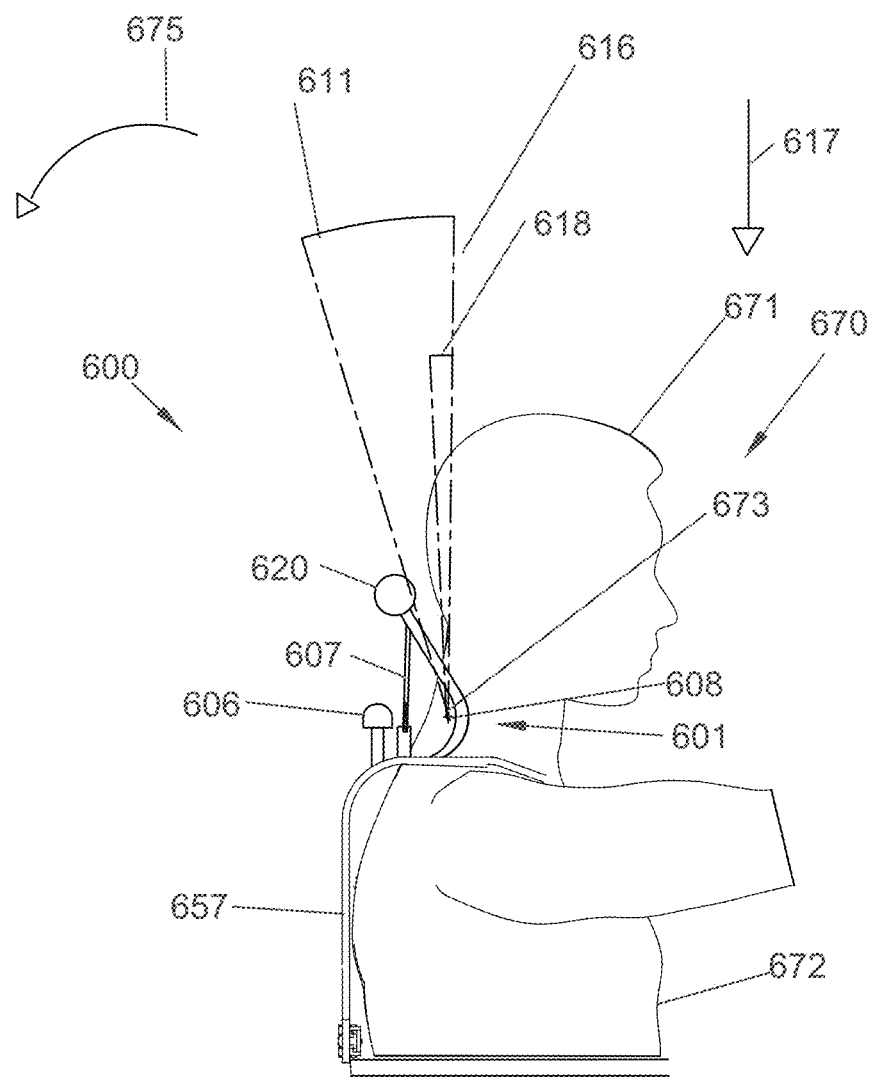
FIG. 4a shows a side view of a neck supporting exoskeleton with a flexion hard stop in a first engagement position.
Figure 4B:
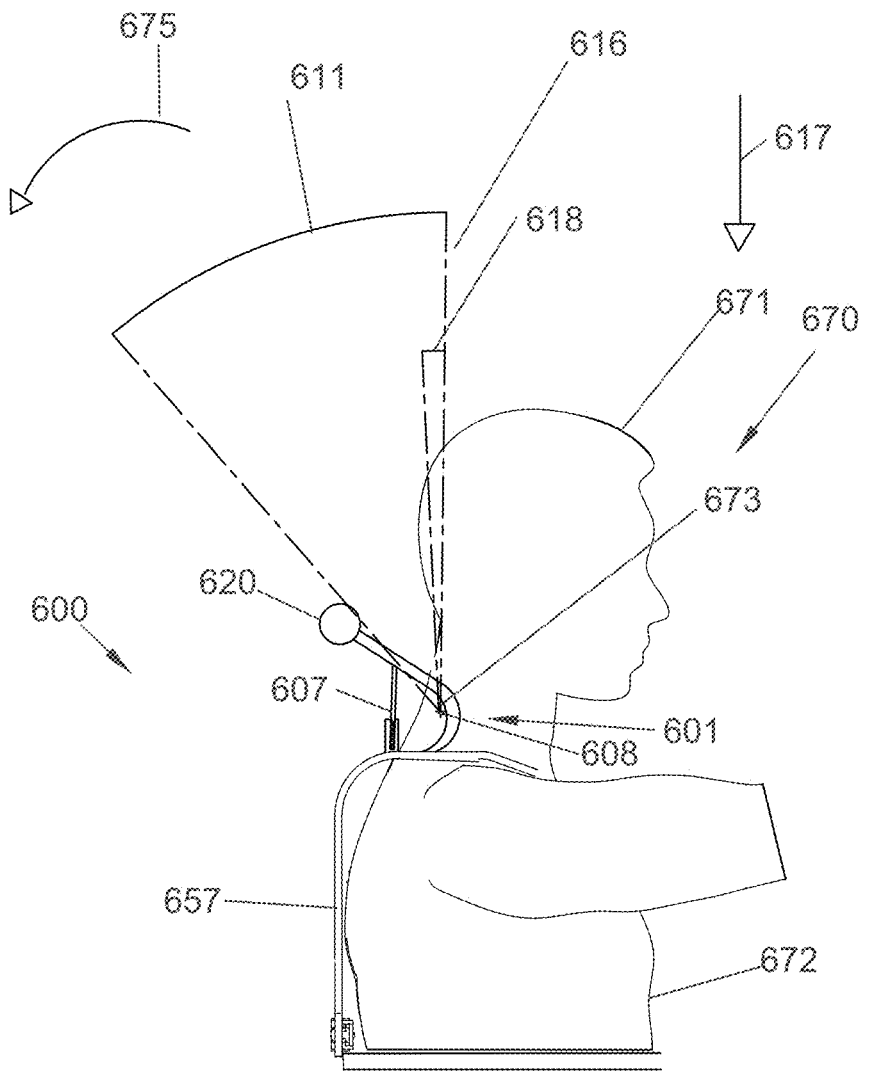
FIG. 4b shows a side view of a neck supporting exoskeleton with a flexion hard stop in a second engagement position.
Figure 5A:
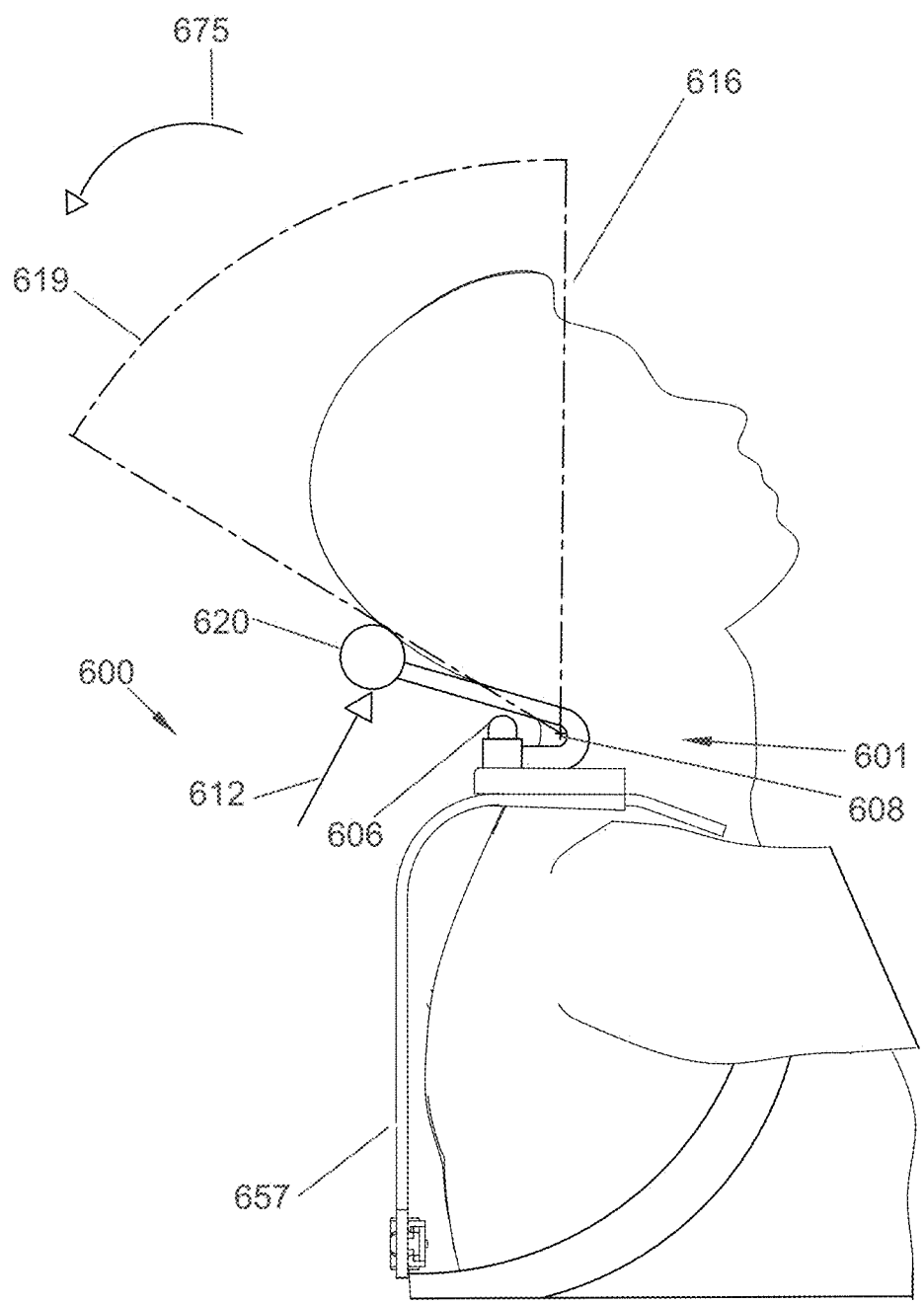
FIG. 5a shows a side view of a neck supporting exoskeleton with an extension hard stop in a first resting position.
Figure 5B:
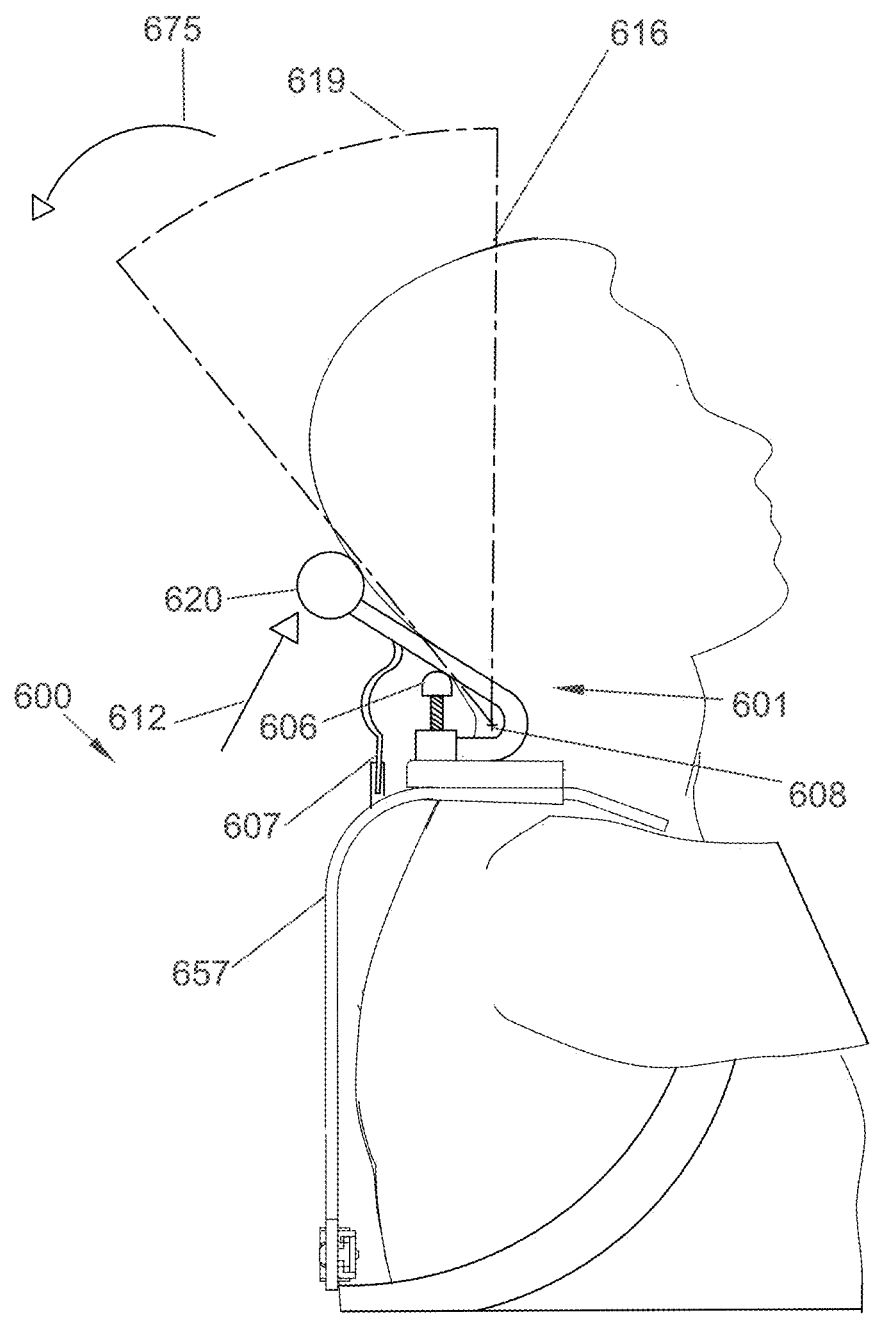
FIG. 5b shows a side view of a neck supporting exoskeleton with an extension hard stop in a second resting position.

In some embodiments, as shown in FIG. 4a and FIG. 4b neck supporting exoskeleton 600 further comprises flexion hard stop 607 coupled to head pillow 620 from its first end and coupled to torso frame 657 from its second end. At engagement angle 611, flexion hard stop 607 is configured to prevent head pillow 620 from moving relative to torso frame 657 in flexion motion corresponding to a decrease in neck extension angle 618. Flexion hard stop 607 may define engagement angle 611 and resilient structure 601 may be preloaded against flexion hard stop 607 to increase supporting force 612. The configuration of the neck supporting exoskeleton 600 or head pillow 620 relative to torso frame 657 at engagement angle 611 may be referred to as engagement position. In some embodiments, flexion hard stop 607 comprises a flexible tensile element such as a cable, wire, or rope. Flexion hard stop 607 may be translationally coupled to either torso frame 657 or head pillow 620 to adjust engagement angle 611. The translational coupling between flexion hard stop 607 and torso frame 657 or head pillow 620 may be achieved by a screw, indexing switch, or similar mechanism. FIG. 4a shows an embodiment where flexion hard stop 607 is translationally coupled to torso frame 657 and configured to prevent flexion motion of head pillow 620 relative to torso frame 657 to create first value of engagement angle 611. In FIG. 4b the coupling between flexion hard stop 607 and torso frame 657 is adjusted so that flexion hard stop 607 is configured to prevent flexion motion of head pillow 620 relative to torso frame 657 to create second value of engagement angle 611. It can be seen that when flexion hard stop 607 is shortened engagement angle 611 increases and when flexion hard stop 607 is lengthened engagement angle 611 decreases. In some embodiments, flexion hard stop 607 may adjust in length to adjust engagement angle 611. In FIG. 5b, when neck extension angle 618 is greater the engagement angle 611, it can be seen that flexion hard stop 607 goes slack and does not affect the motion of head pillow 620 relative to torso frame 657.

In some embodiments, neck supporting exoskeleton 600 is configured so that resilient structure 601 allows for the full extension range of motion of person's head 671. In other embodiments, as shown in FIG. 5a and FIG. 5b, neck supporting exoskeleton may further comprise extension hard stop 606 configured to prevent head pillow 620 from moving relative to torso frame 657 in extension motion 675 that corresponds to an increase in neck extension angle 618. Extension hard stop 606 may define a resting angle 619 after which person's head 671 is prevented from moving in extension motion 675 relative to person's torso 672. The configuration of neck supporting exoskeleton 600 or the position of head pillow 620 relative to torso frame 657 at resting angle 619 may be described as resting position, Resting angle 619 may similarly be defined as the angle at which head pillow 620 is prevented from moving in extension motion 675 relative to torso frame 657 when neck supporting exoskeleton 600 is worn by person 670. Extension hard stop 606 may be used to limit person's neck 273 from entering dangerous postures or to provide full support of person's head 671 at a specific neck extension angle 618 or resting angle 619. In some embodiments, extension hard stop 606 is moveably coupled to resilient structure 601, head pillow 620, or torso frame 657 to adjust resting angle 619. The moveable coupling of extension hard stop 606 may be achieved through a screw, switch, or other similar rotating or translating mechanism, A first position of extension hard stop 606 coupled to torso frame 657 is shown in FIG. 5a that prevents head pillow 620 from moving in extension motion 675 relative to torso frame 657 at a first value of resting angle 619. A second position of extension hard stop 606 coupled to torso frame 657 is shown in FIG. 5a that prevents head pillow 620 from moving in extension motion 675 relative to torso frame 657 at second value of resting angle 619. It can be seen that when extension hard stop 606 is shortened resting angle 619 increases and when extension hard stop 606 is lengthened resting angle 619 decreases. In FIG. 4a it can be observed that when person's head 671 flexes relative to person's torso 672 past resting angle 619, extension hard stop 606 separates from head pillow 620. It should be obvious to one skilled in the art that the configuration of flexion hard stop 607 and extension hard stop 606 may be similarly situated between resilient structure 601 head pillow 620 or torso frame 657.

Figure 6A:
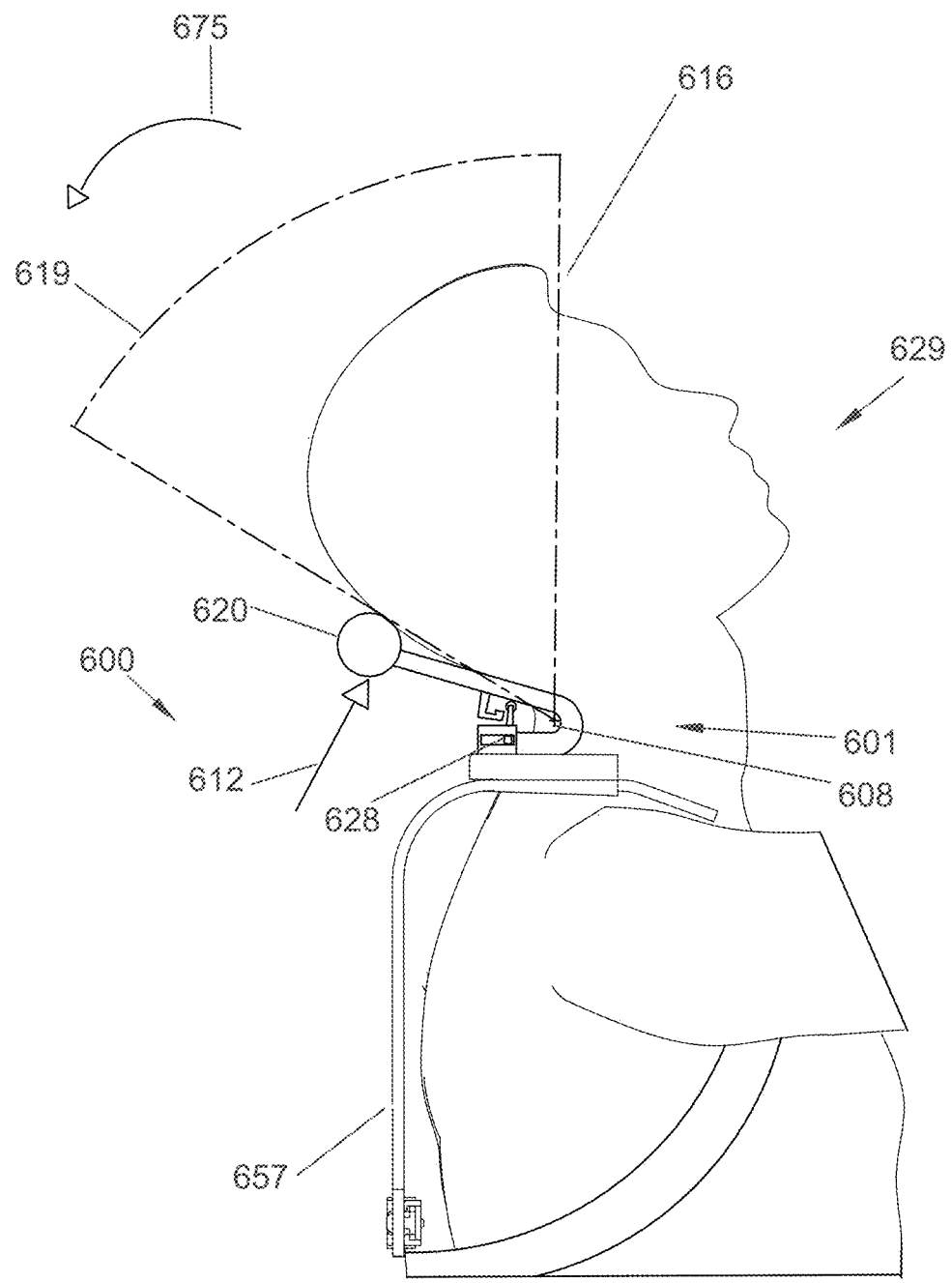
FIG. 6a shows a side view of a neck supporting exoskeleton in a stowed position with a stow lock in a first position.
Figure 6B:
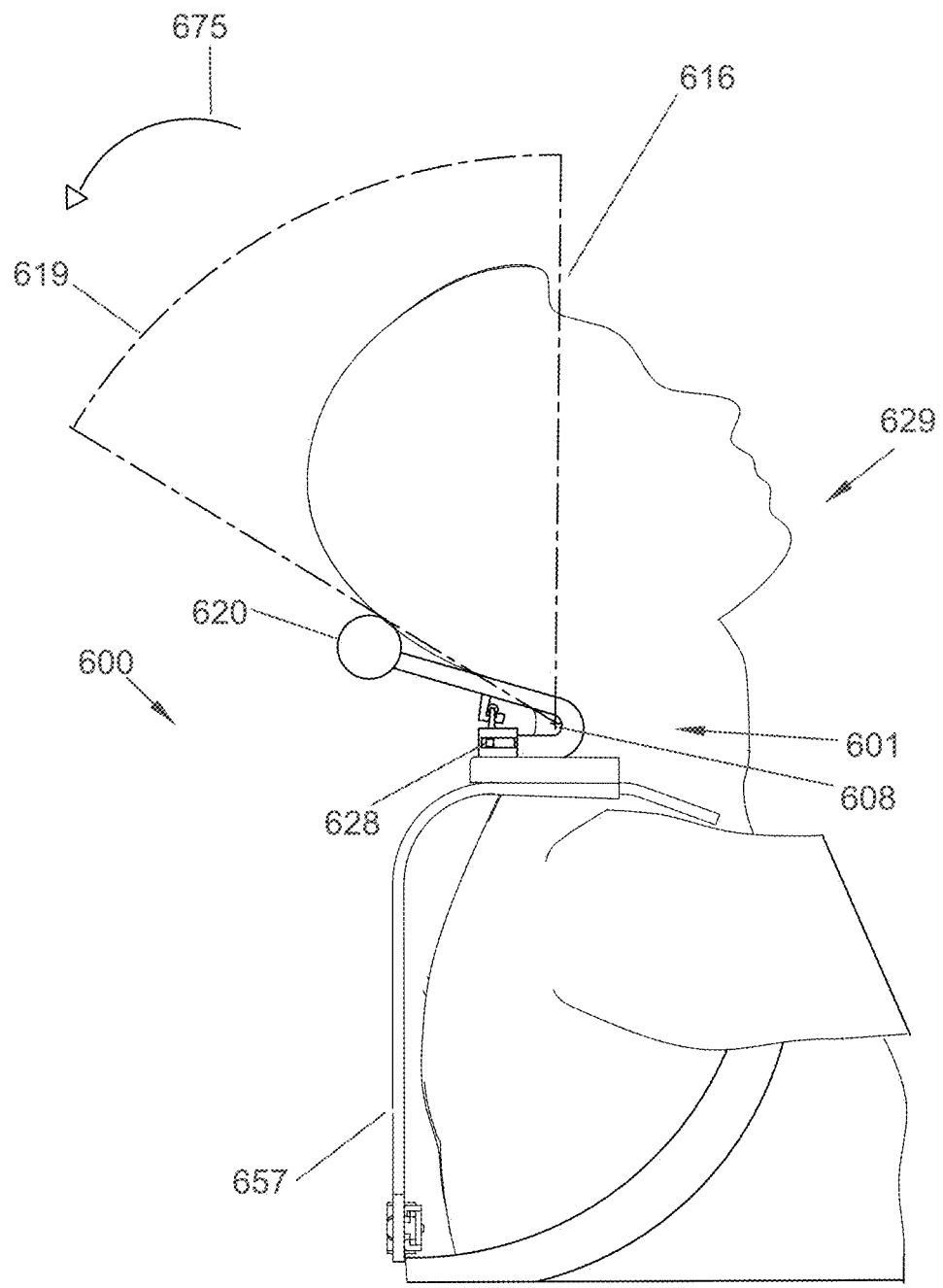
FIG. 6b shows a side view of a neck supporting exoskeleton in a stowed position with a stow lock in a second position.
Figure 6C:
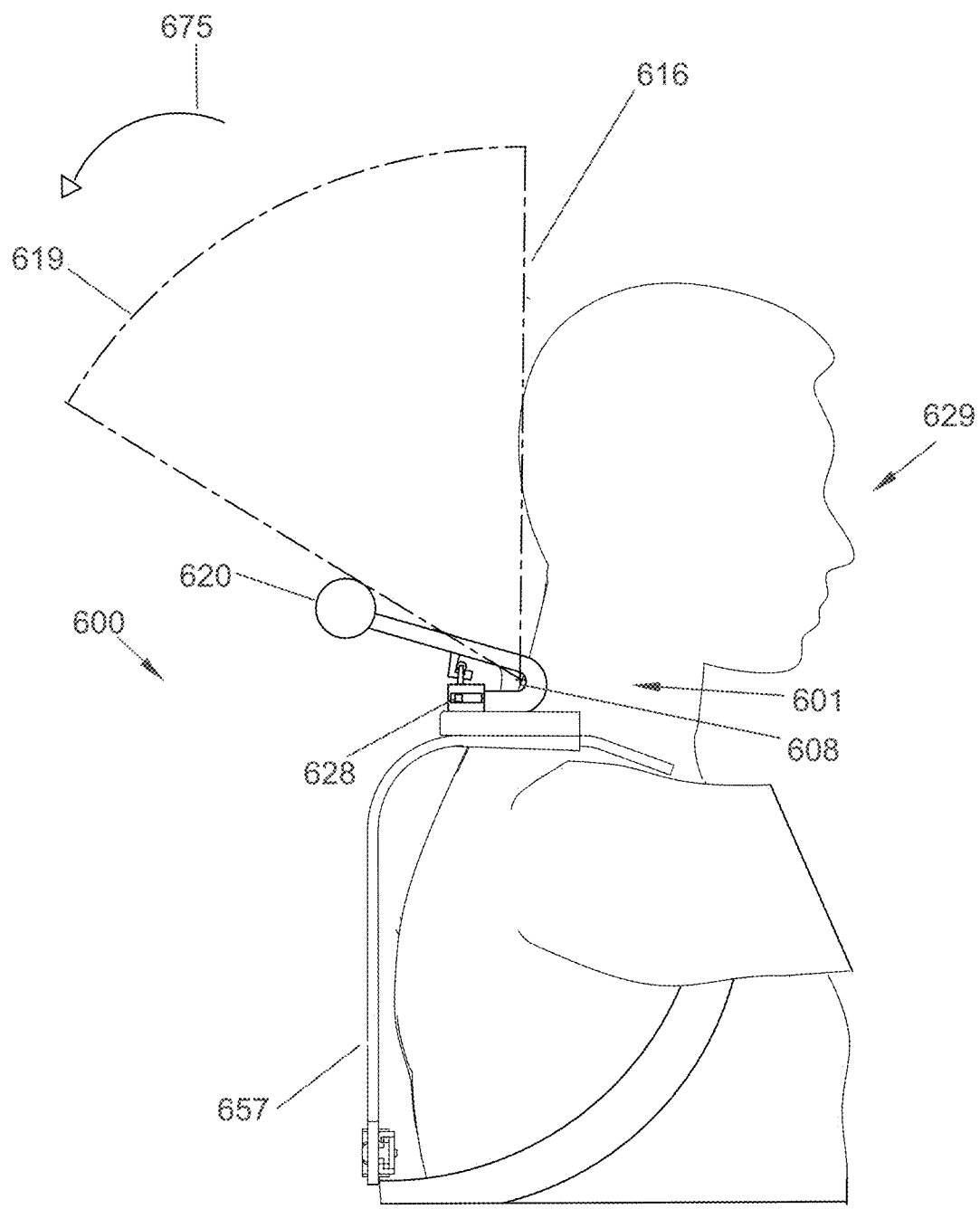
FIG. 6c shows a side view of a neck supporting stowed behind the person's head.

In some embodiments, as shown in FIG. 6a, FIG. 6b, and FIG. 6c, neck supporting exoskeleton 600 further comprises stow lock 628. Stow lock 628 is configured to selectively prevent flexion motion of head pillow 620 relative to torso frame 657. Stow lock 628 may be moveably coupled to either torso frame 657 or head pillow 620 between at least a first position and a second position. FIG. 6a shows neck supporting exoskeleton 600 when stow lock 628 is in a first position and head pillow 620 is at a stow position 629 relative to torso frame 657. Stow position 629 corresponds to the position of head pillow 620 relative to torso frame 657 that stow lock 628 is configured to engage in. In its first position, stow lock 628 does not prevent head pillow 620 from moving relative to torso frame 657 and resilient structure 601 generates supporting force 612 onto head pillow 620 resisting extension motion 675 of head pillow 620 and person's head 671 thereby providing a support for person's head 671. FIG. 6b shows neck supporting exoskeleton 600 when stow lock 628 is in a second position and head pillow 620 is at stow position 629 relative to torso frame 657. Stow lock 628 prevents head pillow 620 from moving relative to torso frame 657 in a motion that corresponds to a decrease in neck extension angle 618 so that head pillow 620 does not apply supporting force 612 to person's head 671. When stow lock 628 is in the second position and head pillow 620 is at stow position 629 relative to torso frame 657, head pillow 620 will remain in stow position 629 as person's head 671 moves in flexion motion as shown in FIG. 6c. This allows neck supporting exoskeleton 600 to store head pillow 620 out of a workspace of person 670 when neck supporting exoskeleton is not in use. Stow lock 628 may also be used when person 670 must bend forward while wearing neck supporting exoskeleton 600, which could cause engagement angle 611 to shift in a flexion motion relative to gravity line 617 and cause neck supporting exoskeleton 600 to inhibit the person. Stow lock 628 may comprise a rotating hook, magnetic clasp, buckle, screw, latch, switch or similar mechanism known to one skilled in the art.

In another embodiment, resilient structure 601 further comprises linkage 603 coupled to torso frame 657 from its first end and to head pillow 620 from its second end, linkage 603 allowing for relative motion between head pillow 620 and torso frame 657. In some embodiments, linkage 603 comprises first segment 604 coupled to torso frame 657 and second segment 605 coupled to head pillow 620, linkage 603 configured to control the motion of head pillow 620 relative to torso frame 657. Linkage 603 may control motion by means of flexion hard stop 607, extension hard stop 606, stow lock 628, hard stop switch 661, by defining first rotational axis 608, or other means. Linkage 603 is configured to allow for relative motion between head pillow 620 and torso frame 657. Resilient structure 601 may also comprise at least one actuator 615 configured to impose supporting force 612 onto head pillow 620 in response to motion of head pillow 620 relative to torso frame 657. When the person's neck extends beyond engagement angle 611, actuator 615 causes linkage 603 to impose supporting force 612 onto head pillow 620 resisting the extension motion 675 of head pillow 620 and person's head 671 relative to torso frame 657 thereby providing support for person's head 671. In some embodiments, actuator 615 provides supporting torque resisting extension motion 675 of head pillow 620 relative to torso frame 657 thereby providing support for person's head 671. In this embodiment, linkage 603 directs the motion of head pillow 620 relative to torso frame 657 while actuator 615 applies forces or torques to the direction of motion defined by linkage 603. When person's neck 673 extends beyond engagement angle 611, actuator 615 provides torque resisting extension motion 675 of head pillow 620 relative to torso frame 657 thereby providing support for person's head 671. In some embodiments, linkage 603 is configured to move head pillow 620 relative to torso frame 657 in sagittal plane 674 of person 670. Linkage 603 may further be configured to rotate head pillow 620 relative to torso frame 657 about first rotational axis 608 which passes approximately through person's neck 673. In some embodiments, first rotational axis 608 is substantially orthogonal to gravity line 617 when person 670 is standing upright.

Figure 7A:
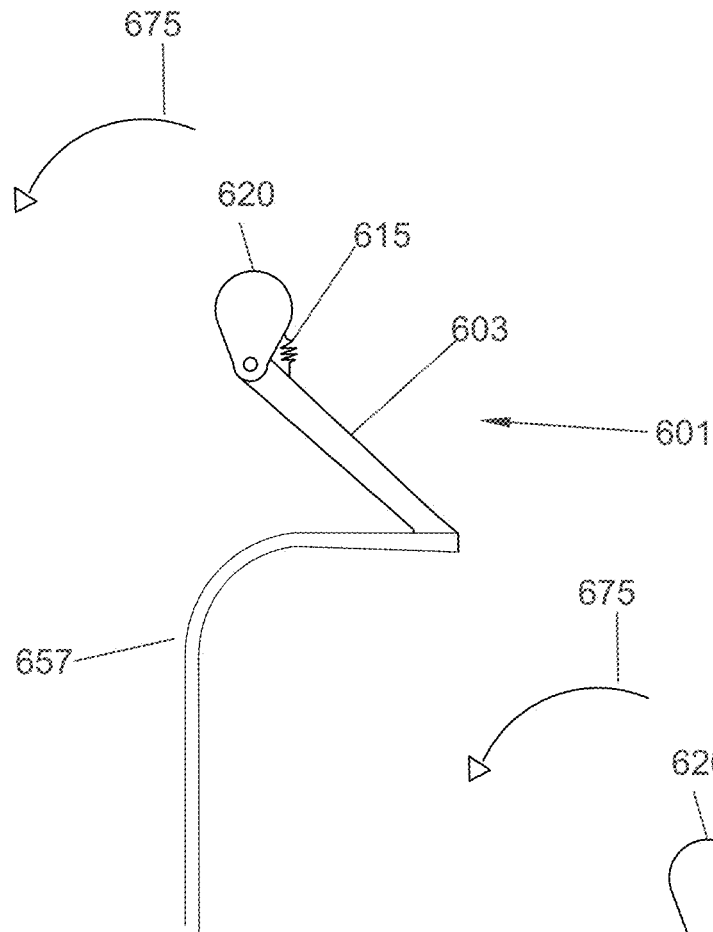
FIG. 7a shows an embodiment of a linkage rotationally coupled to head pillow.
Figure 7B:
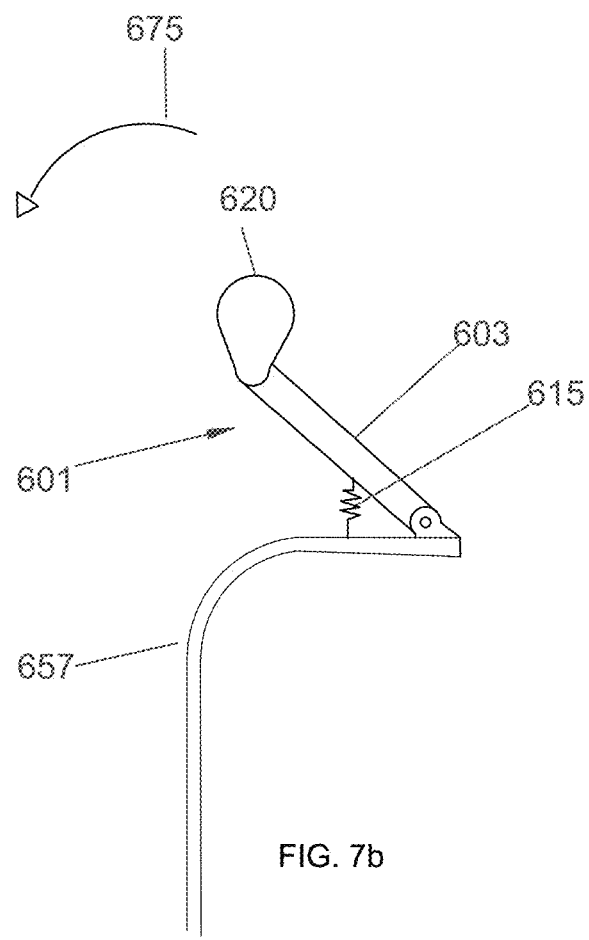
FIG. 7b shows an embodiment of a linkage rotationally coupled to torso frame.

In some embodiments, shown in FIG. 7*a*, linkage 603 is rotationally coupled to head pillow 620. In these embodiments, actuator 615 is coupled to head pillow 620 from its first end and to linkage 603 from its second end. In another embodiment, shown in FIG. 7*b* linkage 603 is rotationally coupled to torso frame 657. In this embodiment, actuator 615 is coupled to linkage 603 from its first end and to torso frame 657 from its second end.

In some embodiments, shown in FIG. 8*a*, FIG. 8*b*, and FIG. 8*c* linkage 603 comprises at least first segment 604 coupled to torso frame 657 and second segment 605 coupled to head pillow 620. In the embodiment of FIG. 8*a* linkage 603 comprises first segment 604 and second segment 605, wherein second segment 605 is rotationally coupled to first segment 604. First segment 604 may be configured to rotate relative to second segment 605 about first rotational axis 608. In the embodiment of FIG. 8*b* linkage 603 comprises first segment 604 and second segment 605, wherein second segment 605 is translationally coupled to first segment 604. First segment 604 may be configured to translate relative to second segment 605 so that head pillow 620 rotates relative to torso frame 657 about first rotational axis 608. In the embodiment of FIG. 8*c* linkage 603 comprises a plurality of rotating linkages configured to move head pillow 620 relative to torso frame 657. The plurality of rotating linkage may comprise a remote center mechanism 681 configured to rotate head pillow 620 relative to torso frame 657 about first rotational axis 608. Remote center mechanism 681 may comprise a double parallelogram linkage as shown in FIG. 8*c*, a spherical linkage, or similarly configured mechanism.

Figure 9A:
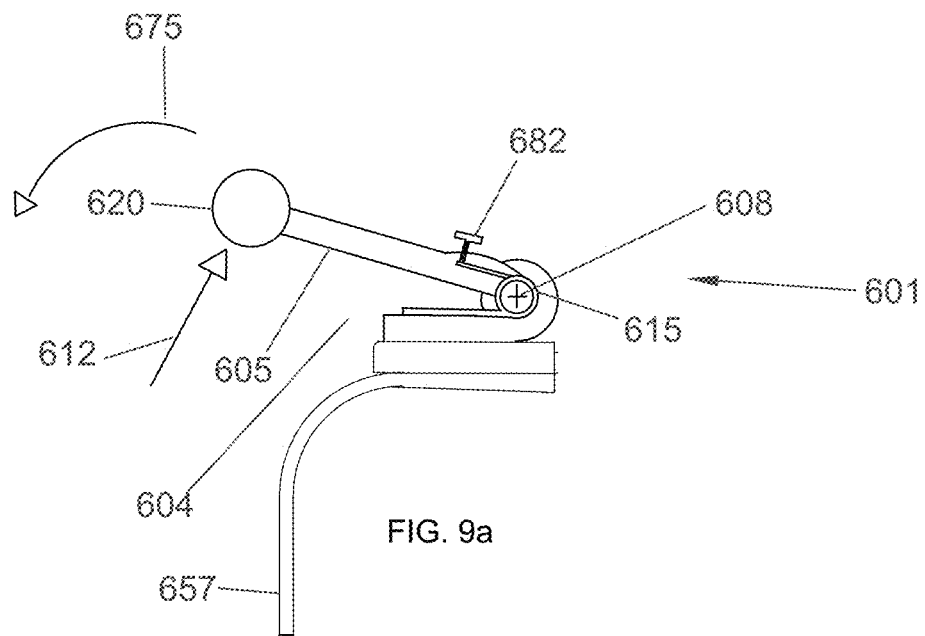
FIG. 9a shows an embodiment of a torsion spring actuator configured to generate a first torque amount.
Figure 9B:
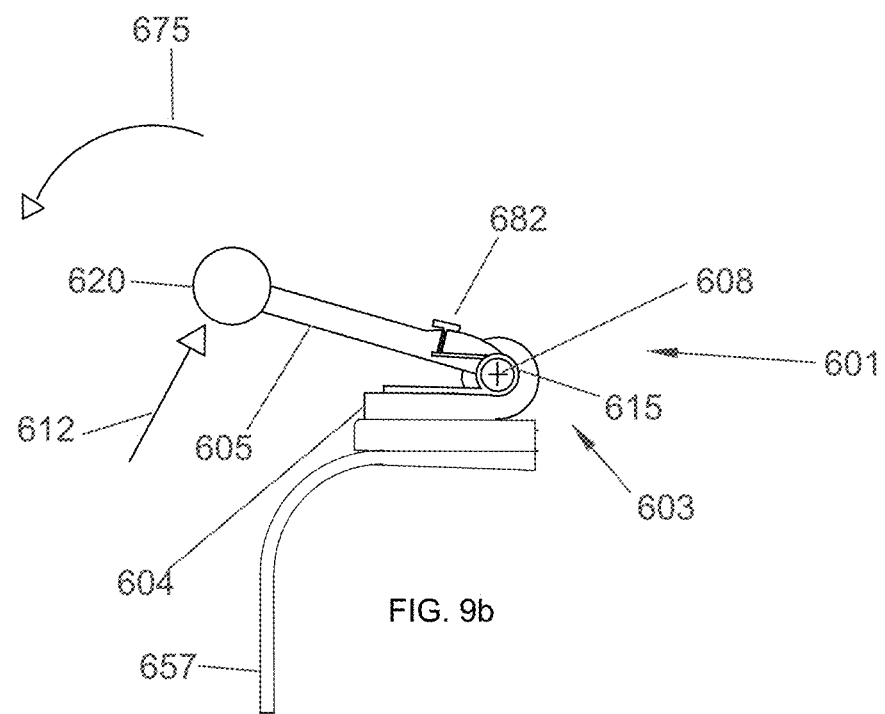
FIG. 9b shows an embodiment of a torsion spring actuator configured to generate a second torque amount.

Actuator 615 may act about any rotating, translating, or compliant joint within linkage 603. Actuator 615 may be selected from a set consisting of a linear spring, extension spring, compression spring, torsion spring, leaf spring, gas spring, coil spring, or disc spring. In the embodiments of FIG. 9*a* and FIG. 9*b* actuator 615 is coupled to first segment 604 of linkage 603 from its first end and to second segment 605 of linkage 603 from its second end. In some embodiments, actuator 615 is adjustably coupled to first segment 604 or second segment 605 of linkage 603 from its first end to adjust the level of supporting force 612 generated on to head pillow 620 and person's head 671. Neck supporting exoskeleton 600 may further comprise force adjustment element 682 configured to adjustably couple actuator 6:15 to first segment 604 or second segment 605 of linkage 603 from its first end to adjust the level of supporting force 612 generated on to head pillow 620 and person's had 671. In some embodiments, force adjustment element 682 alters the preload of actuator 615. In other embodiments force adjustment element 682 alters the mounting distance between actuator 615 and first segment 604 or second segment 605 relative to first rotational axis 608. It may be understood by one skilled in the art that the various types of actuator 615 and mounting configurations to linkage 603 can be applied to the rotating, translating, and remote center mechanism configurations of linkage 603 described above. In some embodiments, force adjustment element 682 comprises a screw.

In the embodiment of FIG. 9*a* and FIG. 9*b*, actuator 615 comprises a torsion spring coupled to first segment 604 of linkage 603 from its first end and to second segment 605 of linkage 603 from its second end, second segment 605 configured to rotate relative to first segment 604. Linkage 603 further comprises force adjustment element 682 adjustably coupled to second segment 605 and configured to contact actuator 615 to adjust the coupling between actuator 615 and second segment 605. In FIG. 9*a* force adjustment element 682 has positioned an end of actuator 615 in a first position relative to second segment 605 corresponding to a lower preload of actuator 615. In FIG. 9*b* force adjustment element 682 has positioned an end of actuator 615 in a second position relative to second segment 605 corresponding to a higher preload of actuator 615. The lower preload of actuator 615 will correspond to a lower supporting force 612 produced by neck supporting exoskeleton 600 compared to the higher preload of actuator 615.

Figure 10A:
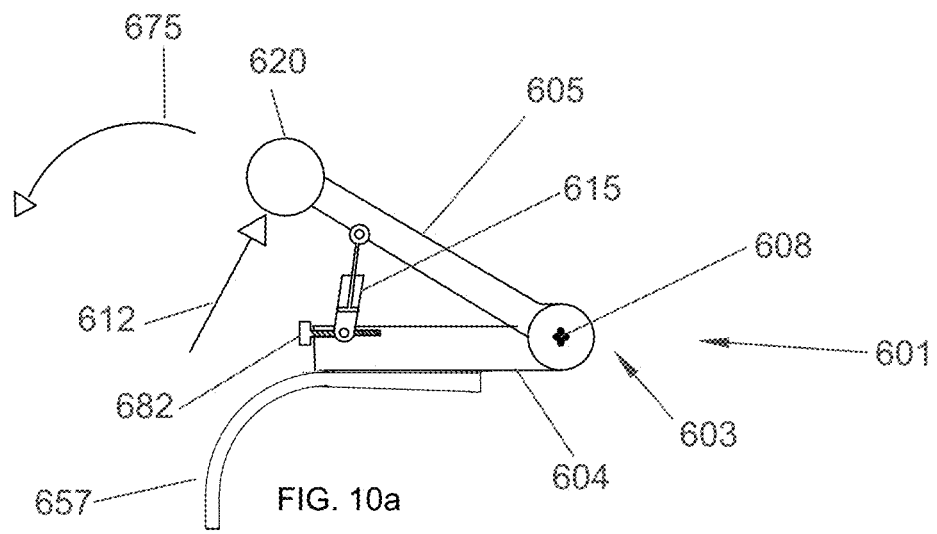
FIG. 10a shows an embodiment of a linear actuator configured to generate a first torque amount.
Figure 10B:
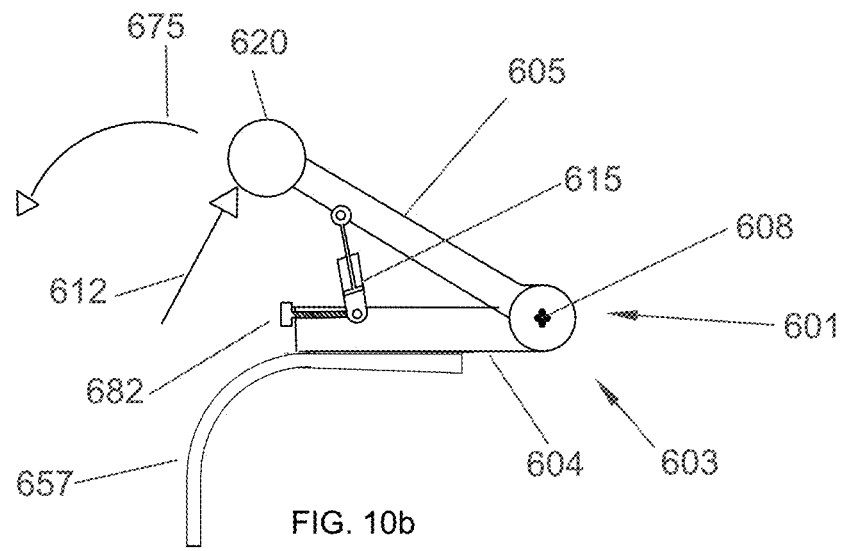
FIG. 10b shows an embodiment of a linear actuator configured to generate a second torque amount.

In the embodiment of FIG. 10*a* and FIG. 10*b* b, actuator 615 comprises a linear spring coupled to first segment 604 of linkage 603 from its first end and to second segment 605 or linkage 603 from its second end, second segment 605 configured to rotate relative to first segment 604. Linkage 603 further comprises force adjustment element 682 adjustably coupling one end of actuator 615 to first segment 604. In FIG. 10*a* force adjustment element 682 has positioned actuator 615 along first segment 604 to a greater distance from first rotational axis 608. In FIG. 10*b* force adjustment element 682 has positioned actuator 615 along first segment 604 to a lesser distance from first rotational axis 608. The greater distance of actuator 615 relative to first rotational axis 608 will correspond to a larger supporting force 612 produced by neck supporting exoskeleton 600 compared to the lesser distance. It may be understood by one skilled in the art force adjustment element 682 may translate or rotate relative to first segment 604 or second segment 605 to adjust the position of actuator 615.

In another embodiment of neck supporting exoskeleton 600 actuator 615 comprises a leaf spring. Actuator 615 may act about any rotating or translating joint within linkage 603. In another embodiment of neck supporting exoskeleton 600 actuator 615 comprises an electric motor or linear actuator.

Figure 11A:
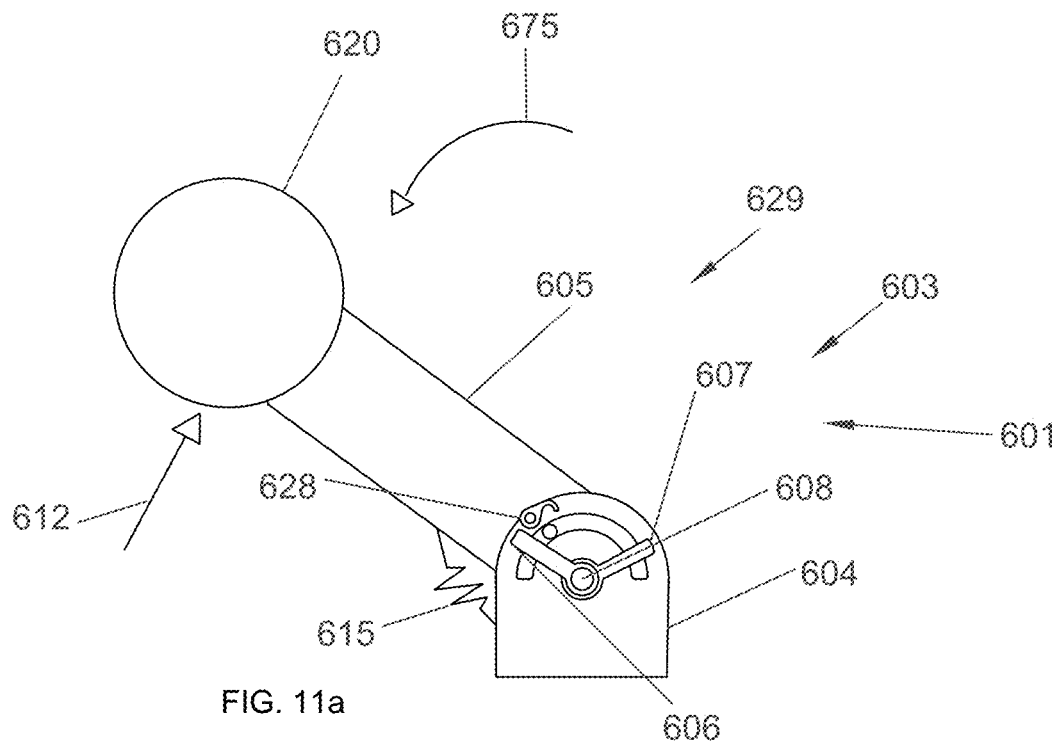
FIG. 11a shows a neck linkage comprising a flexion hard stop, an extension hard stop, and a stow lock in an un-stowed position.
Figure 11B:
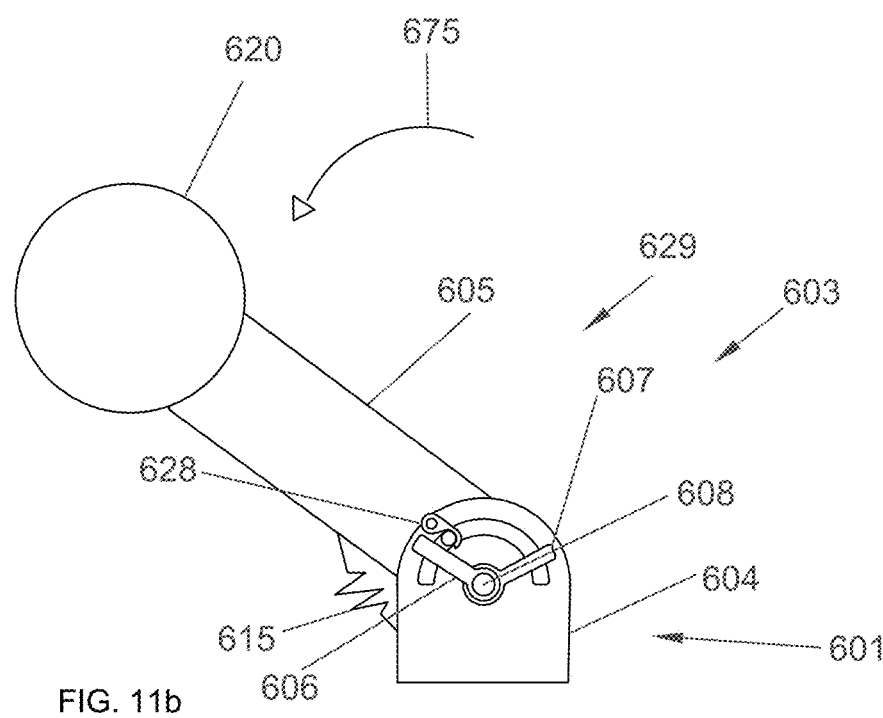
FIG. 11b shows a neck linkage comprising a flexion hard stop, an extension hard stop, and a stow lock in a stowed position.
Figure 12:
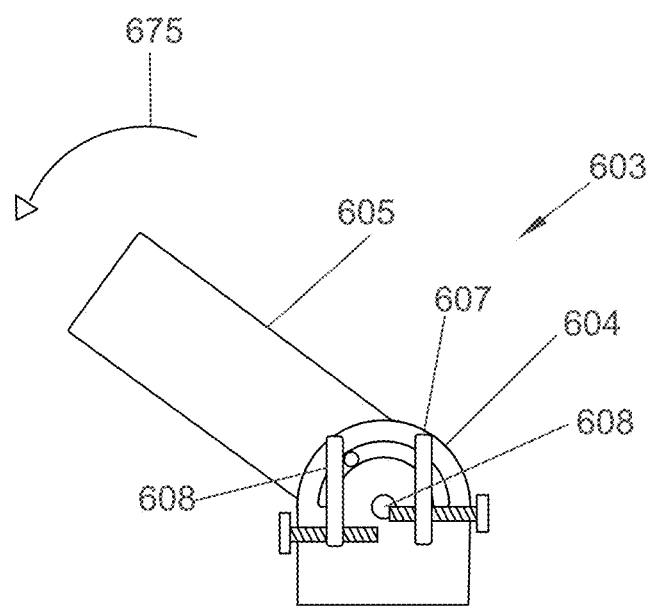
FIG. 12 shows a neck linkage with an alternative embodiment of a flexion hard stop and extension hard stop.
Figures 13A, 13B:
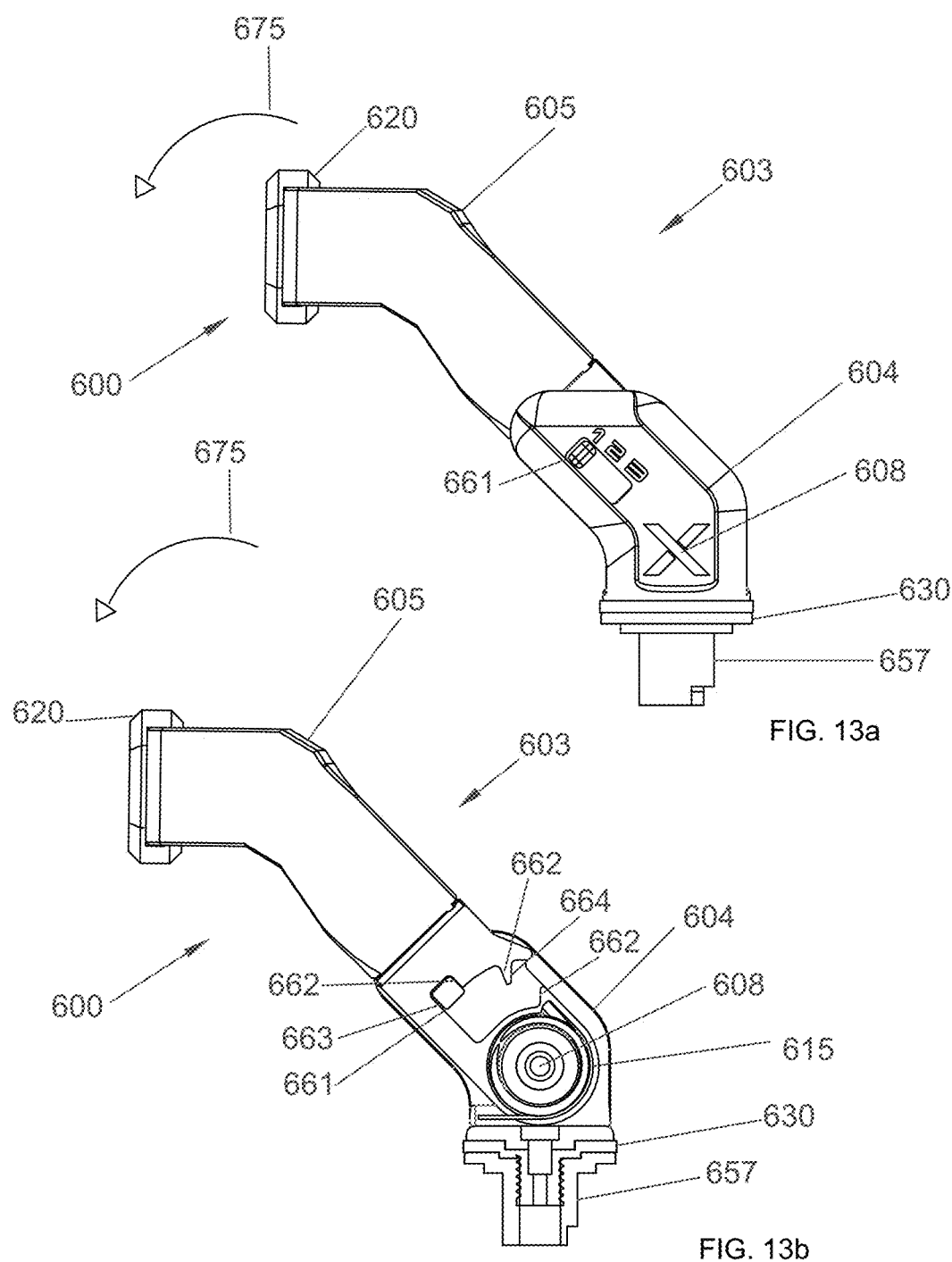
FIG. 13a shows a side view of a neck linkage with a hard stop switch in a first position.
FIG. 13b shows a section view of a neck linkage with a hard stop switch in a first position.

FIG. 11*a* through FIG. 17 show embodiments of neck supporting exoskeleton 600 wherein linkage 603 prevents flexion motion between head pillow 620 and torso frame 657 in sagittal plane 674 of person 670. In some embodiments, flexion motion between head pillow 620 and torso frame 657 is prevented after engagement angle 611. FIG. 11*a*, FIG. 11*b*, and FIG. 12 show an embodiment of neck supporting exoskeleton 600 wherein linkage 603 comprises flexion hard stop 607 adjustably coupled to linkage 603 and configured to prevent flexion motion between head pillow 620 and torso frame 657 in sagittal plane 674 of person 670 to adjust engagement angle 611. In some embodiments, flexion hard stop 607 is adjustably coupled to first segment 604 of linkage 603. With increasing engagement angle 611, the free range of motion expands but the range of motion where neck supporting exoskeleton 600 supports the weight of person's head 671 is reduced. In some embodiments, engagement angle 611 may be tuned by flexion hard stop 607 to allow for minimal inhibition or maximum support. In some embodiments, flexion hard stop 607 is not adjustable relative to linkage 603 and engagement angle 611 or engagement position is fixed, Flexion hard stop 607 may adjust in a continuous range, such as with a screw or clamp, for a continuous range of engagement angle 611. Alternatively, flexion hard stop 607 may adjust in a discrete range with multiple fixed positions, such as with an indexing switch, to create multiple fixed values of engagement angle 611. Actuator 615 may preload motion of first segment 604 relative to second segment 605 at the position of flexion hard stop 607. In the embodiments of FIG. 11a and FIG. 11b linkage 603 comprises first segment 604 and second segment 605 and flexion hard stop 607 is coupled to first segment 604 to prevent motion of first segment 604 relative to second segment 605. Similarly flexion hard stop 607 may be coupled to second segment 605 to prevent relative motion of second segment 605 relative to first segment 604. In the embodiment of FIG. 11a and FIG. 11b flexion hard stop 607 is rotationally coupled to first segment 604, In the embodiment of FIG. 12 flexion hard stop 607 is translationally coupled to first segment 604. In other embodiments not shown linkage 603 comprises flexion hard stop 607 configured to prevent motion of linkage 603 relative to head pillow 620. In yet another embodiment, linkage 603 comprises flexion hard stop 607 configured to prevent motion of linkage 603 relative to torso frame 657. Whether attached to linkage 603, head pillow 620, or torso frame 657, flexion hard stop 607 may create a similar behavior as shown and described in FIG. 4a and FIG. 4b when neck supporting exoskeleton 600 is worn by person 670. It may be understood by one skilled in the art that many mechanisms may be utilized to adjust and fix the location of flexion hard stop 607 relative to linkage 603 such as screws, clamps, indexing switches, or similar means. It may also be understood by one skilled in the art that flexion hard stop 607 may be utilized to prevent rotation or translation motion between first segment 604 and second segment 605 of linkage 603, and said rotation or translation may occur about first rotational axis 608.

FIG. 11a through FIG. 17 show embodiments of neck supporting exoskeleton 600 wherein linkage 603 prevents extension motion 675 between head pillow 620 and torso frame 657 in sagittal plane 674 of person 670. In some embodiments, extension motion 675 between head pillow 620 and torso frame 657 is prevented after resting angle 619. FIG. 11a, FIG. 11b, and FIG. 12 show an embodiment of neck supporting exoskeleton 600 wherein linkage 603 comprises extension hard stop 606 adjustably coupled to linkage 603 and configured to prevent extension motion 675 between head pillow 620 and torso frame 657 in sagittal plane 674 of person 670 to adjust resting angle 619. In some embodiments, extension hard stop 606 is adjustably coupled to first segment 604 of linkage 603. Extension hard stop 606 may adjust in a continuous range, such as with a screw or clamp, for a continuous range or resting angle 619. Alternatively, extension hard stop 606 may adjust in a discrete range with multiple fixed positions, such as with an indexing switch, to create multiple fixed values of resting angle 619. In some embodiments, extension hard stop 606 is not adjustable relative to linkage 603 and resting angle 619 or resting position is fixed. At resting angle 619 head pillow 620 is prevented from moving in extension motion 675 relative to torso frame 657 and may be used to support the full weight of person's head 671. In the embodiments of FIG. 11a, FIG. 11b, and FIG. 12 linkage 603 comprises first segment 604 and second segment 605 and extension hard stop 606 is coupled to first segment 604 to prevent motion of first segment 604 relative to second segment 605. Similarly flexion hard stop 607 may be coupled to second segment 605 to prevent the relative motion of second segment 605 relative to first segment 604, In the embodiment of FIG. 11a and FIG. 11b extension hard stop 606 is rotationally coupled to first segment 604. In the embodiment of FIG. 12 extension hard stop 606 is translationally coupled to first segment 604. In other embodiments not shown linkage 603 comprises extension hard stop 606 configured to prevent the motion of linkage 603 relative to head pillow 620. In yet another embodiment linkage 603 comprises extension hard stop 606 configured to prevent the motion of linkage 603 relative to torso frame 657. Whether attached to linkage 603, head pillow 620, or torso frame 657, extension hard stop 606 may create a similar behavior as shown and described FIG. 5a or FIG. 5b when neck supporting exoskeleton 600 is worn by person 670. It may be understood by one skilled in the art that many mechanisms may be utilized to adjust and fix the location of extension hard stop 606 relative to linkage 603 such as screws, clamps, indexing switches, or similar means. It may also be understood by one skilled in the art that extension hard stop 606 may be utilized to prevent rotation or translation motion between first segment 604 and second segment 605 of linkage 603, and said rotation or translation may occur about first rotational axis 608.

In some embodiments, of neck supporting exoskeleton, shown in FIG. 11a and FIG. 11b, linkage 603 further comprises stow lock 628 configured to prevent the flexion motion of head pillow 620 relative to torso frame 657 at stow position 629. stow position 629 corresponds to the position of head pillow 620 relative to torso frame 657 that stow lock 628 is configured to engage in. Stow lock 628 may be configured to be moved between at least a first position and a second position. When stow lock 268 is in a first position and head pillow 620 is at stow position 629 relative to torso frame 657, as shown in FIG. 11a, linkage 603 does not prevent head pillow 620 from moving relative to torso frame 657. In this first position of stow lock 268, actuator 615 causes linkage 603 to apply supporting force 612 to head pillow 620 and neck supporting exoskeleton 600 will support person's head 671 when worn by person 600 as in FIG. 6a. When stow lock 628 is in a second position and head pillow 620 is at stow position 629 relative to torso frame 657, linkage 603 prevents head pillow 620 from moving relative to torso frame 657 in flexion motion thereby stowing head pillow 620 out of the person's workspace when neck supporting exoskeleton 600 is not in use. In this second position of stow lock 268, as shown in FIG. 11b, linkage 603 does not apply supporting force 612 to head pillow 620 and neck supporting exoskeleton 600 will not support the person's head 671 when worn by person 670, as in FIG. fib. Furthermore, when stow lock 628 is in a second position and head pillow 620 is in stow position 629 relative to torso frame 657, person's head 671 will separate from head pillow 620 as person's neck 673 moves in flexion motion as shown in FIG. 6c. Stow lock 628 may act between a rotational or translational coupling between first segment 604 of linkage 603 and second segment 605 of linkage 603. Stow lock 628 may also prevent further extension motion 675 of head pillow 620 relative to torso frame 657 and can be used so that neck supporting exoskeleton 600 will support the full weight of person's head 671 at a particular neck extension angle 618 and while also not engaging with person's head 671 until that same neck extension angle 618. Stow lock 628 may be coupled to first segment 604 to prevent the motion of first segment 604 relative to second segment 605 of linkage 603. Alternatively, stow lock 628 may be coupled to linkage 603 or head pillow 620 to prevent the relative motion of linkage 603 relative to head pillow 620. Stow lock 628 may also be coupled to linkage 603 or torso frame 657 to prevent the relative motion of linkage 603 relative to torso frame 657. Stow lock 628 may comprise a first profile coupled to first segment 604 of linkage 603 and a second profile coupled to second segment 605 of linkage 603. Stow lock 628 may comprise a rotating hook, magnetic clasp, buckle, screw, latch, switch or similar mechanism known to one skilled in the art.

FIG. 13a through FIG. 17 show an embodiment of neck supporting exoskeleton 600 wherein linkage 603 further comprises first segment 604, hard stop switch 661 coupled to first segment 604 and configured to be moved between at least a first position and a second position, and second segment 605 rotationally coupled to first segment 604. Second segment 605 comprises a profile wherein the contact between hard stop switch 661 and the profile restricts the movement of second segment 605 relative to first segment 604. It may be understood by one skilled in the art that hard stop switch 661 may be configured to function similarly if hard stop switch 661 is located on second segment 605 and profile located on first segment 604, if first segment 604 translates relative to second segment 605, or to function between linkage 603 head pillow 620 or between linkage 603 torso frame 657. Depending on the configuration of the profile, hard stop switch 661 may function as one of or a combination of flexion hard stop 607, extension hard stop 606, or stow lock 628. Accordingly, second segment 605 profile is configured to contact hard stop switch 661 to prevent the motion of first segment 604 relative to second segment 605, and may be selected from a set consisting of: 1) extension hard stop profile 662 configured to engage hard stop switch 661 to prevent second segment 605 from rotating relative to first segment 604 in extension motion 675, extension hard stop profile 662 defining a resting angle 619, 2) flexion hard stop profile 663 configured to engage hard stop switch 661 to prevent second segment 605 from rotating relative to first segment 604 in a flexion motion, flexion hard stop profile 663 defining engagement angle 611, and 3) stow profile 664 configured to engage hard stop switch 661 to prevent second segment 605 from rotating relative to first segment 604 in a flexion motion at stow position 629 to stow head pillow 620 out of the person's workspace when neck supporting exoskeleton 600 is not in use. Hard stop switch 661 may be rotationally or translationally coupled to first segment 604 in a continuous or discreet manner by means of a screw, indexing switch, or similar mechanism.

FIG. 11a shows a side view and FIG. 11b shows a section view of neck supporting exoskeleton 600 comprising hard stop switch 661 in a first position. At the first position of hard stop switch 661, hard stop switch 661 engages both first position of flexion hard stop profile 663 at engagement angle 611 and first position of extension hard stop profile 662 at a first position of resting angle 619 equal to engagement angle 611 and prevents second segment 605 from moving in extension motion 675 or flexion motion relative to first segment 604.

Figure 14A:
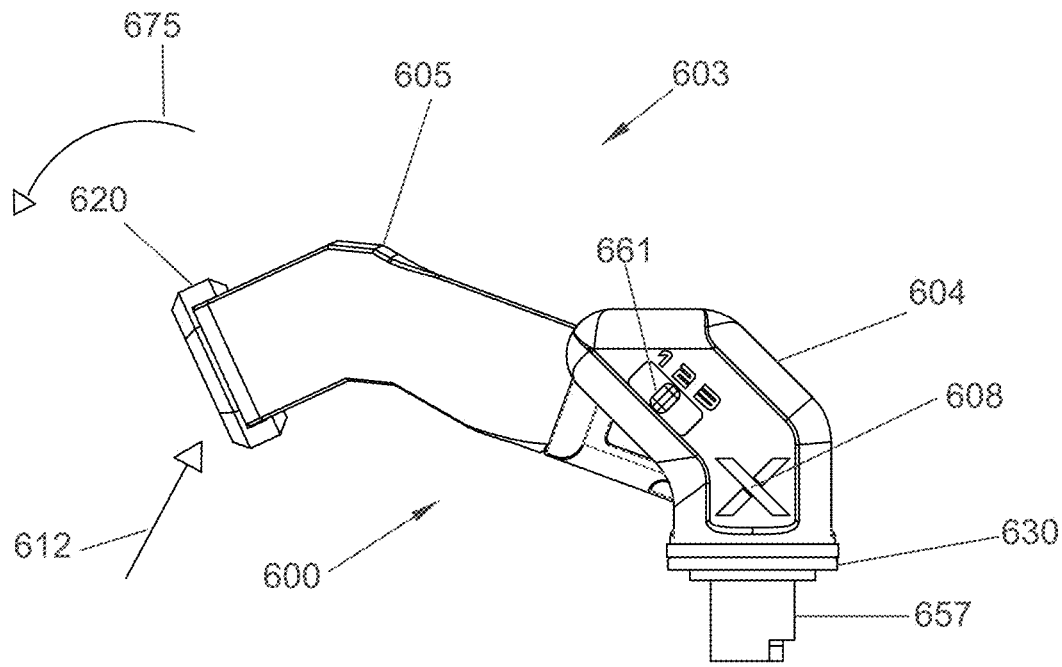
FIG. 14a shows a side view of a neck linkage with a hard stop switch in a second position.
Figure 14B:
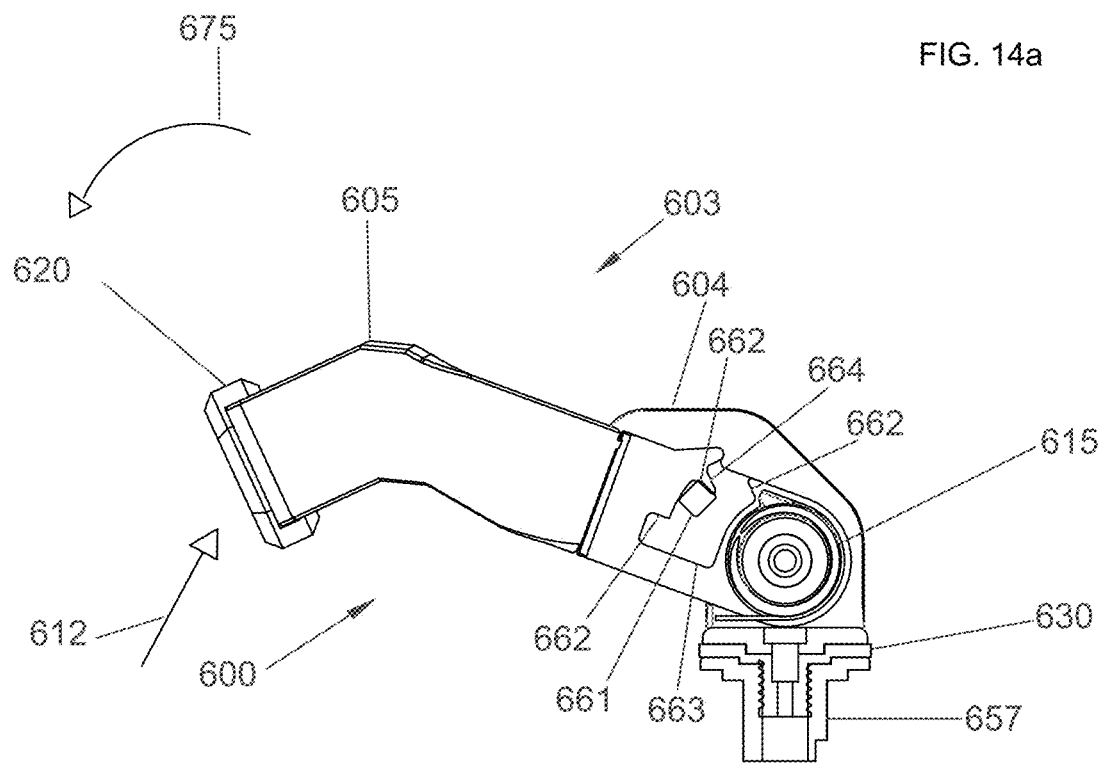
FIG. 14b shows a section view of a neck linkage with a hard stop switch in a second position.

FIG. 14a shows a side view and FIG. 14b shows a section view of neck supporting exoskeleton 600 comprising hard stop switch 661 in a second position. At the second position of hard stop switch 661, hard stop switch 661 engages first position of flexion hard stop profile 663 at engagement angle 611 and second position of extension hard stop profile 662 at second position of resting angle 619 and neck supporting exoskeleton 600 provides supporting force 612 to person's head 671 for neck extension angles 618 between the engagement angle 611 and second position of resting angle 619.

Figure 15A:
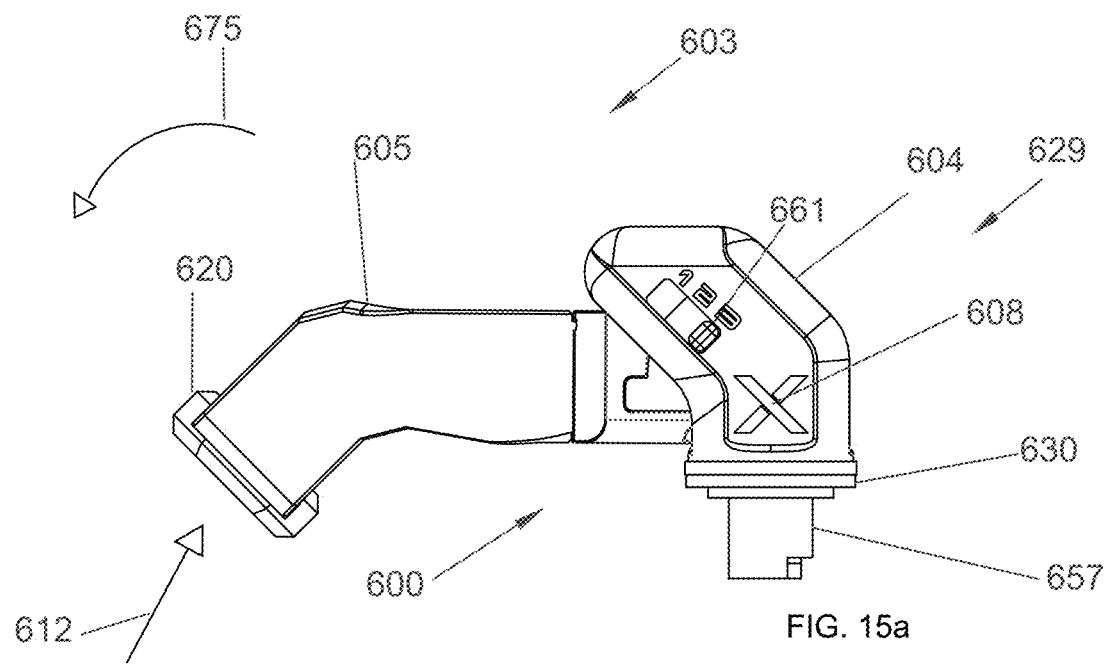
FIG. 15a shows a side view of a neck linkage with a hard stop switch in a third position.
Figure 15B:
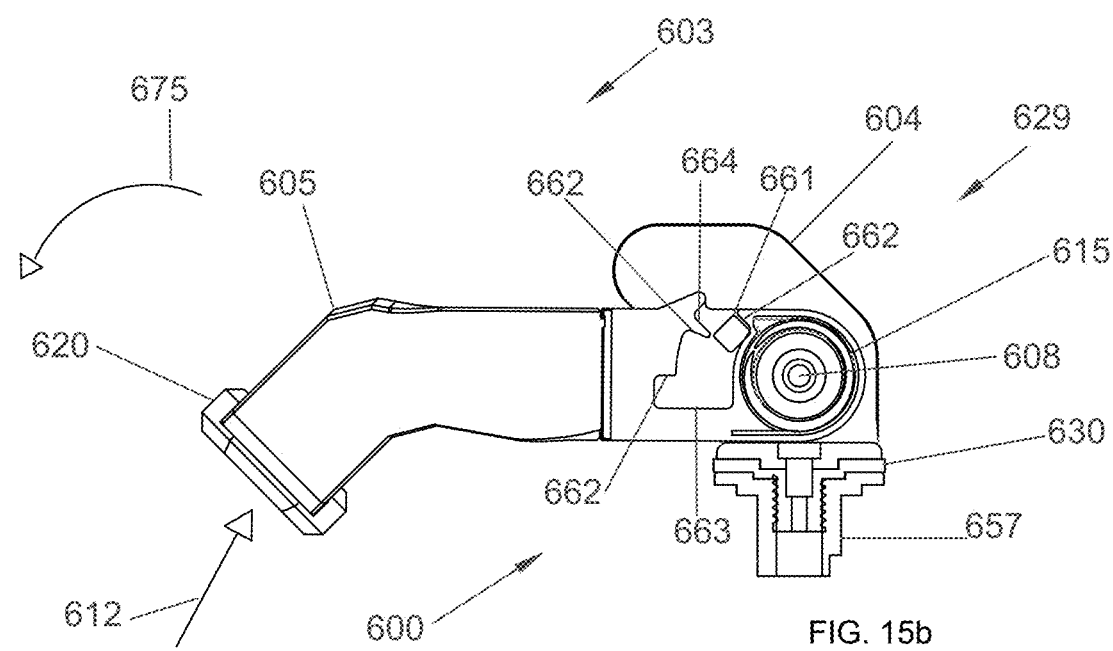
FIG. 15b shows a section view of a neck linkage with a hard stop switch in a third position.

FIG. 15a shows a side view and FIG. 15b shows a section view of neck supporting exoskeleton 600 comprising hard stop switch 661 in a third position. At the third position of hard stop switch 661 first segment 604 may be oriented in a stow position 629 relative to second segment 605. At the third position of the hard stop switch 661, hard stop switch 661 engages first position of flexion hard stop 663 profile at engagement angle 611 and third position of extension hard stop profile 662 at third position of resting angle 619 and neck supporting exoskeleton 600 provides supporting force 612 to person's head 671 for neck extension angles 618 between engagement angle 611 and third position resting angle 619.

Figure 16A:
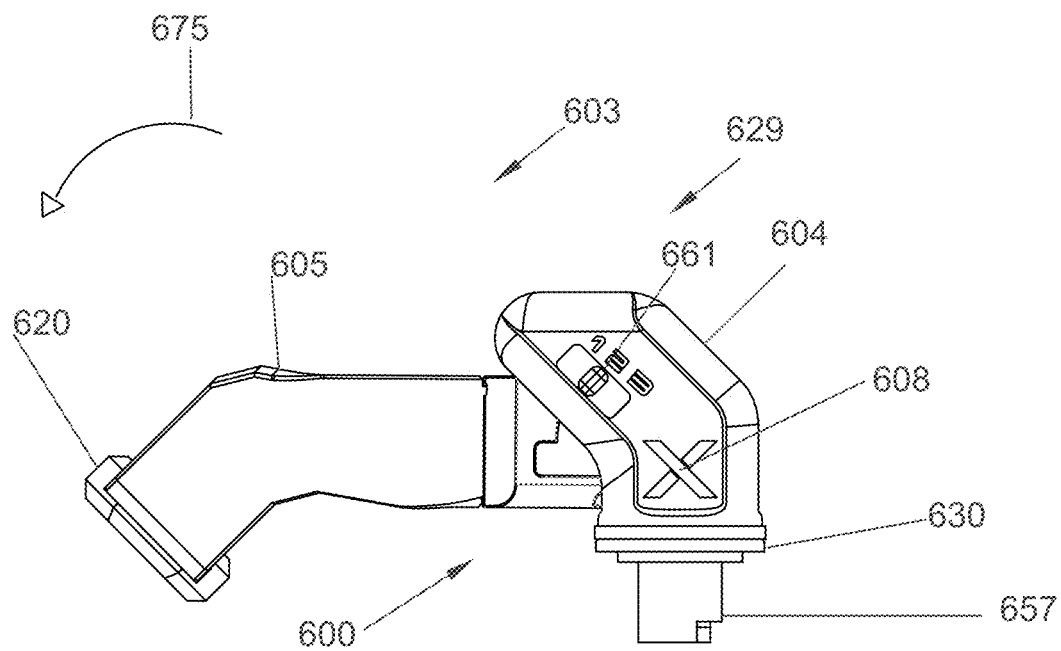
FIG. 16a shows a side view of a neck linkage with a hard stop switch in a stow position.
Figure 16B:
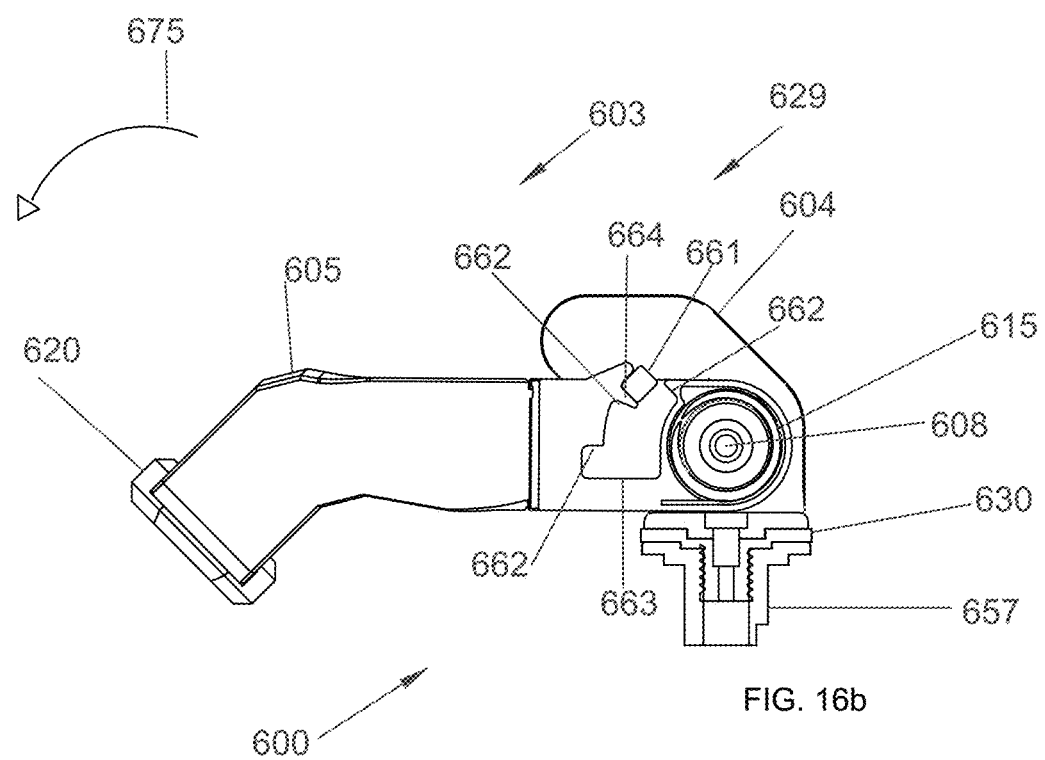
FIG. 16b shows a section view of a neck linkage with a hard stop switch in a stow position.

FIG. 16a shows a side view and FIG. 16b shows a section view of neck supporting exoskeleton 600 comprising hard stop switch 661 in a second position when first segment 604 is oriented in stow position 629 relative to second segment 605. I-lard stop switch 661 may be configured to engage stow profile 664 at stow position 629 causing head pillow 620 to be stowed out of the person's workspace. In stow position 629 hard stop switch 661 prevents flexion motion of head pillow 620 relative to torso frame 657 or first segment 604 relative to second segment 605.

Figure 17:
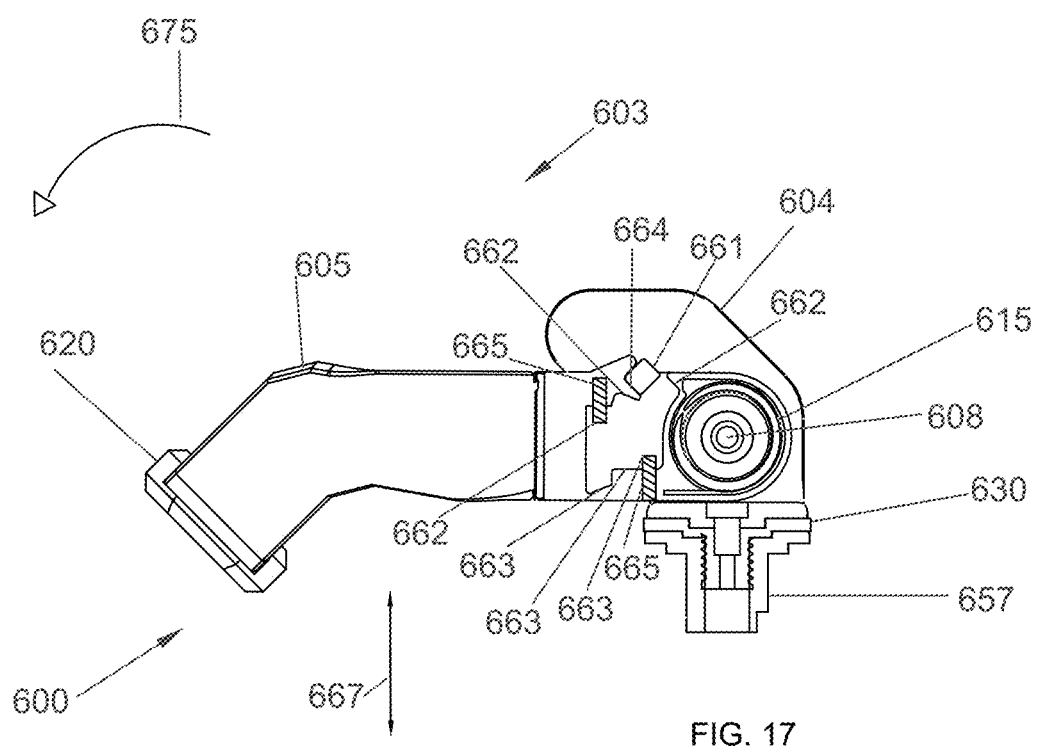
FIG. 17 shows a section view of a neck linkage with a hard stop switch and adjustable hard stop profiles.

FIG. 17 shows a section view of neck supporting exoskeleton 600 further comprising profile adjustment element 665 translationally coupled to second segment 605 to change the position of flexion hard stop profile 663 or extension hard stop profile 662. Profile adjustment element 665 may comprise a set screw or similar mechanism to allow a translation or rotation motion that will hold a position when loaded by hard stop switch 661. It may also be observed from FIG. 17 that the profiles of second segment 605 may be modified in many ways to create different responses of linkage 603 in response to the position of hard stop switch 661. Such responses may include having the same or differing engagement angles 611 or engagement positions for each position of hard stop switch 661, having the same or differing resting angles 619 or resting positions for each position of hard stop switch 661, or having the same or differing stow positions 629 for each position of hard stop switch 661.

To accommodate twisting and lateral flexion of person's neck 673, alternative degrees of freedom may be added to linkage 603. In embodiments where contact between person's head 671 and head pillow 620 does not occur until engagement angle 611, these motions will be uninhibited if neck extension angle 618 is less than engagement angle 611. When neck extension angle 618 is greater than engagement angle 611 and person's head 671 is in contact with head pillow 620, additional degrees of freedom for lateral flexion and twisting will minimize relative motion between person's head 671 and head pillow 620. Because these degrees of freedom are orthogonal to extension motion about which resilient structure 601 resists motion of head pillow 620 relative to torso frame 657, they may be added with no influence to flexion-extension support torque.

Figure 18:
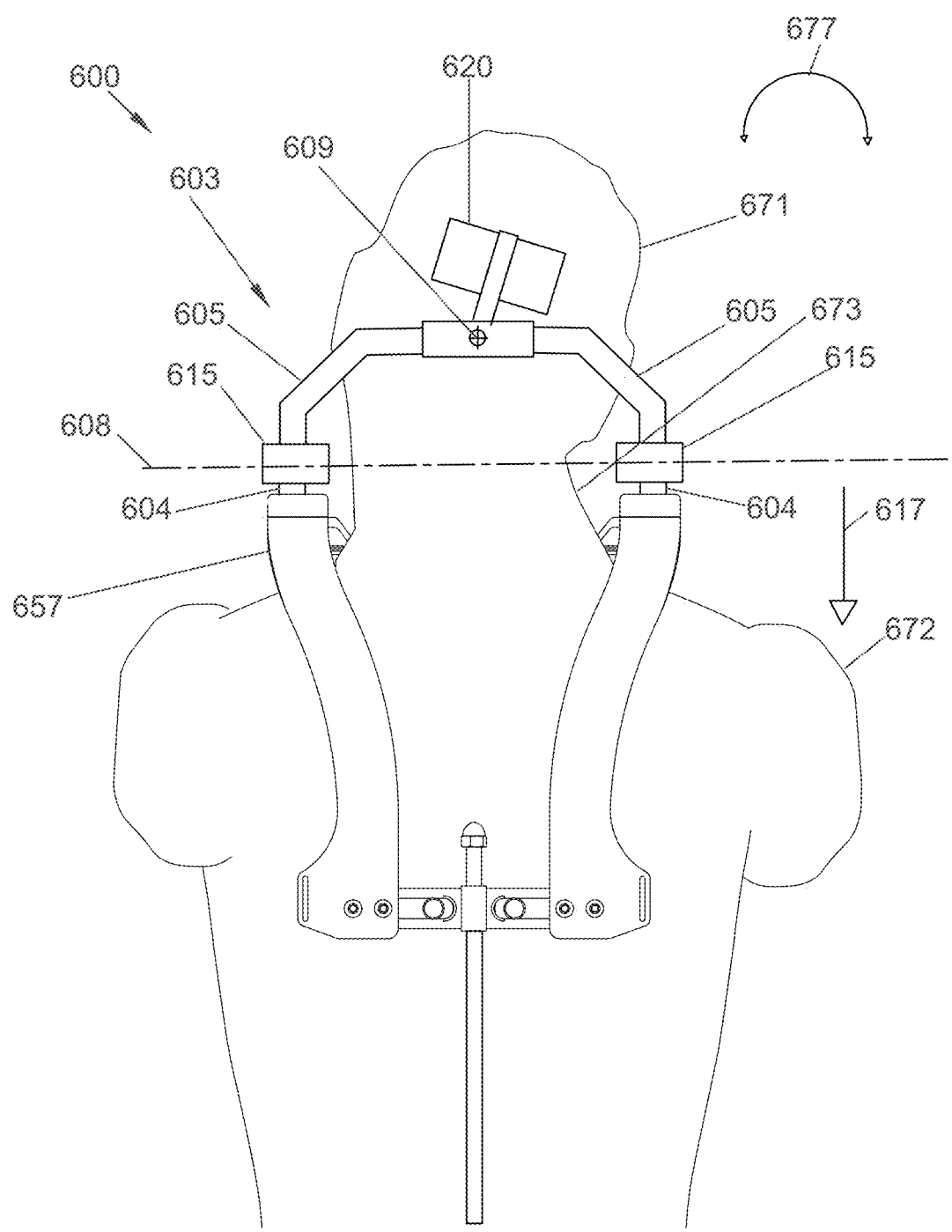
FIG. 18 shows a rear view of a neck supporting exoskeleton configured to rotate about a first rotational axis and a second rotational axis.
Figure 19:
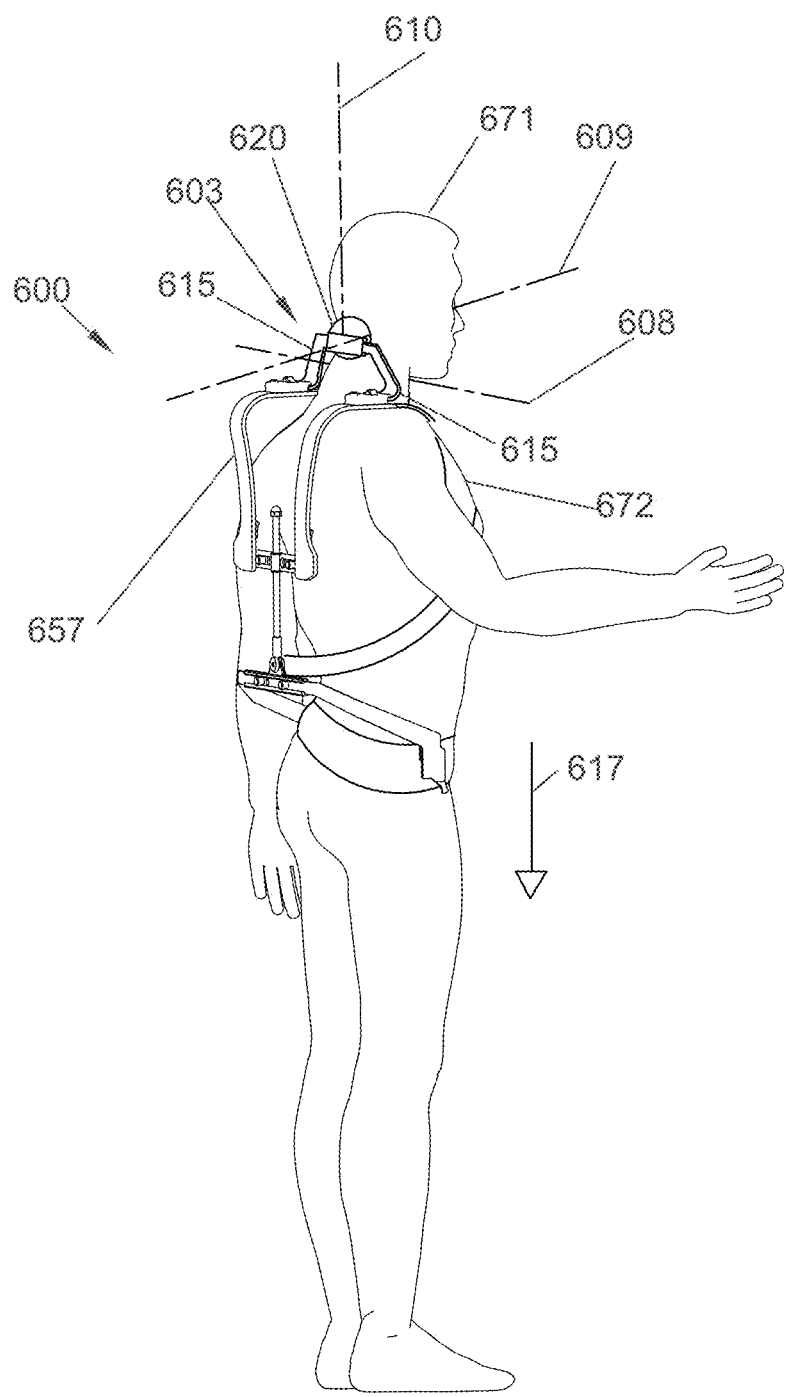
FIG. 19 shows a perspective view of a neck supporting exoskeleton configured to rotate about a first rotational axis, a second rotational axis, and a third rotational axis.

FIG. 18 shows an embodiment of neck supporting exoskeleton 500 wherein linkage 603 is configured to rotate head pillow 620 relative to torso frame 657 about second rotational axis 609 orthogonal to first rotational axis 608. In some embodiments, second rotational axis 609 passes approximately through person's neck 673 or person's head 671 to allow motion of person's head 671 relative to person's torso 672 in a lateral flexion direction 677. In some embodiments, second rotational axis 609 is orthogonal to gravity line 617. The rotation of head pillow 620 relative to torso frame 657 about second rotational axis 609 may be free, lockable, or spring loaded to a centered position, or spring loaded and used in conjunction with head pillow 620 that contacts the sides of person's head 671 to provide additional support to person's head 671 during motions in lateral flexion direction 677.

FIG. 18 shows a rear perspective view of an embodiment of neck supporting exoskeleton 600 wherein linkage 603 rotates head pillow 620 relative to torso frame 657 about third rotational axis 610 orthogonal to both first rotational axis 608 and second rotational axis 609. In some embodiments, third rotational axis 610 is parallel to gravity line 617 when person 670 is standing upright. Third rotational axis 610 may similarly be free, lockable, or spring loaded to a centered position.

In some embodiments, neck supporting exoskeleton 600 further comprises positioning mechanism 683 configured to adjust the location of head pillow 620 relative to torso frame 657. Positioning mechanism 683 may be a part of resilient structure 601, linkage 603, head pillow 620, torso frame 657, or be coupled between any two of the previously mentioned structures. Positioning mechanism 683 may be configured to adjust the location of resilient structure 601 relative to torso frame 657 or the position of resilient structure 601 relative to head pillow 620. In some embodiments, positioning mechanism 683 may be configured to adjust the size of neck supporting exoskeleton 600 to fit different sizes of person 670. Positioning mechanism 683 may adjust for different sizes of person 670 by adjusting the location of person's head 671 where head pillow 620 makes contact. In other embodiments positioning mechanism 683 may also be used to align first rotational axis 608 with person's neck 673. Still in other embodiments positioning mechanism 683 may be used to adjust the engagement angle 611 when person's head 671 contacts the head pillow 620.

Figure 20A:
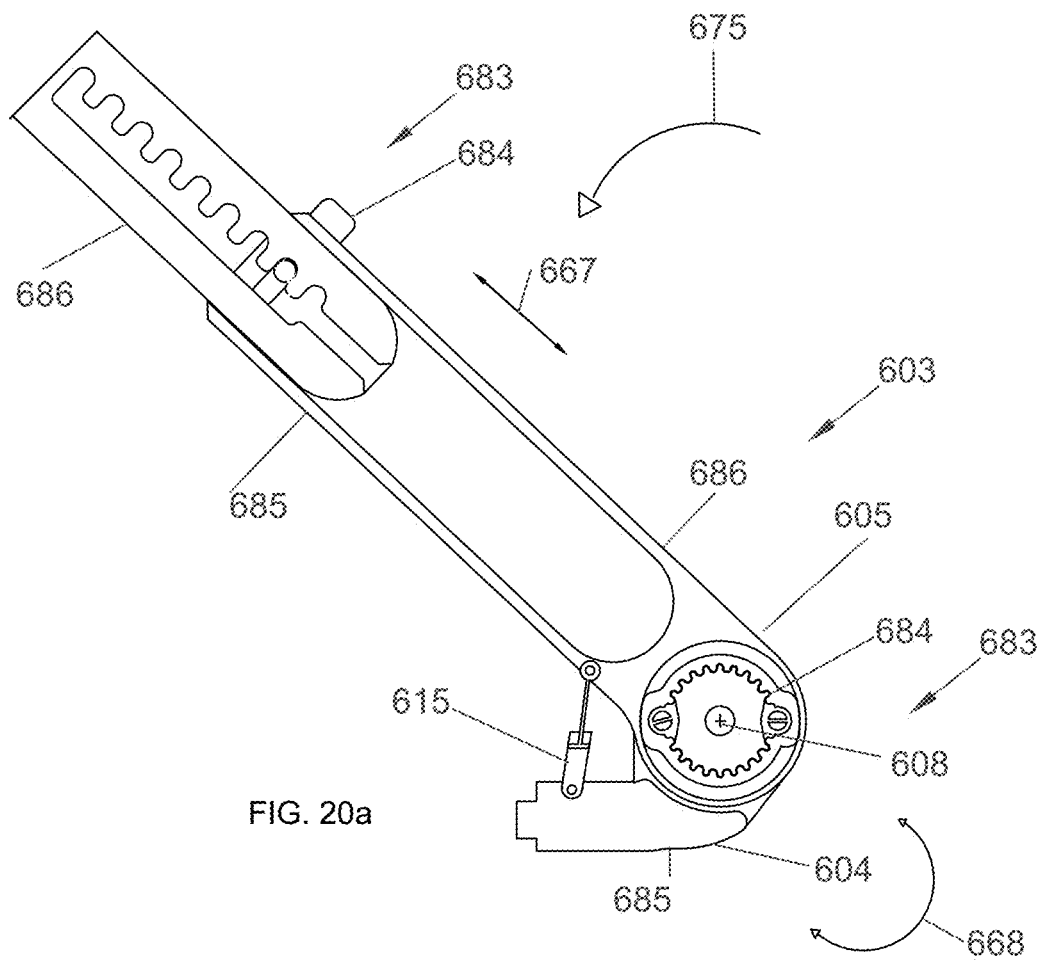
FIG. 20a shows a side view of a rotary and linear positioning mechanism.

FIG. 20a shows embodiments of positioning mechanism 683 configured to adjust in linear adjustment direction 667 or rotational adjustment direction 668. To adjust in linear adjustment direction 667 positioning mechanism 683 may comprise base link 685, adjustment link 686 translationally coupled to base link 685, and position locking element 684 configured to move between at least a first position and a second position. When position locking element 684 is in its first position, adjustment link 686 can freely translate relative to base link 685. When position locking element 684 is in its second position, adjustment link 686 is fixed relative to base link 685. In some embodiments, position locking element 684 is spring loaded into a second position. Position locking element 684 may be coupled to base link 685 or adjustment link 686. A portion or profile of position locking element 684 may then be configured to engage with a profile of either base link 685 or adjustment link 686 that position locking element 684 is not coupled to. In the embodiment of FIG. 20a position locking element 684 is moveably coupled to base link 685 and is configured to engage with a series of profiles in adjustment link 686 corresponding to discrete values of adjustment along linear adjustment direction 667.

Figure 20B:
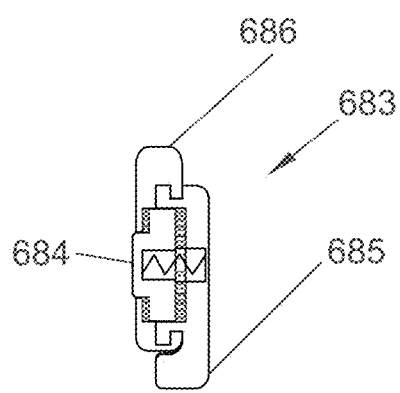
FIG. 20b shows a section view of a rotary positioning mechanism in a locked state.
Figure 20C:
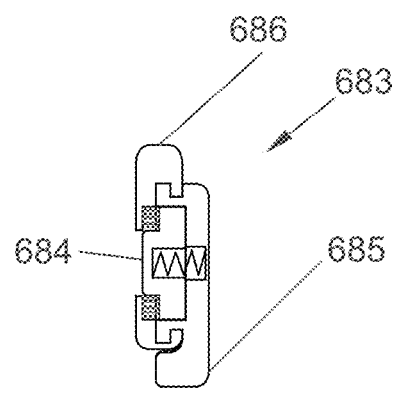
FIG. 20c shows section view of a rotary positioning mechanism in an unlocked state.

FIG. 20a also shows an embodiment of positioning mechanism 683 configured to adjust in rotational adjustment direction 668. To adjust in rotational adjustment direction 668 positioning mechanism 683 may comprise base link 685, adjustment link 686 rotationally coupled to base link 685, and position locking element 684 configured to move between at least a first position and a second position. When position locking element 684 is in its first position, adjustment link 686 can freely rotate relative to base link 685. When position locking element 684 is in its second position, adjustment link 686 is fixed relative to base link 685. In some embodiments, position locking element 684 is spring loaded into a second position. Position locking element 684 may be coupled to base link 685 or adjustment link 686. A portion or profile of position locking element 684 may then be configured to engage with a profile of either base link 685 or adjustment link 686 that position locking element 684 is not coupled to. In the embodiment of FIG. 20a position locking element is moveably coupled to base link 685 and is configured to engage with a series of gear tooth profiles in adjustment link 686 corresponding to discrete values of adjustment along rotational adjustment direction 668. FIG. 20b shows a section view of positioning mechanism 683 of FIG. 20a configured to adjust in rotational adjustment direction 668 when position locking element 684 is in its second position. In its second position, the gear tooth profiles of position locking element 684 contact mating profiles in both base link 685 and adjustment link 686, thereby preventing adjustment link 686 from rotating relative to base link 685. Position locking element 684 is spring-loaded into this second position. FIG. 20b shows a section view of positioning mechanism 683 of FIG. 20a configured to adjust in rotational adjustment direction 668 when position locking element 684 is in its first position. In its first position, the gear tooth profiles of position locking element 684 contact only the mating profiles in base link 685, allowing adjustment link 686 to rotate freely relative to base link 685. When position locking element 684 is released, the gear tooth profiles of position locking element 684 will automatically engage with the mating profile of adjustment link 686 once the closest discrete position is reached.

In some embodiments, shown in FIG. 20a, neck supporting exoskeleton 600 may comprise multiple positioning mechanisms 683 and adjustment link 686 of first petitioning mechanism 683 may be base link 685 of second positioning mechanism 683 in series with first positioning mechanism 683. In other embodiments, also shown in FIG. 20a, positioning mechanism 683 configured to adjust in rotational adjustment direction 668 may be placed so that the center of rotational adjustment direction 668 is coincident with first rotational axis 608. In this configuration base link 685 or adjustment link 686 of positioning mechanism 683 may be the same as first segment 604 or second segment 605 of neck linkage 603. In some embodiments, actuator 615 is not configured to create a torque about positioning mechanism 683, and positioning mechanism 683 may be used to adjust engagement angle 611 or engagement position, resting angle 619 or resting position, or stow position 629 of neck supporting exoskeleton 600 relative to neck extension angle 618 of person's head 671 relative to person's torso 672. In other embodiments, actuator 615 is configured to create a torque about positioning mechanism 683, and positioning mechanism 683 may fix first segment 604 of linkage 603 relative to second segment 605 of linkage 603 about rotational adjustment direction 668.

Figure 21:
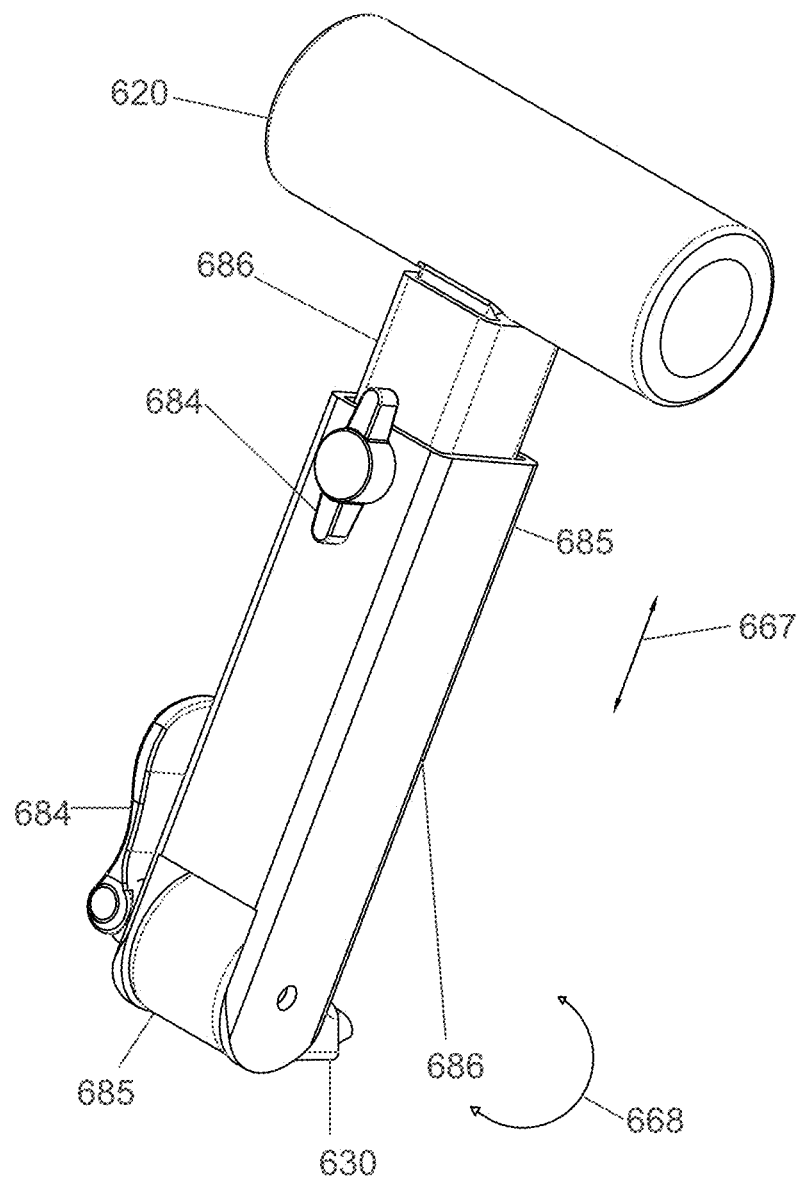
FIG. 21 shows a perspective view of an alternative embodiment of a linear and rotary positioning mechanism.
Figure 22:
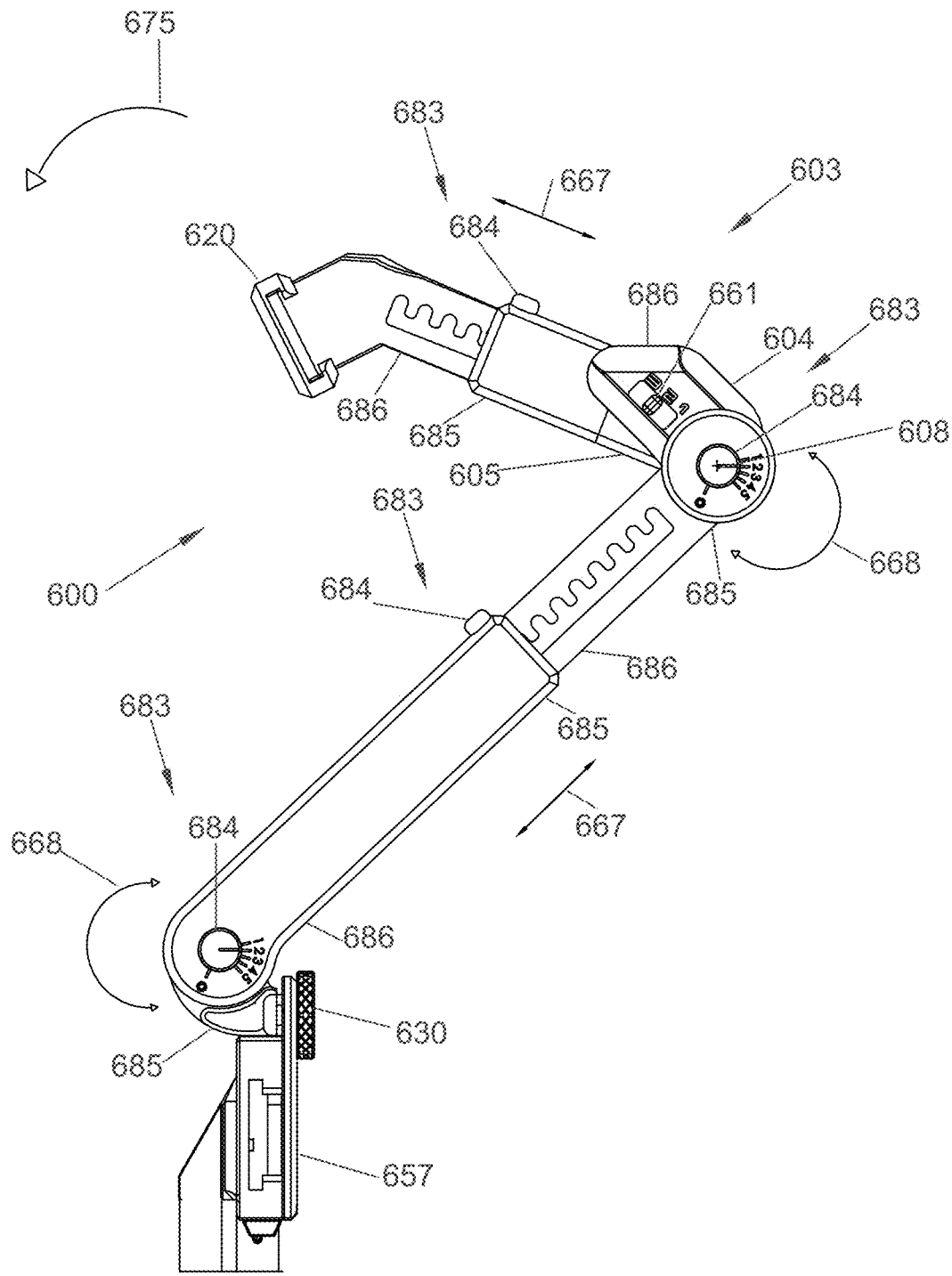
FIG. 22 shows a side view of a neck supporting exoskeleton with a rotary and linear positioning mechanism configuration.

FIG. 21 shows an alternate embodiment of positioning mechanism 683 configured to adjust the location of base link 685 relative to adjustment link 686 in continuous increments. Positioning mechanism 683 may comprise position locking element 684 that is a cam-lock clamp that selectively couples adjustment link 686 relative to base link 685 about rotational adjustment direction 668 through friction forces. Similarly positioning mechanism 683 may comprise position locking element 684 that is a set screw that selectively couples adjustment link 686 relative to base link 685 about linear adjustment direction 667 through friction forces, FIG. 22 shows a side view of an embodiment of neck supporting exoskeleton 600 comprising multiple positioning mechanisms 683 to adjust the location of head pillow 620 relative to torso frame 657. Neck supporting exoskeleton 600 may comprise first positioning mechanism 683 coupled to torso frame 657 configured to adjust first rotational axis 608 relative to torso frame 657 in rotational adjustment direction 668, and second positioning mechanism 683 coupled to first positioning mechanism 683 from its first end and to first segment 604 of linkage 603 from its second end configured to adjust first rotational axis 608 relative to torso frame 657 in linear adjustment direction 667. Adjustment link 686 of first positioning mechanism 683 may be the same as base link 685 of second positioning mechanism 683. Neck supporting exoskeleton 600 of FIG. 22 further comprises positioning mechanism 683 coupled to second segment 605 of linkage 603 from its first end configured to adjust the location of head pillow 620 relative to torso frame 657 about first rotational axis 608 in rotational adjustment direction 668. This may be used to adjust the value of engagement angle 611 or resting angle 619 when neck supporting exoskeleton 600 is worn by person 670. Neck supporting exoskeleton 600 of FIG. 22 further comprises positioning mechanism 683 configured to adjust the location of head pillow 620 relative to first rotational axis 608 in linear adjustment direction 667. Neck supporting exoskeleton 600 of FIG. 22 is configured to both align first rotational axis 608 with person's neck 673, engagement angle 611 or resting angle 619, and to adjust the position of head pillow 620 on person's head 671. One of skill in the art may recognize that at least one positioning mechanism 683 may be removed from the embodiment of FIG. 22 to simplify the adjustments of neck supporting exoskeleton 600. In some embodiments, all of positioning mechanisms 683 of FIG. 22 act in the sagittal plane 674 of the person 670.

Figure 23:
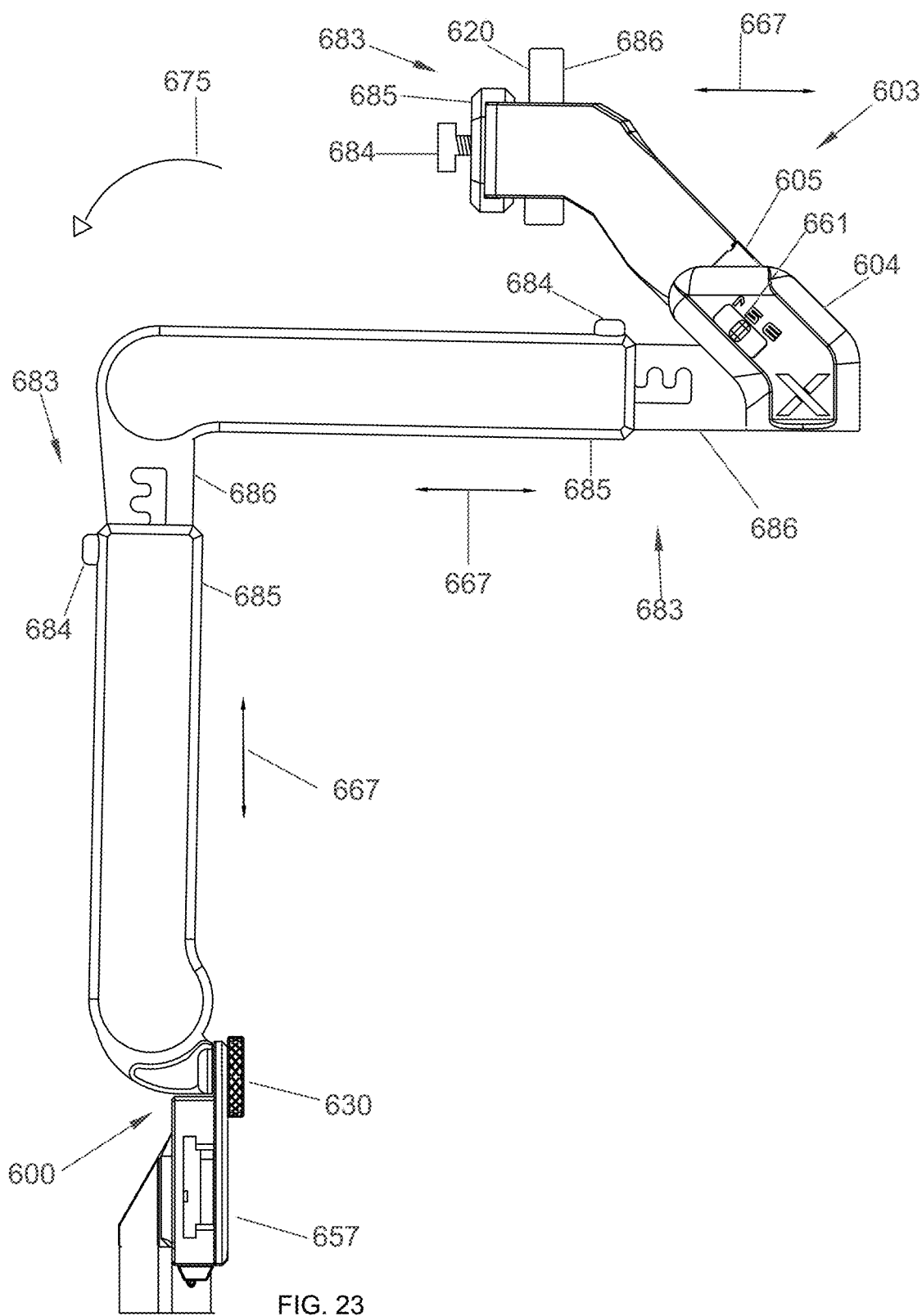
FIG. 23 shows a side view of a neck supporting exoskeleton with a linear positioning mechanism configuration.

FIG. 23 shows a side view of an alternate embodiment of neck supporting exoskeleton 600 comprising multiple positioning mechanisms 683 to adjust the location of head pillow 620 relative to torso frame 657. Neck supporting exoskeleton 600 may comprise first positioning mechanism 683 coupled to torso frame 657 configured to adjust first rotational axis 608 relative to torso frame 657 in linear adjustment direction 667 in a substantially vertical orientation, and second positioning mechanism 683 coupled to first positioning mechanism 683 from its first end and to first segment 604 of linkage 503 from its second end configured to adjust first rotational axis 608 relative to torso frame 657 in linear adjustment direction 667 in a substantially horizontal orientation. Adjusting first rotational axis 608 relative to torso frame 657 in linear adjustment direction 667 will have less impact on engagement angle 611 or engagement position of neck supporting exoskeleton 600 when worn by the person compared to rotational adjustment direction 668. Neck supporting exoskeleton 600 of FIG. 23 further comprises positioning mechanism 683 coupled to head pillow 620 from its first end and to linkage 603 from its second end configured to adjust the location of head pillow 620 relative to first rotational axis 608 in linear adjustment direction 667. In some embodiments, all of positioning mechanisms 683 of FIG. 23 act in sagittal plane 674 of person 670.

Figure 24:
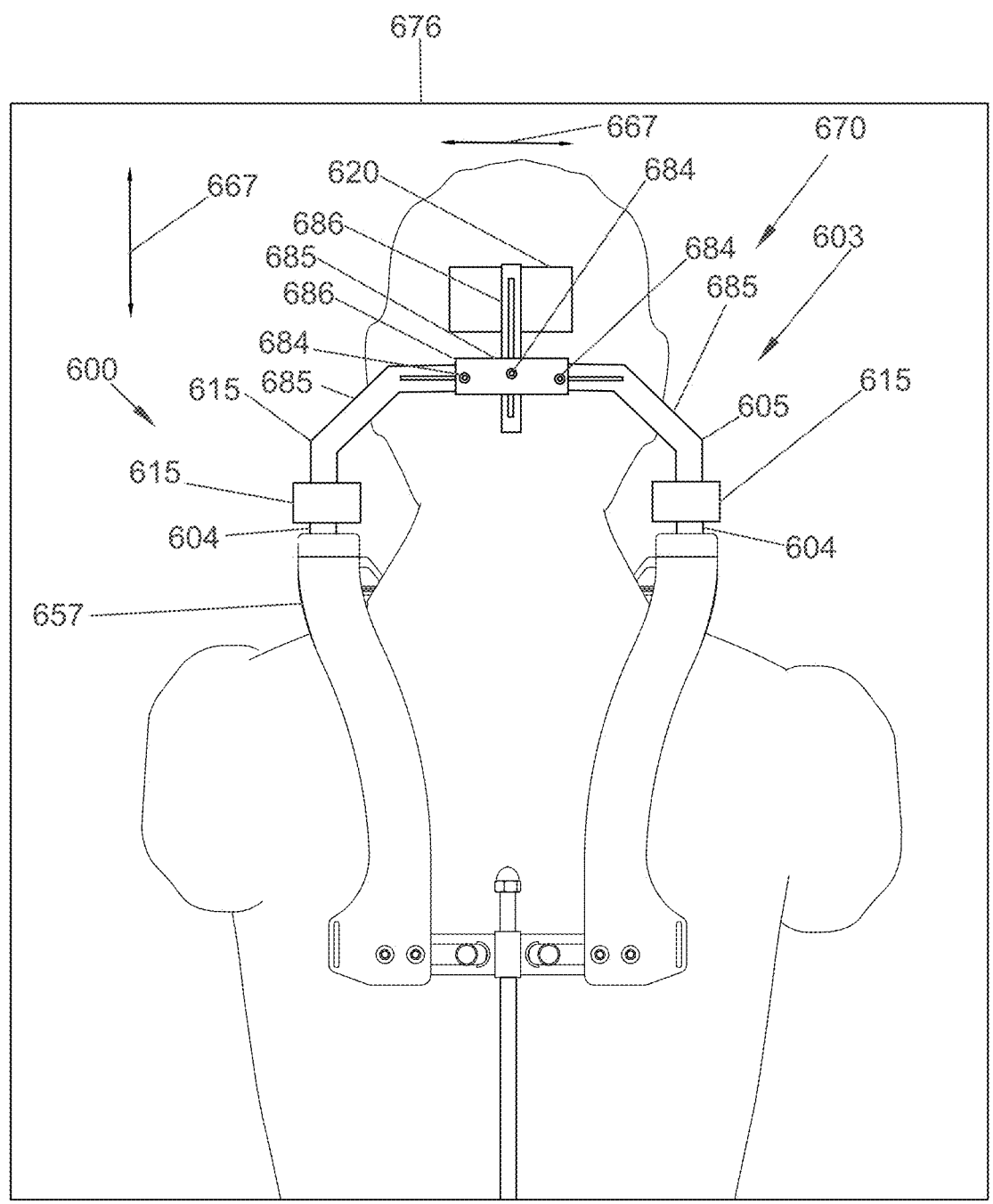
FIG. 24 shows a rear view of a neck supporting exoskeleton with an alternate linear positioning mechanism configuration.

FIG. 24 shows a rear view of an alternate embodiment of neck supporting exoskeleton 600 comprising multiple positioning mechanisms 683 to adjust the location of head pillow 620 relative to torso frame 657. Neck supporting exoskeleton 600 may comprise first positioning mechanism 683 coupled to linkage 603 from its first end to adjust head pillow 620 relative to torso frame 657 in linear adjustment direction 667 in a substantially horizontal orientation. Positioning mechanism 683 may also be used to adjust the width of neck supporting exoskeleton 600 when mounted to torso frame 657 at two points along the sides of person's neck 673. Neck supporting exoskeleton 600 may further comprise second positioning mechanism 683 coupled to head pillow 620 from its first end to adjust head pillow 620 relative to torso frame 657 in linear adjustment direction 667 in a substantially vertical orientation. In some embodiments, all of the positioning mechanisms 683 of FIG. 24 act in frontal plane 676 of person 670.

Head pillow 620 is designed to transfer supporting force 612 to person's head 671 throughout the range of motion of neck supporting exoskeleton 600. For optimum comfort, supporting force 612 should be applied to the base of the skull and avoid any upper cervical vertebrae. As the neck does not rotate about a single axis, relative motion between head 671 and head pillow 620 is difficult to avoid, especially if first rotational axis 608 is misaligned with person's neck rotational axis 669. For optimum load transfer head pillow 620 should therefore minimize relative rotation or translation between neck supporting exoskeleton 600 and person's head 671, Head pillow 620 may also be configured to apply supporting force 612 to person's head 671 in motions other than those opposing extension motion 675. This may allow neck supporting exoskeleton 600 to support additional postures, or prevent person's head 671 from moving into other at risk postures.

Figure 25A:
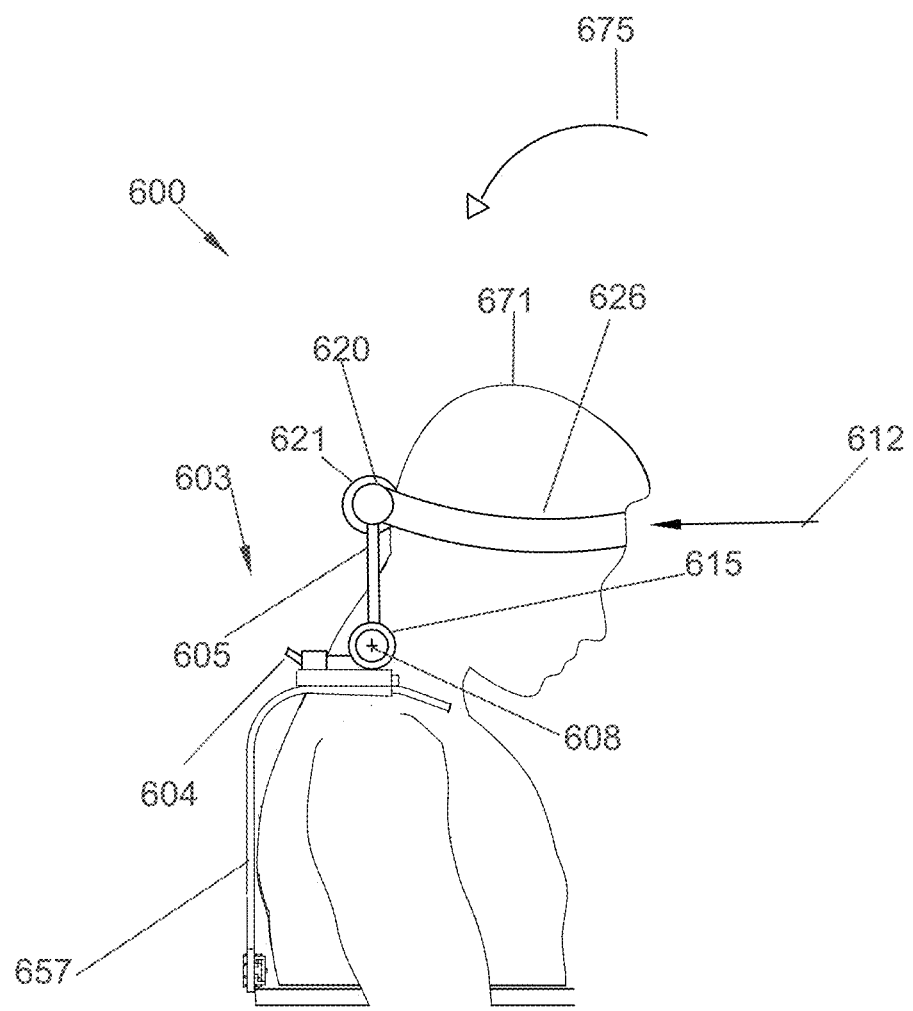
FIG. 25a shows a side view of a head pillow comprising a head strap or contoured pad.

FIG. 25a shows an embodiment of neck supporting exoskeleton 600 wherein head pillow 620 comprises contoured head pad 621 that allows for rolling contact with person's head 671. Contoured head pad 62:1 may roll with respect to head pillow 620 or may be made of a smooth material to minimize any friction if person's head 671 translates relative to the device as well as to ensure that supporting force 612 is always normal to contoured head pad 621 at the center of contact with person's head 671. FIG. 5a also shows an embodiment when head pillow 620 comprises head strap 626 coupled to head pillow 620. Head strap 626 may be configured to encircle person's head 671 and apply supporting force 612 to person's head 671 to support flexion motion. Head strap 626 may also be used to keep head pillow 620 in contact with person's head 671 when neck extension angle 618 is less than engagement angle 611, even if no supporting force 612 is applied.

Figure 25B:
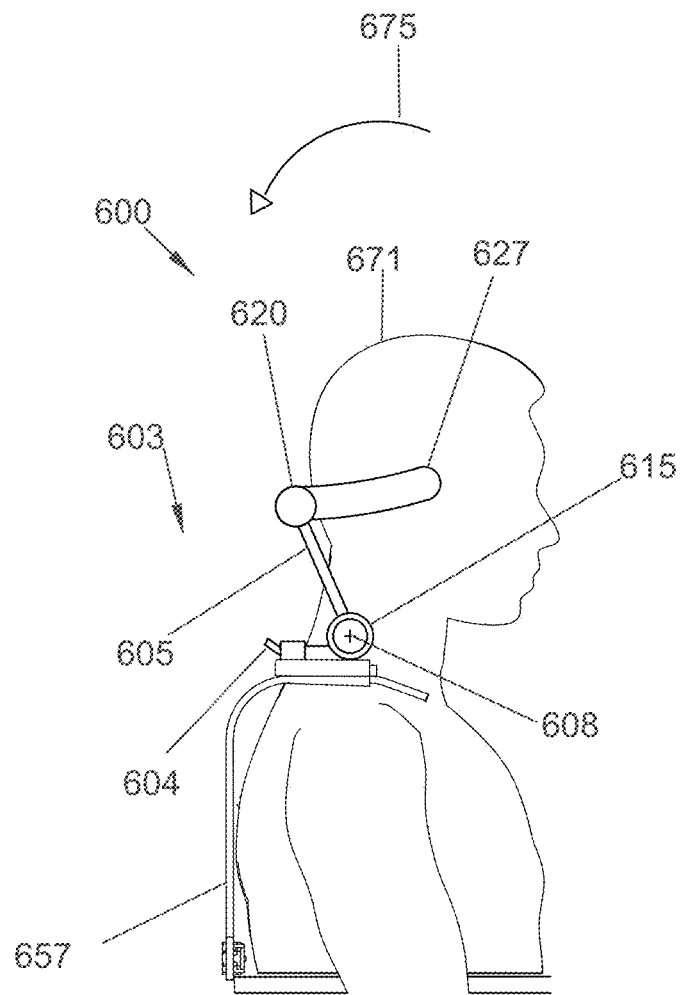
FIG. 25b shows a side view of a head pillow comprising a semi rigid head brace.

FIG. 25b shows an embodiment of neck supporting exoskeleton 600 wherein head pillow 620 comprises semi rigid head brace 627 configured to prevent motion of person's head 671 relative to head pillow 620 for motions in lateral flexion direction 677. Semi rigid head brace 627 may be configured to keep head pillow 620 in contact with person's head 671 when neck extension angle 618 is less than engagement angle 611, even if no supporting force 612 is applied.

Figure 25C:
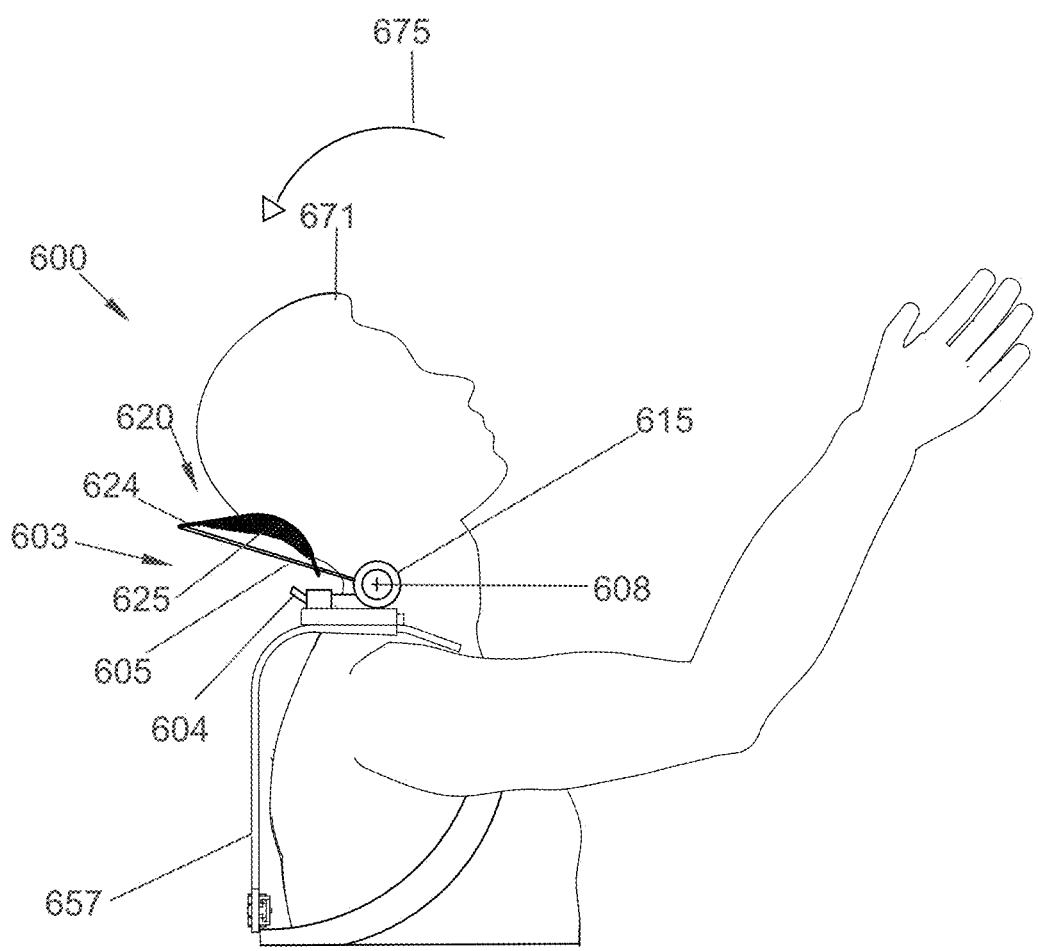
FIG. 25c shows a side view of a head pillow comprising a hammock structure.

FIG. 25c shows an embodiment of neck supporting exoskeleton 600 wherein head pillow 620 comprises a hammock configured to conform to the back of person's head 671. Head pillow 620 may comprise semi rigid frame 624 coupled to resilient structure 601 and flexible mesh 625 spanning semi rigid frame 624 configured to conform to the person's head 671.

Figure 26A:
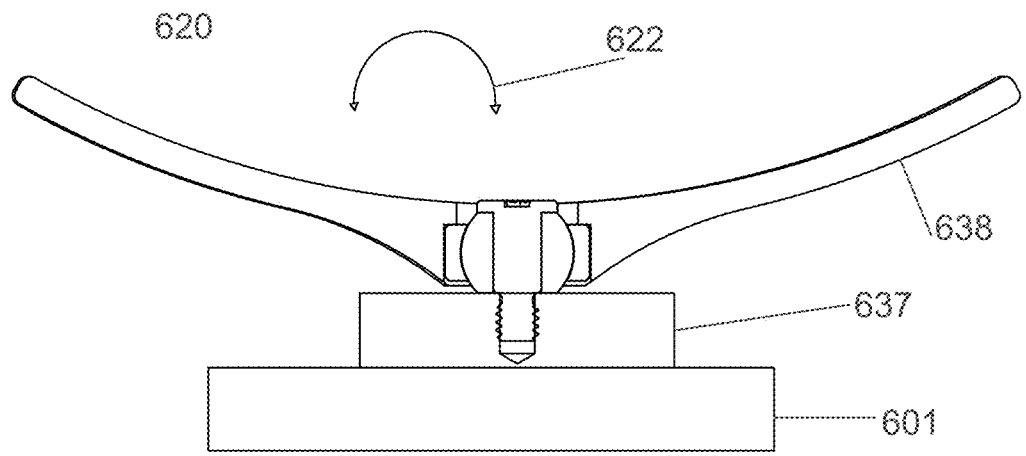
FIG. 26a shows an embodiment of a head pillow where a head contact element rotates relative to a head pillow base.
Figure 26B:
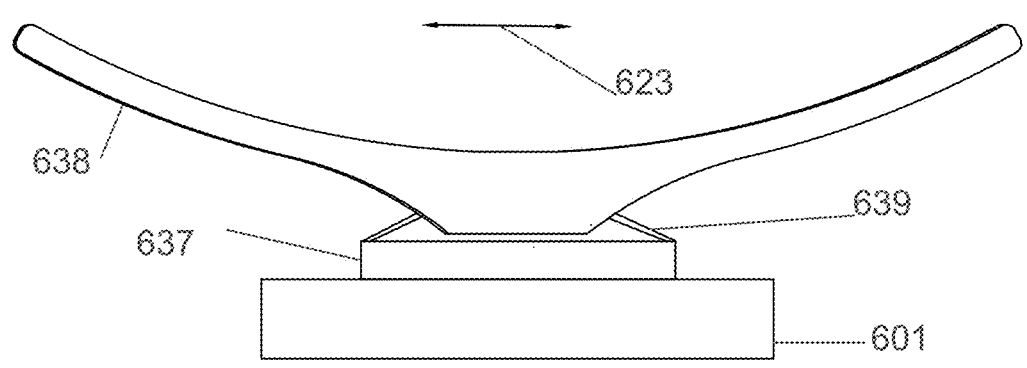
FIG. 26b shows an embodiment of a head pillow where a head contact element translates relative to a head pillow base.
Figure 26C:
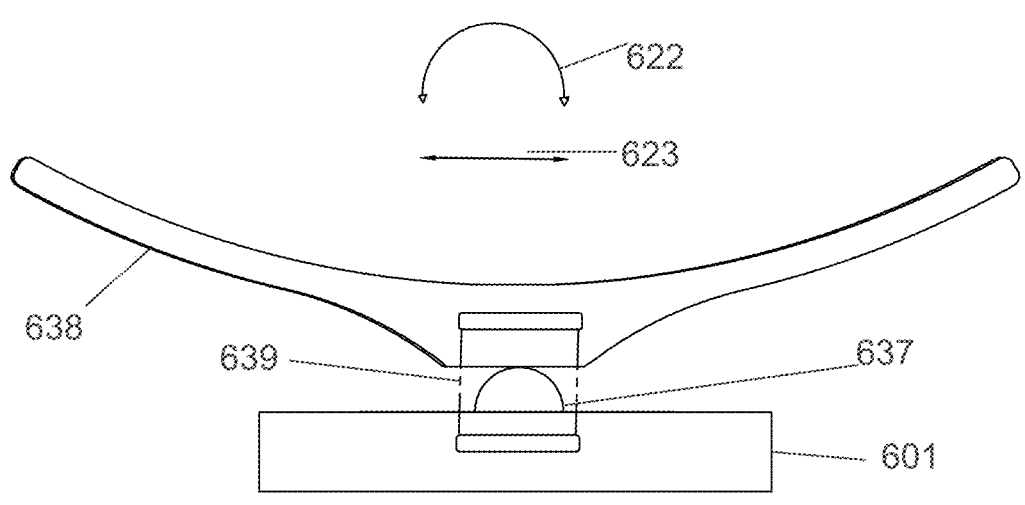
FIG. 26c shows an embodiment of a head pillow where a head contact element rotates and translates relative to a head pillow base.

In some embodiments, head pillow 620 further comprises head pillow base 637 coupled to resilient structure 601 and head contact element 638 moveably coupled to head pillow base 637 to minimize relative motion between head pillow 620 and person's head 671. FIG. 26a shows an embodiment when head contact element 638 is rotationally coupled to head pillow base 637 about at least one rotation direction 622. In some embodiments, head contact element 638 is coupled to head pillow base 637 by a spherical bearing allowing rotation of head contact element 638 relative to head pillow base 637 in multiple planes. The rotational coupling between head contact element 638 and head pillow base 637 may be damped, lockable, or spring loaded to a centered position. FIG. 26b shows an embodiment when head contact element 638 is translationally coupled to head pillow base 637 about at least one translation direction 623. Head pillow 620 may further comprise at least one head pillow spring 639 configured to bias the coupling between head contact element 638 and head pillow base 637 to a centered position. Head pillow spring 639 may further serve to limit how far head contact element 638 may translate relative to head pillow base 637. FIG. 26c shows an embodiment when head contact element 638 is rotationally and translationally coupled to head pillow base 637 about at least one rotation direction 622 and at least one translation direction 623. Head pillow 620 may further comprise at least one head pillow spring 639 configured to bias the coupling between head contact element 638 and head pillow base 637 to a centered position. Head pillow spring 639 may further serve to limit how far head contact element 638 may translate or rotate relative to head pillow base 637. Head pillow spring 639 may be an elastic strap, coil spring, compression spring, tension spring, compressible rubber disk, or similar element.

Figure 27A:
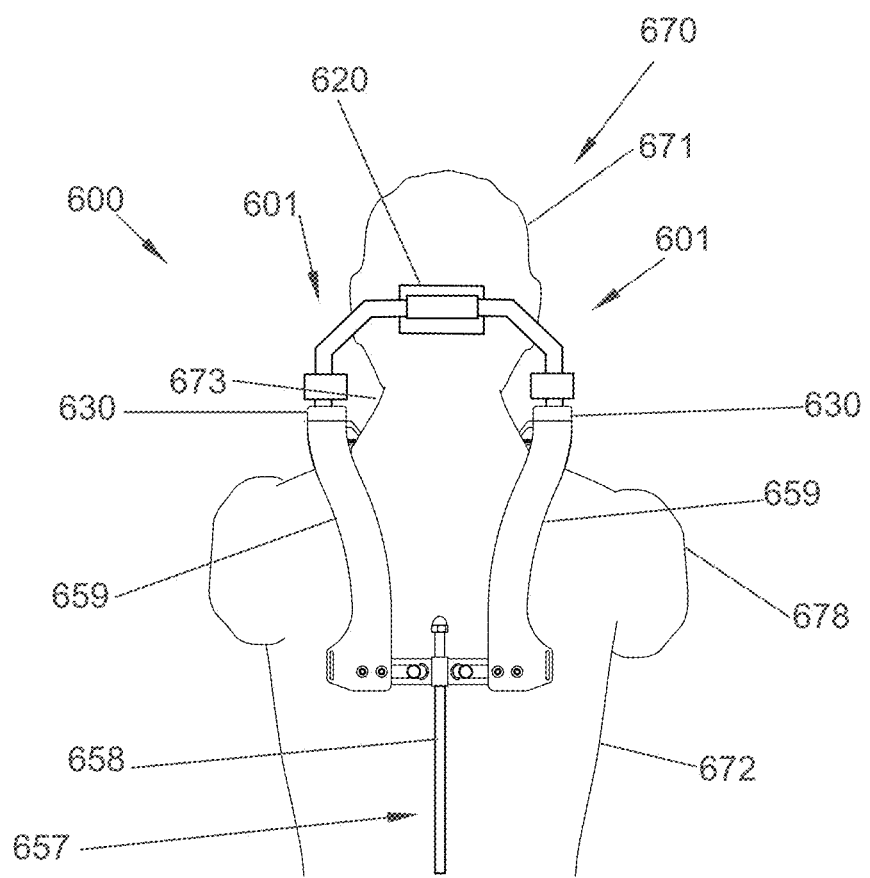
FIG. 27a shows an embodiment of resilient structure mounted to a shoulder frame of a torso frame.
Figure 27B:
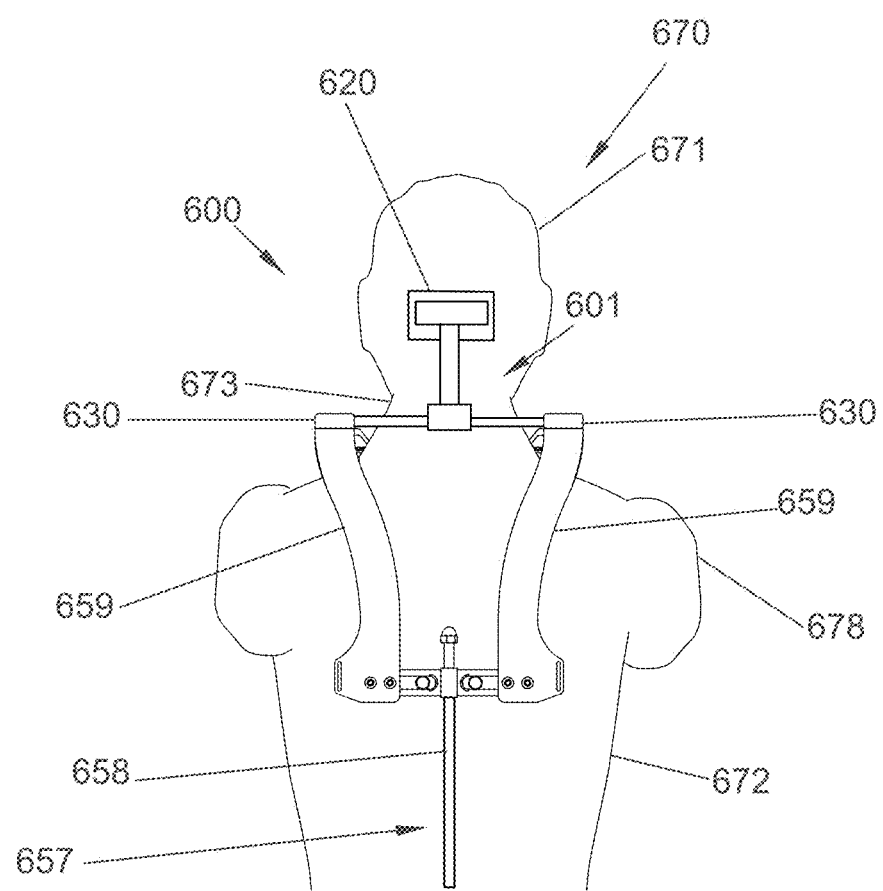
FIG. 27b shows an alternate embodiment of resilient structure mounted to a shoulder frame of a torso frame.
Figure 27C:
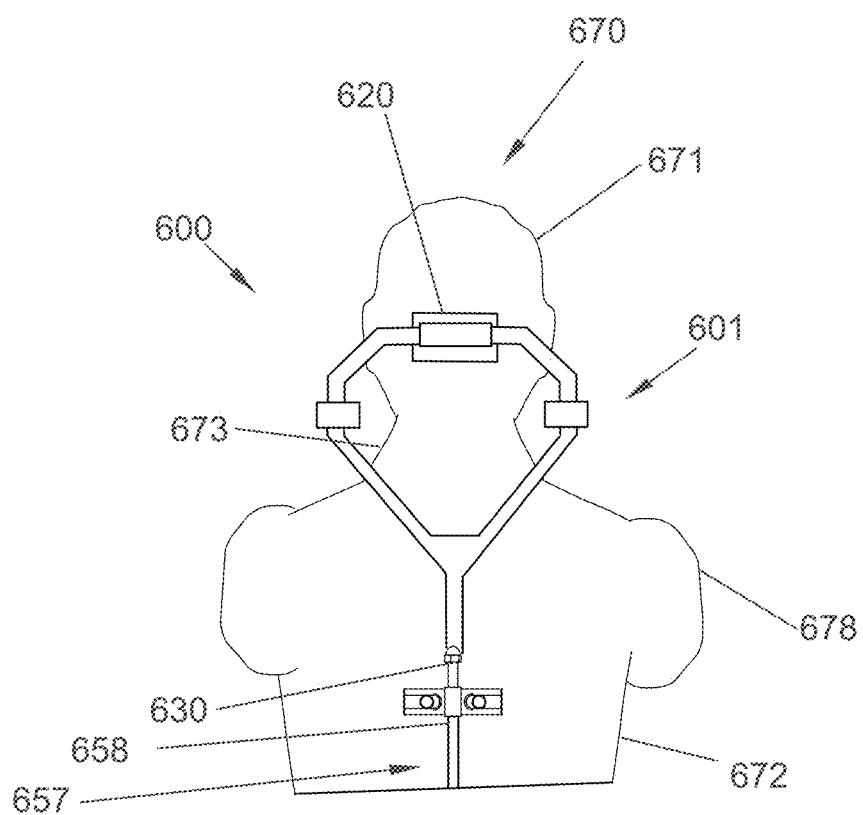
FIG. 27c shows an embodiment of resilient structure mounted to a spine frame of a torso frame.
Figure 27D:
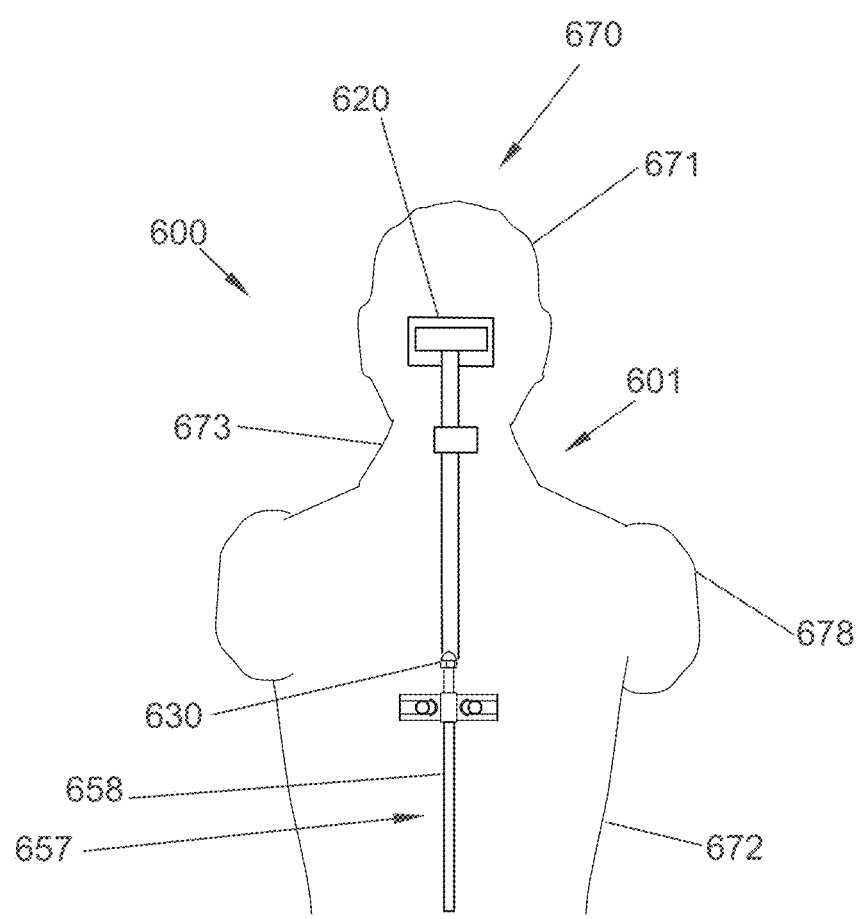
FIG. 27d shows an alternate embodiment of resilient structure mounted to a spine frame of a torso frame.
Figure 27E:
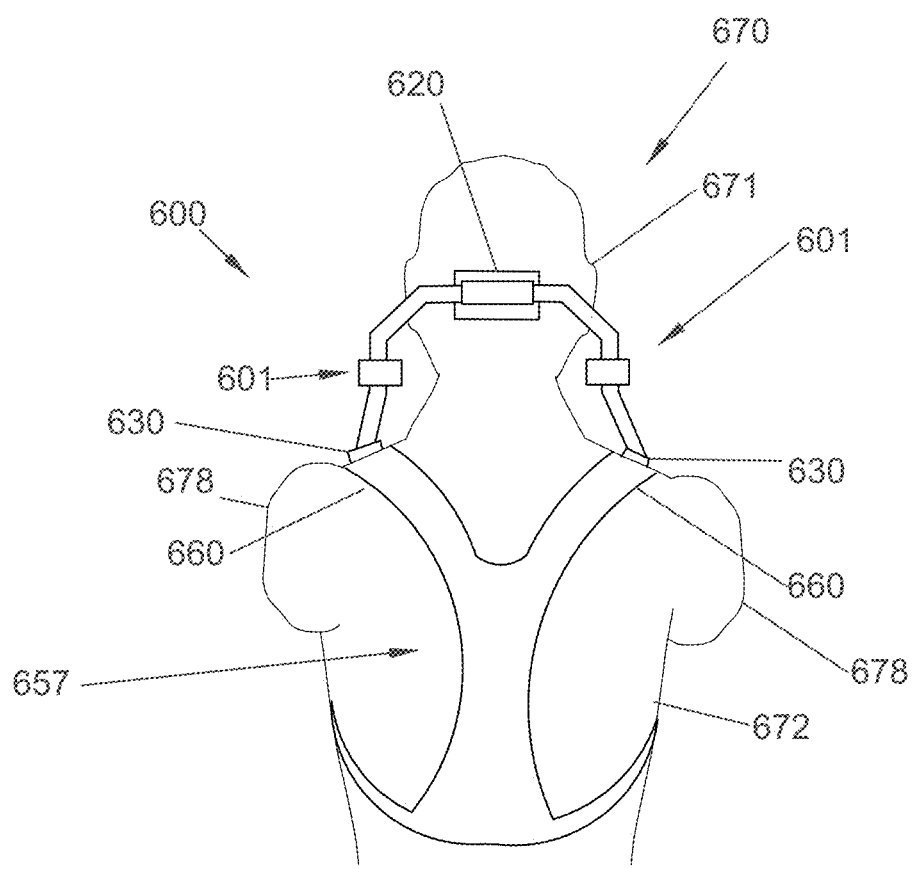
FIG. 27e shows an embodiment of resilient structure mounted to shoulder straps of a torso frame.

FIG. 27a and FIG. 27b show various embodiments of the structure of torso frame 657 and resilient structure 601. In the embodiment of FIG. 27a, torso frame 657 comprises at least one rigid shoulder frame 659 terminating above person's shoulder 678. Resilient structure 601 may be coupled to shoulder frame 659 to the side of person's head 671 or above person's shoulder 678. In the embodiment of FIG. 27a neck supporting exoskeleton 600 comprises shoulder frame 659 and resilient structure 601 on the right side of the person 670 and shoulder frame 659 and resilient structure 601 on the left side of the person. In the embodiment of FIG. 27b neck supporting exoskeleton 600 comprises a single resilient structure 601 coupled to shoulder frame 659 to the side of persons head 671 and coupled to shoulder frame 659 to the other side of persons head 671 wherein resilient structure 601 is located behind person's head 671, In some embodiments, neck supporting exoskeleton 600 comprises rigid spine frame 658 located behind person's torso 672, wherein resilient structure 601 is coupled to spine frame 658. In the embodiment of FIG. 27c resilient structure 601 is coupled to spine frame 658 behind person's torso 672. Resilient structure 60:1 may further separate into two segments located to the right and the left side of person's neck 673 or head 671 before connecting at head pillow 620. FIG. 27d shows an embodiment where resilient structure 601 is coupled to spine frame 658 behind person's torso 672 and connects to head pillow 620, the entirety of neck supporting exoskeleton 600 located behind person 670. FIG. 27e shows an embodiment wherein torso frame 657 comprises at least one shoulder strap 660 at least partially encircling person's shoulder 678, at least one resilient structure 601 coupled to shoulder strap 660 to the side of the person's head 671. Shoulder strap 660 may be semi rigid or flexible textile material and may be part of a backpack, safety harness, or other torso mounted structure.

Figure 28:
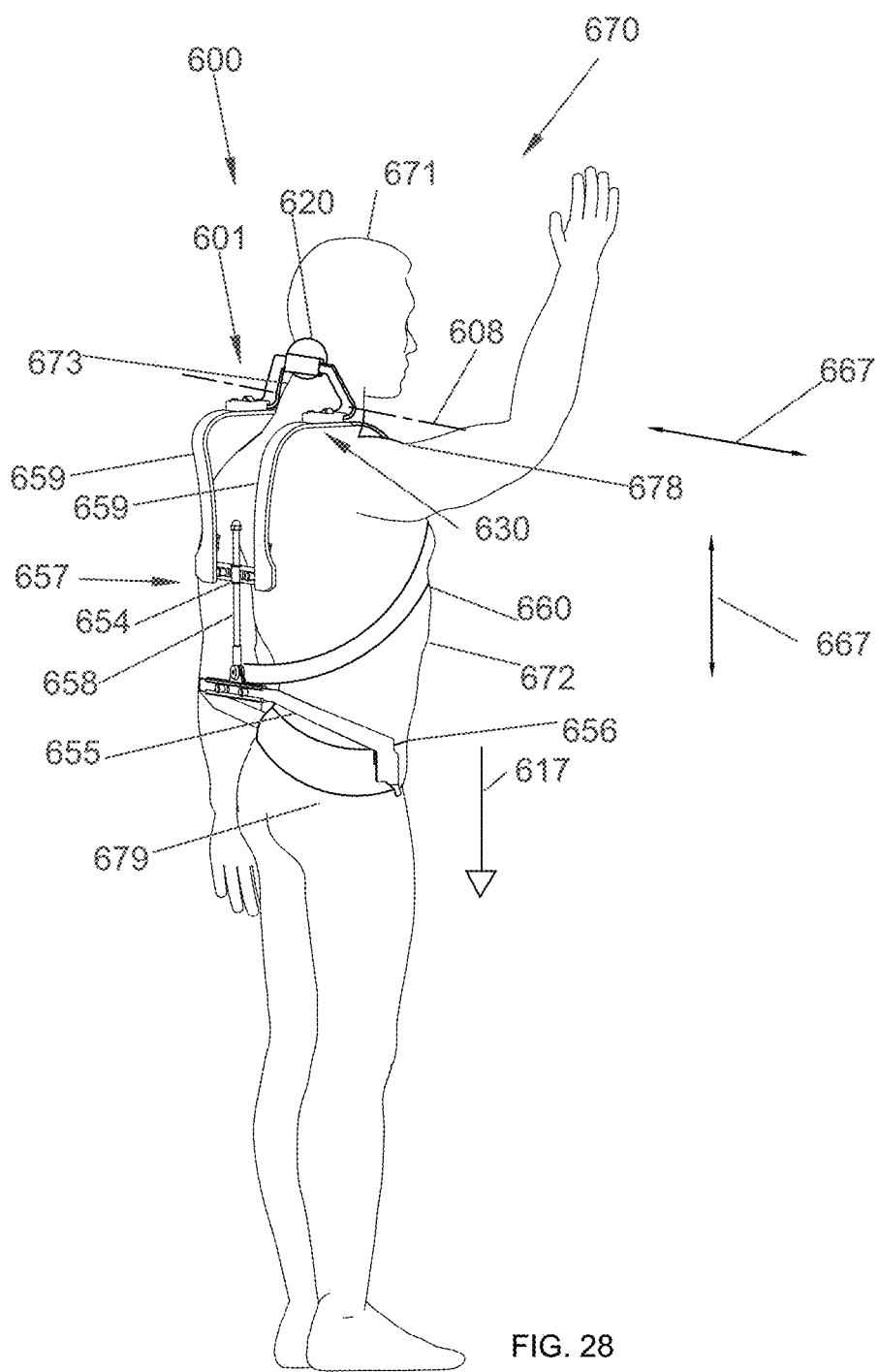
FIG. 28 shows a perspective view of a neck supporting exoskeleton torso frame

FIG. 28 shows an embodiment of torso frame 657 of neck supporting exoskeleton 600. Torso frame 657 may comprise belt 656 that partially encircles person's hips 679. Torso frame 657 may further comprise at least one shoulder strap 660 that at least partially encircles person's shoulders 678. Belt 656 and shoulder straps 660 may be configured to couple torso frame 657 to person's torso 672, In some embodiments, torso frame 657 is configured to transfer reaction forces and torques from supporting force 612 to person's torso 672. Belt 656 may be configured to apply a load to person's hips 679 corresponding to the weight of neck supporting exoskeleton 600 or reaction forces and torques from supporting force 612. Shoulder straps 660 may be configured to apply a load to person's shoulders 678 corresponding to the weight of neck supporting exoskeleton 600 or reaction forces and torques from supporting force 612. Torso frame 657 may further comprise spine frame 658 that extends along person's torso 672 parallel to gravity line 617 and adjustment base 654 translationally coupled to spine frame 658 to adjust the position of head pillow 620 relative to torso frame 657 in vertical adjustment direction 667 oriented vertically. Torso frame 657 may further comprise at least one shoulder frame 659 that is substantially rigid and translationally coupled to adjustment base 654 to adjust the position of head pillow 620 or shoulder frame 659 relative to spine frame 658 in horizontal liner adjustment direction 667. Torso frame 657 may further comprise hip frame 655 coupled to belt 656 from one end and to spine frame 658 from another end, wherein hip frame 655 is configured to transfer forces between spine frame 658 and belt 656. In some embodiments hip frame 655 is flexible to allow torso frame 657 to fit various sizes of person 657, In other embodiments hip frame 655 is rigid and adjustably connected to spine frame 658 to allow torso frame 657 to fit various sizes of person 657.

Figure 29A:
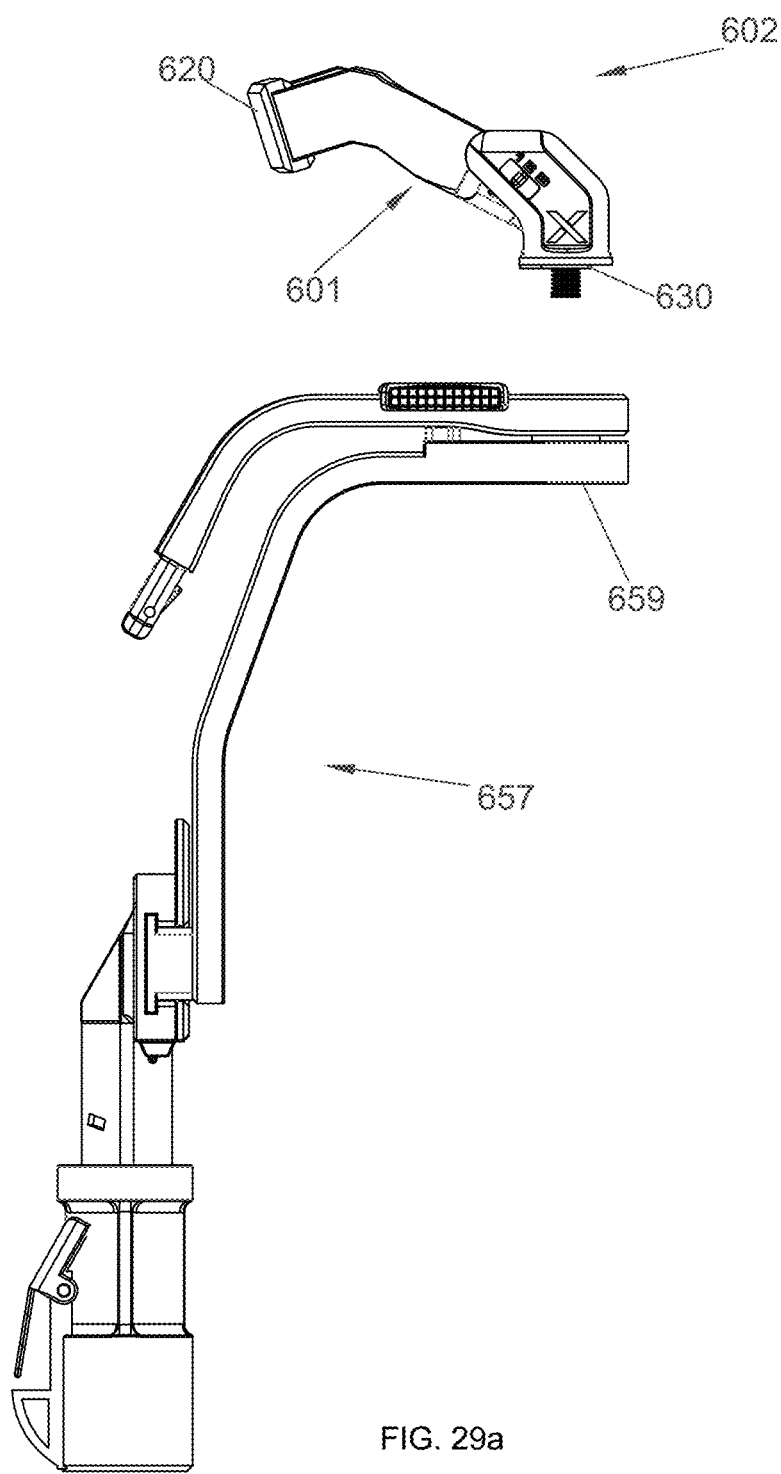
FIG. 29a shows a side view of a base coupler attaching a neck supporting module to the shoulder frame of a torso frame.
Figure 29B:
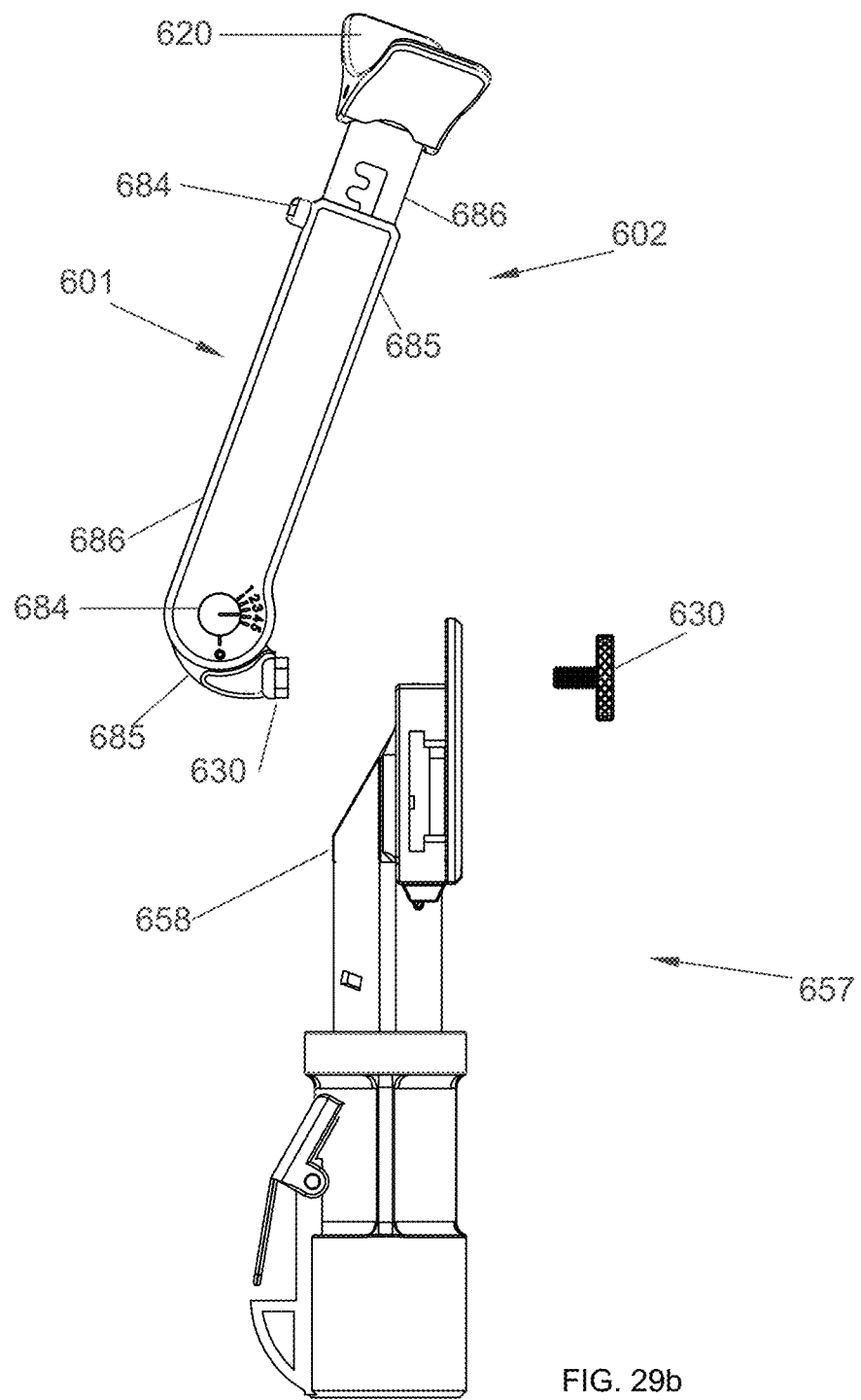
FIG. 29b shows a side view of a base coupler attaching a neck supporting module to the spine frame of a torso frame.

FIG. 29a and FIG. 29b show embodiments of neck supporting exoskeleton 600 further comprising exoskeleton coupler 630 configured to allow quick connect and quick disconnect coupling between torso frame 657 and resilient structure 601. Exoskeleton coupler 630 is configured to couple to torso frame 657 from its first end and to resilient structure 601 from its second end and transfer forces between resilient structure 601 and torso frame 657. When disconnected, exoskeleton coupler 630 may remain with either resilient structure 601 or torso frame 657. Alternatively, exoskeleton coupler 630 may comprise a first half configured to couple to a second half, wherein first half is coupled to torso frame 657 and second half is coupled to resilient structure 601. A selective coupling between resilient structure 601 and torso frame 657 allows for a modular connection between different versions, sizes, and strengths of resilient structure 601 or torso frame 657 without having to replace both structures. A selective coupling to torso frame 657 may allow a modular connection of neck supporting exoskeleton 600 to various other types of exoskeleton such as shoulder supporting exoskeleton. Alternatively, neck supporting exoskeleton 600 may be quickly attached or removed from torso frame 657 while it is being worn by the person 670 to account for different support requirements of a task, different size users, or different amounts of torque required. For usability purposes a tool should not be needed to attach or detach the neck supporting exoskeleton to the torso frame. Examples of exoskeleton coupler mechanism may include but aren't limited to: screws, latches, buckles, magnetic clasps, slot inserts, or any other common fastening mechanism. FIG. 29a shows an embodiment where exoskeleton coupler 630 is configured to couple resilient structure 601 to shoulder frame 659 of torso frame 657 at a location above person's shoulders 678 or to the side of person's head 671. FIG. 29b shows an embodiment where exoskeleton coupler 630 is configured to couple resilient structure 601 to spine frame 658 of torso frame 657 at a location behind person's torso 672. FIG. 27e shows an embodiment where exoskeleton coupler 630 is attached to shoulder strap 660 of torso frame 657. When exoskeleton coupler 630 has disconnected resilient structure 601 from torso frame 657, the part of neck supporting exoskeleton 600 comprising exoskeleton coupler 630, resilient structure 601, and head pillow 620 constitutes neck supporting module 602 configured to be attached to torso frame 657.

Figure 30:
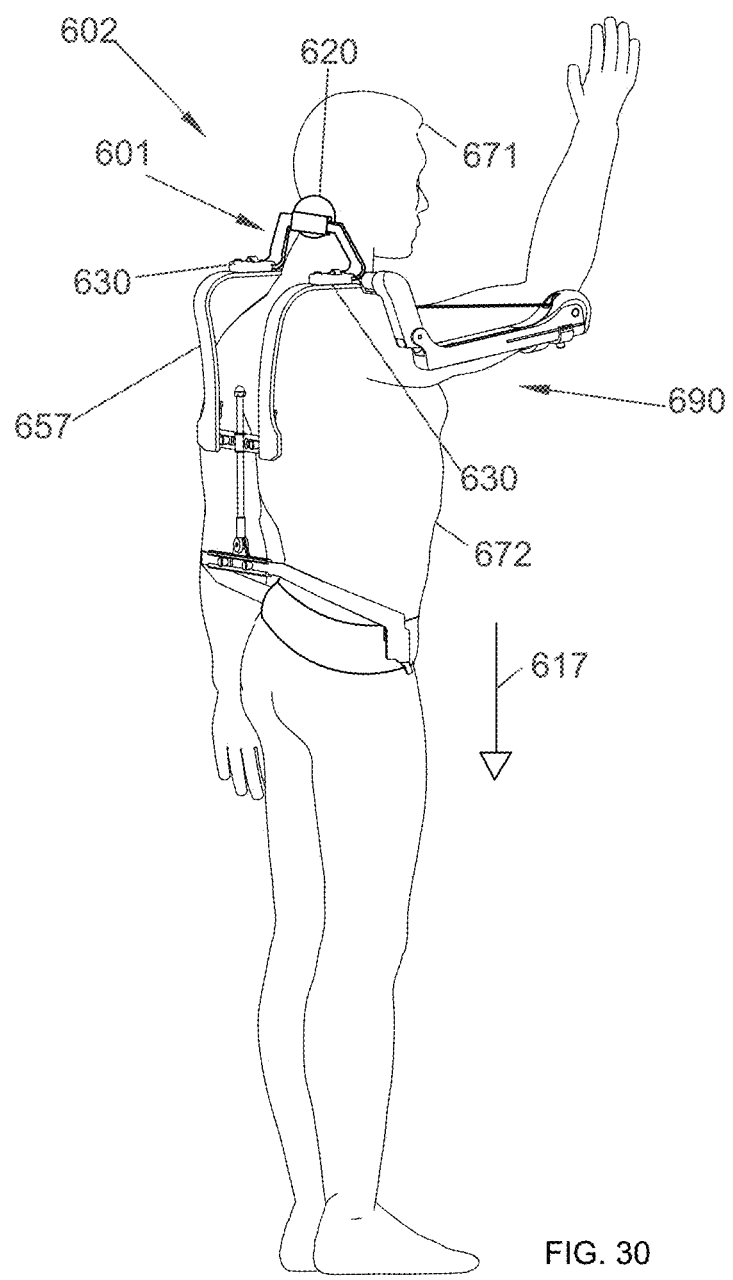
FIG. 30 shows a perspective view of a neck supporting module attached to a shoulder supporting exoskeleton

FIG. 30 shows another embodiment of neck supporting exoskeleton 600 wherein torso frame 657 is a component of a separate system such as wearable exoskeleton 690 to support a person's arms or back, backpack, tool belt, safety harness or a standalone torso frame 657. In one embodiment, neck supporting exoskeleton 600 comprises neck supporting module 602 and torso frame 657 of a separate exoskeleton system. Neck supporting module 602 is configured to attach to a wearable exoskeleton 690 to support person's head 671 during extension motions of person's neck 673, In other embodiments, neck supporting module 602 is configured to attach to torso frame 657 of wearable exoskeleton 690. Neck supporting module 602 comprises exoskeleton coupler 630 configured to be coupled to wearable exoskeleton 690. Exoskeleton coupler 630 is configured to transfer reaction forces and torques between neck supporting module 602 and torso frame 657. Exoskeleton coupler 630 may be coupled to many locations on torso frame 657. Neck supporting module 602 also comprises head pillow 620 configured to contact the rear portion of person's head 671 during extension motions of person's neck 673. In some embodiments, neck supporting module 602 also comprises at least one resilient structure 601 coupled to exoskeleton coupler 630 from a first end and to head pillow 620 from a second end. Resilient structure 601 is configured to allow for relative motion between head pillow 620 and exoskeleton coupler 630, When person's neck 673 extends beyond an engagement angle 611, resilient structure 601 provides a torque resisting the extension motion of head pillow 620 relative to exoskeleton coupler 630 thereby providing support for person's head 671. In another embodiment, resilient structure 601 further comprises linkage 603 coupled to exoskeleton coupler 630 from its first end and to head pillow 620 from its second end, linkage 603 allowing for relative motion between head pillow 620 and exoskeleton coupler 630. Linkage 603 is configured to allow for relative motion between head pillow 620 and exoskeleton coupler 630. Resilient structure 601 may also comprise at least one actuator 615 configured to generate a resistance in response to motion of head pillow 620 relative to exoskeleton coupler 630. When person's neck 673 extends beyond engagement angle 611, actuator 615 provides a torque resisting extension motion 675 of head pillow 620 relative to exoskeleton coupler 630 thereby providing support for person's head 671. In this embodiment, linkage 603 directs the motion of head pillow 620 relative to exoskeleton coupler 630 while actuator 615 applies forces or torques to the direction of motion defined by linkage 603. When person's neck 673 extends beyond engagement angle 611, actuator 615 provides a torque resisting extension motion 675 of the head pillow 620 relative to exoskeleton coupler 630 thereby providing support for person's head 671. In other embodiments when the person's neck 673 extends beyond engagement angle 611, the resilient structure 601 generates a supporting force 612 onto head pillow 620 resisting extension motion 675 of head pillow 620 and person head 671 relative to exoskeleton coupler 630 thereby providing support for person's head 671, All enclosed descriptions and figures of neck supporting exoskeleton 600 can be equally applied to the neck supporting module 602 by replacement of torso frame 657 with exoskeleton coupler 630.

Conclusion

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatuses. Accordingly, the present examples are to be considered as illustrative and not restrictive.

What is claimed is:

1. An exoskeleton configured to be worn by a person to support a head of the person during an extension motion of a neck of the person, the supporting exoskeleton comprising:
    a torso frame having a first portion configured to apply a load onto at least one shoulder of the person and a second portion extending from the first portion, the second portion configured to extend along the spine of the person;
    a head pillow configured to contact only a rear portion of the person's head; and
    a resilient structure comprising a first end and a second end, the first end coupled to the torso frame, the second end coupled to the head pillow, the resilient structure configured to rotate the head pillow relative to the torso frame in a sagittal plane of the person about a first axis passing through the neck of the person and to generate a supporting force onto the head pillow in response to the extension motion of the neck of the person,
    wherein the resilient structure defines an engagement angle where the head pillow is adapted to contact the rear portion of the person's head,
    wherein the neck of the person extends posteriorly at a neck extension angle, the neck extension angle increasing from a non-engaging angle where the head of the person does not contact the head pillow, and
    wherein the resilient structure defines the neck extension angle such that the head pillow is adapted to resist the extension motion of the neck of the person and to support the head of the person.

2. The exoskeleton of claim 1, wherein the resilient structure comprises a leaf spring configured to bend about the first axis.

3. The exoskeleton of claim 1, wherein the resilient structure further comprises a linkage, comprising a first segment, coupled to the torso frame, and a second segment, coupled to the head pillow, wherein the second segment is configured to rotate relative to the first segment about the first axis.

4. The exoskeleton of claim 1, further comprising a positioning mechanism, wherein the positioning mechanism allows the person to change a location of the head pillow relative to the torso frame.

5. The exoskeleton of claim 4, wherein the positioning mechanism comprises:
a base link;
an adjustment link, rotationally coupled to the base link; and
a position locking element, configured to move between at least a first position and a second position,
wherein, when the position locking element is in the first position, the adjustment link can freely rotate relative to the base link, and
wherein, when the position locking element is in the second position, the adjustment link is fixed relative to the base link.

6. The exoskeleton of claim 4, wherein the positioning mechanism comprises:
a base link;
an adjustment link, translationally coupled to the base link; and
a position locking element, configured to move between at least a first position and a second position,
wherein, when the position locking element is in the first position, the adjustment link can freely translate relative to the base link, and
wherein, when the position locking element is in the second position, the adjustment link is fixed relative to the base link.

7. The exoskeleton of claim 1, wherein the head pillow comprises:
a head pillow base, coupled to the resilient structure, and
a head contact element, movably coupled to the head pillow base adapted to minimize relative motion between the head pillow and the head of the person.

8. The exoskeleton of claim 1,
wherein the torso frame further comprises a rigid spine adapted to terminate behind the torso of the person, and
wherein the resilient structure is coupled to the rigid spine adapted to be behind the head of the person.

9. The exoskeleton of claim 1, wherein the first portion is a rigid shoulder frame adapted to terminate above the at least one shoulder of the person, and wherein the resilient structure is coupled to the rigid shoulder frame.

10. The exoskeleton of claim 1, further comprising a stow lock configured to selectively prevent flexion motion of the head pillow relative to the torso frame past a stow position adapted to be located past the engagement angle in the extension motion of the person's neck,
wherein the stow lock is configured to be moved between a first position and a second position,
wherein, when the stow lock is in the first position and the head pillow is at a stow position, the stow lock does not prevent the head pillow from moving relative to the torso frame, and
wherein, when the stow lock is in the second position and the head pillow is at the stow position, the stow lock prevents the head pillow from moving relative to the torso frame in a flexion motion to stow the head pillow out of a workspace of the person when the exoskeleton is not in use.

11. The exoskeleton of claim 1, wherein the resilient structure further comprises a first resilient structure adapted to be to the right side of the person's head and a second resilient structure adapted to be to the left side of the person's head.

12. The exoskeleton of claim 1, wherein the resilient structure is separated into two segments adapted to be located on both the right and left side of the person's neck or head.

13. The exoskeleton of claim 1, further comprising a flexion hard stop configured to prevent a flexion motion between the head pillow and the torso frame in the sagittal plane of the person past the engagement angle.

14. The exoskeleton of claim 13, wherein the resilient structure is preloaded against the flexion hard stop at the engagement angle.

15. The exoskeleton of claim 13, wherein the flexion hard stop comprises a flexible tensile element.

16. The exoskeleton of claim 13, wherein the flexion hard stop is adjustably coupled to the resilient structure, the head pillow, or the torso frame to allow for adjustment of the engagement angle.

17. The exoskeleton of claim 1, further comprising an extension hard stop configured to prevent the head pillow from moving relative to the torso frame in the extension motion at a resting angle which is greater than the engagement angle.

18. The exoskeleton of claim 17, wherein the extension hard stop is adjustably coupled to the resilient structure, the head pillow, or the torso frame to adjust the resting angle.

* * * * *